US012799537B2

(12) United States Patent
Li et al.

(10) Patent No.: US 12,799,537 B2
(45) Date of Patent: Nov. 17, 2026

(54) METHOD FOR PREDICTING CANCER RISK VALUE BASED ON MULTI-OMICS AND MULTIDIMENSIONAL PLASMA FEATURES AND ARTIFICIAL INTELLIGENCE

(71) Applicant: SeekIn Inc., San Diego, CA (US)

(72) Inventors: Shiyong Li, Shenzhen (CN); Mao Mao, Shenzhen (CN); Guolin Zhong, Shenzhen (CN); Yan Chen, Huizhou (CN); Wei Wu, Shenzhen (CN); Yumin Feng, Shenzhen (CN)

(73) Assignee: SeekIn Inc., San Diego, CA (US)

( * ) Notice: Subject to any disclaimer, the term of this patent is extended or adjusted under 35 U.S.C. 154(b) by 1017 days.

(21) Appl. No.: 17/400,778

(22) Filed: Aug. 12, 2021

(65) Prior Publication Data

US 2022/0136062 A1 May 5, 2022

(30) Foreign Application Priority Data

Oct. 30, 2020 (CN) ......................... 202011193149.8
Oct. 30, 2020 (CN) ......................... 202011197469.0
Jun. 21, 2021 (CN) ......................... 202110687795.8

(51) Int. Cl.

| | |
|---|---|
| ***G01N 33/48*** | (2006.01) |
| ***C12Q 1/6886*** | (2018.01) |
| ***G01N 33/50*** | (2006.01) |
| ***G06F 17/18*** | (2006.01) |
| ***G16B 20/20*** | (2019.01) |

(Continued)

(52) U.S. Cl.

CPC ........... *C12Q 1/6886* (2013.01); *G06F 17/18* (2013.01); *G16B 20/20* (2019.02); *G16B 30/00* (2019.02); *G16B 40/00* (2019.02); *C12Q 2600/156* (2013.01)

(58) Field of Classification Search

CPC .. C12Q 1/6886; C12Q 2600/156; C12Q 1/68; G06F 17/18; G16B 20/20; G16B 30/00; G16B 40/00; G16B 25/10; G16B 40/20; G16H 50/20

See application file for complete search history.

(56) References Cited

U.S. PATENT DOCUMENTS

2013/0288244 A1 10/2013 Deciu et al.
2017/0024513 A1 1/2017 Lo et al.
2018/0068083 A1 3/2018 Cohen et al.

(Continued)

FOREIGN PATENT DOCUMENTS

CN 101365950 A 2/2009
CN 102128876 A 7/2011

(Continued)

OTHER PUBLICATIONS

Shendure et al. DNA sequencing at 40: past, present and future. Nature, vol. 550, pp. 345-353. (Year: 2017).*

(Continued)

*Primary Examiner* — Russell S Negin
(74) *Attorney, Agent, or Firm* — Fish & Richardson P.C.

(57) ABSTRACT

The present application relates to the field the field of bioinformatics. Specifically, the present application relates to a method, system, electronic device and computer-readable medium for predicting the source of a sample to be tested based on multi-omics and multidimensional plasma features and artificial intelligence.

12 Claims, 24 Drawing Sheets

Specification includes a Sequence Listing.

(51) Int. Cl.
*G16B 30/00* (2019.01)
*G16B 40/00* (2019.01)

(56) References Cited

U.S. PATENT DOCUMENTS

| | | | |
|---|---|---|---|
| 2018/0307796 A1 | 10/2018 | Jiang et al. |
| 2020/0005901 A1 | 1/2020 | Cohen et al. |
| 2021/0256323 A1 | 8/2021 | Cohen et al. |
| 2023/0332238 A1 | 10/2023 | Zhong et al. |
| 2024/0412868 A1 | 12/2024 | Li et al. |

FOREIGN PATENT DOCUMENTS

| | | |
|---|---|---|
| CN | 103484566 A | 1/2014 |
| CN | 106407742 A | 2/2017 |
| CN | 106661614 A | 5/2017 |
| CN | 107292114 A | 10/2017 |
| CN | 107723363 A | 2/2018 |
| CN | 110739027 A | 4/2018 |
| CN | 108322347 A | 7/2018 |
| CN | 108446848 A | 8/2018 |
| CN | 109036571 A | 12/2018 |
| CN | 109097417 A | 12/2018 |
| CN | 111370056 A | 7/2020 |
| CN | 111370057 A | 7/2020 |
| CN | 111370061 A | 7/2020 |
| CN | 111788486 A | 10/2020 |
| CN | 112086129 A | 12/2020 |
| CN | 112397143 A | 2/2021 |
| CN | 112410422 A | 2/2021 |
| CN | 112927755 A | 6/2021 |
| CN | 117831690 A | 4/2024 |
| WO | WO 2016/090584 A1 | 6/2016 |
| WO | WO 2016094330 A2 | 6/2016 |
| WO | WO 2016/135478 A1 | 9/2018 |
| WO | WO 2019/018374 A1 | 1/2019 |
| WO | WO 2019/047181 A1 | 3/2019 |
| WO | WO 2020/006547 A1 | 1/2020 |
| WO | WO 2020/094775 A1 | 5/2020 |
| WO | WO 2020/232548 A1 | 11/2020 |
| WO | WO 2021/247577 A1 | 12/2021 |
| WO | WO 2022/015700 A1 | 1/2022 |
| WO | WO 2024/250730 A1 | 12/2024 |

OTHER PUBLICATIONS

He et al. Genome-wide prediction of cancer driver genes based on SNP and cancer SNV data. Am J Cancer Res. vol. 4, pp. 394-410. (Year: 2014).*

Cohen et al., "Detection and localization of surgically resectable cancers with a multi-analyte blood test," Science, Feb. 23, 2018, 359(6378): 926-930.

Del Villano et al, "Radioimmunometric assay for a monoclonal antibody-defined tumor marker, CA 19-9," Clinical Chemistry, Mar. 1, 1983, 29(3):549-552 (Abstract Only).

Ji et al., "Identifying occult maternal malignancies from 1/93 million pregnant women undergoing noninvasive prenatal screening tests," Genetics in Medicine, Apr. 12, 2019, 10 pages.

Locker et al., "ASCO 2006 Update of Recommendations for the Use of Tumor Markers in Gastrointestinal Cancer," Journal of Clinical Oncology, Nov. 20, 2006, 24(33):5313-5327.

Muraro et al., "Generation and Characterization of B72.3 Second Generation Monoclonal Antibodies Reactive with the Tumor-Associated Glycoprotein 72 Antigen," Cancer Research, Aug. 15, 1988, 48(16):4588-4596.

Zhu, et al., "Circulating cell-free DNA fragmentation is a stepwise and conserved process linked to apoptosis," BMC Biology, Nov. 13, 2023, 21(1): 1-11.

Addeo et al., "Measuring tumor mutation burden in cell-free DNA: advantages and limits," Translational Lung Cancer Research, Aug. 2019, 8(4):553-555.

Babayan et al., "Advances in liquid biopsy approaches for early detection and monitoring of cancer," Genome Medicine, Mar. 20, 2018, 10:21, 3 pages.

Gusnanto et al., "Estimating optimal window size for analysis of low-coverage next-generation sequence data," Bioinformatics, Jul. 1, 2014, 30(13):1823-1829.

Li et al., "HIVID: An efficient method to detect HBV integration using low coverage sequencing," Genomics, Oct. 2013, 102(4):338-344.

Li et al., "Mapping short DNA sequencing reads and calling variants using mapping quality score," Genome Res., Aug. 19, 2008, 18:1851-1858.

Rizvi et al., "Mutational landscape determines sensitivity to PD-1 blockade in non-small cell lung cancer," Science, Apr. 3, 2015, 348(6230):124-128.

Ulrich et al., "Cell-free DNA in oncology: gearing up for clinic," Annals of Laboratory Medicine, 2018, 38(1):1-8.

Fortner et al., "Correlates of circulating ovarian cancer early detection markers and their contribution to discrimination of early detection models: results from the EPIC cohort," Journal of Ovarian Research, Mar. 20, 2017, 10, 14 pages.

Holdenrieder et al., "Clinically Meaningful Use of Blood Tumor Markers in Oncology," BioMed Research International, Nov. 30, 2016, 2016(1):1-10.

Mizuno et al., "Clinical Utility of Tumor Markers," Open Journal of Pathology, Apr. 30, 2021, 11(2):38-57.

Molina et al., "Assessment of a Combined Panel of Six Serum Tumor Markers for Lung Cancer," American Journal of Respiratory and Critical Care Medicine, Feb. 15, 2016, 193(4):427-437.

Fang et al., "Practical stability assessment of whole-genome methylation sequencing of plasma cell-free DNA," Chinese Journal of Biotechnology, Dec. 25, 2019, 35(12):2284-2294 (with English Abstract).

Jiang et al., "Lengthening and shortening of plasma DNA in hepatocellular carcinoma patients," Proceedings of the National Academy of Sciences of the United States of America, Feb. 2, 2015, 112(11):E1317-E1325.

Shi et al., "Rare Germline Copy Number Variations and Disease Susceptibility in Familial Melanoma," Journal of Investigative Dermatology, Dec. 31, 2016, 136(12):2436-2443.

Wang et al., "Advances in the study of predictive markers of immunotherapy for non-small cell lung cancer based on PD-1/PD-L1 inhibitors," Modern Oncology, May 31, 2021, 29(10):1822-1825 (with English Abstract).

Zhu et al., "Recent Ex Vivo Gene Therapy through Genome Editing," Chinese Journal of Cell Biology, Apr. 2019, 41(4):573-582 (with English Abstract).

Iglewicz et al., "Outlier Labeling," How to Detect and Handle Outliers, Nov. 8, 1993, Chapter 3, pp. 9-17.

Luan et al., "A panel of seven protein tumour markers for effective and affordable multi-cancer early detection by artificial intelligence: a large-scale and multicentre case-control study," Eclinical Medicine, Jul. 15, 2023, 51(1):102041, 12 pages.

Tu et al., "A panel of seven protein tumor markers for multi-cancer early detection by artificial intelligence," Journal of Clinical Oncology, May 31, 2023, 41(1):3067.

Agnes et al. "Appraisal of Deep-Learning Techniques on Computer-Aided Lung Cancer Diagnosis with Computed Tomography Screening," Journal of Medical Physics, Jul. 20, 2020, 45(2):98-106.

Huang et al., "Applications of Support Vector Machine (SVM) Learning in Cancer Genomics," Cancer Genomics & Proteomics, Dec. 31, 2018, 15(31):41-51.

Killcoyne et al., "Genomic copy number predicts esophageal cancer years before transformation," Nature Medicine, Nov. 2020, 26(11):1726-1732.

Mouliere et al., "Enhanced detection of circulating tumor DNA by fragment size analysis," Science Translational Medicine, Nov. 7, 2018, 10(466):eaat4921, 28 pages.

Stieber et al., "National Academy of Clinical Biochemistry Guidelines for the Use of Tumor Markers in Lung Cancer," NACB: Practice Guidelines and Recommendations for Use of Tumor Markers in the Clinic Lung Cancer (Section 3P), Dec. 31, 2006, 29 pages.

(56) References Cited

OTHER PUBLICATIONS

Wojcik et al., "Pro-gastrin-releasing peptide (ProGRP) as a biomarker in small-cell lung cancer diagnosis, monitoring and evaluation of treatment response," Lung Cancer: Targets and Therapy, Dec. 28, 2017, 8:231-240.

* cited by examiner

FIG. 15
For a Known SNV: Ref base: A ; Alt base: C
Reference : GGTGGATCACAAGGTCAGGAGATCAAGACCATCCTGGCTAACACGGTGAA SEQ ID NO: 1
Ref_base_PE
readsA_1: TCACAAGGTCAGGAGATCAAGACCATC SEQ ID NO: 2
AAGGTCAGGAGATCAAGACCATCCTGGCTAA: readsA_2 (reverse complement) SEQ ID NO: 3
Alt_base_PE
readsD_1: TCACAAGGTCAGGCGATCAAGACCATC SEQ ID NO: 4
AAGGTCAGGCGATCAAGACCATCCTGGCTAA: readsD_2 (reverse complement) SEQ ID NO: 5
Other_PE
readsB_1: TCACAAGGTCAGGTGATCAAGACCATC SEQ ID NO: 6
AAGGTCAGGTGATCAAGACCATCCTGGCTAA: readsB_2 (reverse complement) SEQ ID NO: 7
Diff_PE
readsC_1: TCACAAGGTCAGGTGATCAAGACCATC SEQ ID NO: 8
AAGGTCAGGCGATCAAGACCATCCTGGCTAA: readsC_2 (reverse complement) SEQ ID NO: 9
Diff_SE
readsE_1: TCACAAGGTCAGGCGATCAAGACCATC SEQ ID NO: 10
AAGGTCAGGAGATCAAGTCCATCCTGGCTAA: readsE_2 (reverse complement) SEQ ID NO: 11

METHOD FOR PREDICTING CANCER RISK VALUE BASED ON MULTI-OMICS AND MULTIDIMENSIONAL PLASMA FEATURES AND ARTIFICIAL INTELLIGENCE

CLAIM OF PRIORITY

This application claims the benefit of Chinese Patent Application No. CN202011193149.8, filed on Oct. 30, 2020, Chinese Patent Application No. 202011197469.0, filed on Oct. 30, 2020, and Chinese Patent Application No. CN 202110687795.8, filed on Jun. 21, 2021. The entire contents of the foregoing applications are incorporated herein by reference.

TECHNICAL FIELD

The present disclosure relates to the field of bioinformatics. Specifically, the present application relates to a method, system, electronic device and computer-readable medium for predicting a probability that a sample to be tested is derived from a cancer patient based on multi-omics and multidimensional plasma features and artificial intelligence.

BACKGROUND

Gene copy-number aberration (CNA) is an important molecular mechanism of many human diseases such as cancers, genetic diseases, and cardiovascular diseases. CNA usually refers to a genomic structural variation of the DNA fragments with a length over 1 Kb in the genome, including microscopic and submicroscopic deletions, insertions, and duplications of DNA. A large number of studies have shown that CNA plays a key driving role in the occurrence and development of cancer. CNA may disrupt the genome through the deletion, insertion, and duplication of DNA fragments, and especially may disrupt important signaling pathways that control cell division and the normal expression of genes, so as to allow cells to acquire a karyotype that is more conducive to the growth of cancer, thereby resulting in the occurrence of cancer. CNA has been recognized as one of the ubiquitous features of cancer genomes. As for the common cancers, about 60% of non-small cell lung cancer, 60-80% of breast cancer, 70% of colorectal cancer, and 30% of prostate cancer have a karyotype deviating from diploid to different extents.

Many studies have indicated that circulating tumor DNA (ctDNA) fragments from tumor cells in the blood are shorter than normal cell-free DNA (cfDNA), and the size of cfDNA fragment can be assessed by sequencing from both ends. Meanwhile, the fragmentation pattern of cfDNA in the genome is significantly different between healthy subjects and cancer patients, and also different between different cancer types.

Recently, researchers at the Cancer Research Center of the University of Cambridge have used shallow whole-genome sequencing (sWGS) from cfDNA to assess genome-wide CNA, and also have explored and verified the application prospects of cfDNA-based sWGS in early cancer screening and recurrence monitoring in combination with the in vitro/in silico cfDNA fragment size selection method. Researchers at the Kimmel Cancer Center of Johns Hopkins University have also developed a simple novel blood test method, DELFI, which can distinguish healthy subjects from cancer patients by analyzing cfDNA fragment size.

The current standard-of-care (SOC) cancer screening modalities including imaging, plasma tumor markers as well as cytology are basically restricted to particular cancer types and have unsatisfactory accuracy and participant's compliance. Copy-number aberrations and fragmentation pattern of cfDNA can be utilized for cancer early detection, recurrence monitoring, treatment response assessment as well as mechanistic study of the cause of individual cancers.

SUMMARY

The present disclosure solves one of the technical problems in the related field. In this regard, the present disclosure provides a non-invasive method for cancer detection, recurrence monitoring and treatment response assessment based on multidimensional characteristics of cell-free DNA (cfDNA) and protein markers in plasma and artificial intelligence, based on a technical route of cancer genome panorama in combination with tumor markers. This technology is based on the next-generation sequencing technology, and employs the method of shallow whole-genome sequencing (sWGS) to map the changes of the cancer genome panorama in the cfDNA of the sample to be tested. At the same time, in combination with specific protein tumor markers as well as big data and artificial intelligence, it can predict a probability that the sample to be tested is derived from a cancer patient. Based on multiple features (including chromosomal instability index, fragment size, protein marker content, mitochondrial DNA ratio, fragment size difference between SNV and SNP, tumor mutation burden as well as the cfDNA concentration) of the sample to be tested, the present disclosure employs a multidimensional and multivariable weighting algorithm and combines genomic markers and protein tumor markers, such that the probability that the sample to be tested is derived from a cancer patient can be predicted in a more sensitive and specific manner under the premise of more controllable testing costs. Compared with targeted capturing panel-based technology, this detection method covers a wider area of the genome in a more cost-effective fashion.

Thus, one aspect of the present disclosure provides a method for cancer detection, recurrence monitoring and treatment response assessment of a sample to be tested. According to an embodiment of the present disclosure, the method includes one or more of the following steps:

- a step (1) of obtaining a chromosome instability index in the sample to be tested;
- a step (2) of determining a probability that the sample to be tested is derived from a cancer patient based on a fragment size;
- a step (3) of determining a probability that the sample to be tested is derived from a cancer patient based on the concentration of a panel of protein tumor markers from the sample to be tested;
- a step (4) of obtaining a proportion of mitochondrial DNA reads (e.g., among all sequence reads) in the sample to be tested;
- a step (5) of obtaining a concentration of cfDNA in the sample to be tested;
- a step (6) of obtaining a fragment size difference between SNV and SNP (e.g., the max difference of cumulative distribution of the fragment size for reads with SNV and SNP mutations) and tumor mutation burden; and
- a step (7) of performing standardized transformations of quantitative values resulted in the steps (1) to (6), weighting the contribution of each standardized value in predicting the probability of having cancer, and determining a ultimate probability value that the sample to be tested is derived from a cancer patient.

It has been determined that, whether the sample to be tested is derived from a tumor sample or a healthy sample can be better distinguished by considering the insert distribution of P100, as well as P150, P180, P250, the peak-to-valley spacing and the fragment length corresponding to a peak value in an fragment size distribution, and by calculating the ratio of short fragments (100 to 150 bp) to long fragments (151 to 220 bp) in each bin, thereby providing novel insights for scientific research into the molecular mechanisms underlying the fragmentation pattern as well as providing a basis for clinical cancer diagnosis. In addition, the present disclosure shows that the amount of mitochondrial DNA is much higher in tumor samples than in healthy samples, and in some cancers (e.g., hepatocellular carcinoma) the difference is more significant among the mitochondrial DNA fragments below 150 bp. Therefore, proportion of the mitochondrial DNA fragments (e.g., below 150 bp) in the sample to be tested can be utilized to better distinguish whether it is derived from a cancer patient or a healthy subject. In the meantime, the cfDNA concentration of cancer patients is found to be significantly higher than that of healthy subjects. Thus, the cfDNA concentration can also be utilized to distinguish whether the sample to be tested is derived from a cancer patient or a healthy subject. the fragment size of reads supporting SNV mutation is significant shorter than that supporting SNP and tumor mutation burden The present disclosure adopts a cfDNA shallow whole-genome sequencing and plasma tumor marker methodological approach, and builds up a multivariate prediction model by means of machine learning, in order to predict whether the sample to be tested is derived from a cancer patient or a healthy subject. The method/model provided by the present disclosure uses one or more (e.g., 1, 2, 3, 4, 5, 6, or 7) indicators: copy number aberration (CNA), fragment size (FS), and protein tumor markers (PTMs), a proportion of mitochondrial DNA fragments below 150 bp, the concentration of cfDNA in plasma, fragment size difference between SNV and SNP, tumor mutation burden, for predicting the probability that the sample to be tested is derived from a cancer patient. Moreover, the same method/model provided by the present disclosure can also be implemented in clinical settings other than cancer detection, such as cancer recurrence monitoring and treatment response assessment. All of these quantitative indicators are standardized, transformed, and weighted by their contribution in predicting cancer, and an ultimate probability value that the sample to be tested is derived from a cancer patient can be obtained. In this way, the probability of having cancer from the sample to be tested can be predicted with higher sensitivity and specificity under the premise of more controllable testing costs. The method of the present disclosure predicts the probability that the sample to be tested is derived from a cancer patient, thereby providing meaningful insights for scientific and clinical research. For example, in the research of drug screening for cancer therapeutics or exploring the molecular basis of tumorigenesis in individuals, the probability that the sample to be tested is derived from a cancer patient can be determined before and after administration of the candidate anti-tumor drugs or other interventional therapy, so as to screen efficacious anti-tumor therapeutics. Moreover, the probability that the sample to be tested is derived from a cancer sample is obtained by using the method of the embodiments of the present disclosure, so as to provide an index for cancer detection.

The method for cancer detection, recurrence monitoring and treatment response assessment of the sample to be tested according to the embodiments of the present disclosure may also have at least one of the following additional technical features.

In an embodiment of the present disclosure, an artificial intelligence and/or statistical methods (e.g., logistic regression, random forest or Gradient Boosting Regression Tree) for obtaining a probability that the sample to be tested is derived from a cancer patient.

In some embodiments, the algorithm for the logistic regression is expressed in the following calculation formula:

$$P = \frac{1}{1 + e^{-(\alpha+\beta_1 * x_1+\beta_2 * x_2+\beta_3 * x_3+\beta_4 * x_4+\beta_5 * x_5+\beta_6 * x_6+\beta_7 * x_7)}}$$

In some embodiments, $x_1$ represents the chromosome instability index;

$x_2$ represents the probability that the sample to be tested is derived from a cancer patient determined based on the fragment size;

$x_3$ represents the probability that the sample to be tested is derived from a cancer patient determined based on the protein tumor marker content;

$x_4$ represents the proportion of mitochondrial DNA reads among all reads;

$x_5$ represents the plasma cfDNA concentration;

$x_6$ represents tumor mutation burden;

$x_7$ represents the fragment size difference between SNV and SNP; and

α is a constant, β1, β2, β3, β4, β5, β6, β7 are regression coefficients predicted by logistic regression.

In some embodiments, the algorithm for the logistic regression is expressed in the following calculation formula:

$$P = \frac{1}{1 + e^{-(\alpha+\beta_1 * x_1+\beta_2 * x_2+\beta_3 * x_3+\beta_4 * x_4+\beta_5 * x_5)}}$$

wherein $x_1$ represents the chromosome instability index (i.e., the number of CNA regions);

$x_2$ represents the probability that the sample to be tested is derived from a cancer patient determined based on the fragment size;

$x_3$ represents the probability that the sample to be tested is derived from a cancer patient determined based on the protein tumor marker content;

$x_4$ represents the proportion of mitochondrial DNA fragments (e.g. below 150 bp) among all reads;

$x_5$ represents the plasma cfDNA concentration;

α is a constant, β1, β2, β3, β4, and β5 are regression coefficients predicted by machine learning logistic regression.

In an embodiment of the present disclosure, a cut-off value corresponding to a specificity of 98% can be selected as a threshold for cancer detection, recurrence monitoring and treatment response assessment of the sample to be tested. If the value of the sample to be tested is greater than the threshold, it is predicted that the sample to be tested is derived from a cancer patient.

In an embodiment of the present disclosure, the probability that the sample to be tested is derived from a cancer patient is determined based on the fragment size by the following steps:

(2-1) obtaining the cfDNA sample from the sample to be tested;

(2-2) constructing a sequencing library based on the cfDNA sample;

(2-3) sequencing the sequencing library to obtain a sequencing result, the sequencing result consisting of a plurality of sequencing reads;

(2-4) statistically analyzing P100, P150, P180, P250, a peak-to-valley spacing, and/or a fragment length corresponding to a peak value in an insert length distribution based on the plurality of sequencing reads; or statistically analyzing P150, P180, P250, a peak-to-valley spacing, and/or a fragment length corresponding to a peak value in an insert length distribution based on the plurality of sequencing reads;

(2-5) obtaining the genome-wide fragmentation pattern of the sample to be tested based on sequencing reads in a sequencing result, and a ratio of the numbers of the sequencing reads in different predetermined insert length ranges in different chromosomal regions, and calculating a sum of deviations; and (2-6) modeling the results obtained in (2-4) and (2-5) by means of machine learning, and generating a probability value of the sample to be tested derived from cancer based on a modeling result, wherein P100 refers to a ratio of the number of inserts of 30-100 bp to the total number of inserts in the sample;

wherein P150 refers to a ratio of the number of inserts of 30-150 bp to the total number of inserts in the sample;

P180 refers to a ratio of the number of inserts of 180-220 bp to the total number of inserts in the sample;

P250 refers to a ratio of the number of inserts of 250-300 bp to the total number of inserts in the sample;

the peak-to-valley spacing refers to a difference between a ratio of a peak and a ratio of a valley adjacent to the peak, wherein the peak and the valley are observed in a size distribution of cfDNA samples shallow WGS data in a range of insert length smaller than 150 bp; a position of the peak corresponds an insert length of x, the ratio of the peak is calculated by dividing the number of reads in [x−2, x+2] by the total number of reads; a position of the valley corresponds an insert length of y, the ratio of the valley is calculated by dividing the number of reads in [y−2, y+2] by the total number of reads; and the fragment length corresponding to the peak value in the insert length distribution is a fragment length corresponding to the most abundant sequencing reads based on the number of sequencing reads corresponding to different insert lengths of a sample.

It can be better distinguished whether the sample to be tested is derived from a cancer patient or a healthy subject by considering the insert distribution of P100, as well as P150, P180, P250, the peak-to-valley spacing and the fragment length corresponding to a peak value in an insert length distribution, and by calculating the absolute value of the ratio of short fragments (100 to 150 bp) to long fragments (151 to 220 bp) in each bin, thereby providing insights for scientific research or providing a basis for clinical cancer diagnosis.

In an embodiment of the present disclosure, in step (2-5), the ratio of the numbers of the sequencing reads of inserts in different predetermined length ranges in different chromosomal regions is obtained by the following steps:

a) dividing a human reference genome evenly into non-overlapping bins, optionally, each of the plurality of window bins having a size of 100 kb;

b) determining the sequencing reads numbers within predetermined inserts length ranges in each bins, optionally, the different predetermined insert length ranges are 100-150 bp and 151-220 bp; and c) determining a ratio of the numbers of sequencing reads in different predetermined insert length ranges in each bins.

In an embodiment of the present disclosure, the number of sequencing reads within predetermined insert length ranges in each bins is further subjected to a correction processing.

In an embodiment of the present disclosure, in each bins, the correction processing is performed by adding a fragment number residual error to a median value of the numbers of sequencing reads within predetermined insert length ranges in all the bins. In an embodiment of the present disclosure, the fragment number residual error is obtained by the following steps:

(i) determining the GC content and the mappability in each bin;

(ii) combining and grouping the GC content and the mappability in each of the plurality of window bins obtained in step (i), and obtaining a median value of the numbers of sequencing reads within predetermined insert length range in the bins corresponding to each combination of the GC content and the mappability;

(iii) based on a locally weighted non-parametric regression method, constructing a fitted curve of the median value (step ii) corresponding to each combination of the GC content and the mappability with respect to the GC content and mappability;

(iv) determining the theoretical sequencing reads number within predetermined insert length range in each bin based on the fitted curve and the GC content and mappability in each of the plurality of window bins; and (v) subtracting the theoretical value obtained in step (iv) from the number of sequencing reads within predetermined insert length in each bins, to obtain a residual error of the number of sequencing reads within predetermined insert length in each bins.

In an embodiment of the present disclosure, the sum of deviations is calculated by summing up absolute values of a ratio of the sums of the numbers of reads of inserts minus a median value of all ratios of the sums of the numbers of reads of inserts, according to the following formula:

$$\Sigma \text{abs}(S_i/L\text{-median}(S_1/L_1, S_2/L_2, \ldots, S_n/L_n));$$

wherein S represents an insert of 100-150 bp, L represents an insert of 151-220 bp, abs( ) denotes calculating an absolute value of values in the parentheses, median( ) denotes calculating median value of values in the parentheses, i represents a genomic region in human genome, and n is the total number of bins.

In an embodiment of the present disclosure, the ratio of the sums of the numbers of reads of inserts is obtained by the following steps:

1) calculating a sum of the numbers of reads within predetermined insert length ranges in one predetermined bin, which comprises: in the one predetermined bin, calculating a sum of the numbers of reads in a length range of 100 to 150 bp, and calculating a sum of the numbers of reads in a length range of 151 to 220 bp;

optionally, after the summing up, the bin has a length of 5M; and 2) dividing the sum of the numbers of reads of inserts in a length range of 100 to 150 bp by the sum of the numbers of reads of inserts in a length range of 151 to 220 bp, to obtain the ratio of the sums of the numbers of reads of inserts.

In an embodiment of the present disclosure, the machine learning model is selected from at least one of SVM (support vector machine), LASSO (least absolute shrinkage and selection operator), or GBM (Gradient Boosting Machine);

optionally, a model established by the machine learning is LASSO, and a corresponding threshold is determined based on a ROC curve and a predetermined sensitivity or specificity; and optionally, the predetermined specificity is 95%, and the threshold is 0.40.

In an embodiment of the present disclosure, the proportion of mitochondrial DNA reads in the sample to be test is determined by the following steps: determining the number of sequencing reads aligned to a reference mitochondrial gene sequence; and divide these sequencing reads by the total number of sequence reads.

The difference between healthy samples and tumor samples can be significant among the mitochondrial DNA. Therefore, by exploiting the proportion of the mitochondrial DNA in the sample to be tested, it can be better distinguished whether the sample to be tested is derived from a tumor sample or a healthy sample. In some embodiments, the tested the mitochondrial DNA fragments is below 150 bp.

In an embodiment of the present disclosure, the sample to be tested is derived from a patient who is suspected to have cancer.

In an embodiment of the present disclosure, the sample to be tested is blood, body fluid, urine, saliva or skin.

Another aspect of the present disclosure provides a method for longitudinal monitoring the probability of cancer from a sample to be tested. In an embodiment of the present disclosure, the method includes: selecting a sample to be tested from a patient suspected of having cancer at different time points; and predicting the probability of have cancer from the sample to be tested using said method for cancer detection, recurrence monitoring and treatment response assessment of a sample to be tested.

In the research of drug screening for treating cancer or exploring the cause of cancer in individuals, the determined probability that the sample to be tested is derived from a cancer patient can indicate the molecular tumor burden in a real-time fashion, so it may be utilized to assess the treatment response of a patient towards certain anti-cancer candidate drugs. Moreover, the probability that the sample to be tested is derived from a cancer patient with the method of the present disclosure may also be able to assess cancer recurrence after a patient received radical resection.

Yet another aspect of the present disclosure provides an electronic device for cancer detection, recurrence monitoring and treatment response assessment of a sample to be tested. In an embodiment of the present disclosure, the electronic device for cancer detection, recurrence monitoring and treatment response assessment of a sample to be tested includes a memory and a processor.

The processor is configured to read an executable program code stored in the memory and to execute a program corresponding to the executable program code, to perform said method for cancer detection, recurrence monitoring and treatment response assessment of a sample to be tested.

Yet another aspect of the present disclosure provides a computer-readable storage medium. In an embodiment of the present disclosure, the computer-readable storage medium is configured to store a computer program, and the computer program is configured to, when executed by a processor, perform said method for cancer detection, recurrence monitoring and treatment response assessment of a sample to be tested.

Yet another aspect of the present disclosure provides a system for cancer detection, recurrence monitoring and treatment response assessment of a sample to be tested. In an embodiment of the present disclosure, the system includes:

a chromosome instability index measuring device configured to measure a chromosome instability index of the sample to be tested;

a fragment size measuring device configured to determine a probability that the sample to be tested is derived from a cancer patient based on a fragment size;

a protein marker content measuring device configured to determine a probability that the test sample is derived from a cancer patient based on a protein tumor marker content of the test sample;

a mitochondrial DNA fragment measuring device configured to determine a proportion of mitochondrial fragments in the sample to be tested;

a plasma cfDNA concentration measuring device configured to measure a plasma cfDNA concentration of the sample to be tested;

a sample mutation burden measuring device configured to measure average single nucleotide mutation number per megabase (M);

a fragment size difference measuring device configured to measure fragment size between SNV and SNP;

a standardization processing device, wherein the standardization processing device is connected to the chromosome instability index measuring device, the fragment size measuring device, the protein marker content measuring device, the mitochondrial DNA fragment measuring device and the plasma cfDNA concentration measuring device, the sample mutation burden measuring device, the fragment size difference measuring device; and the standardization processing device is configured to perform standardization processing of the obtained chromosome instability index of the sample to be tested, the probability that the sample to be tested is derived from a cancer patient determined based on the fragment size, the probability that the sample to be tested is derived from a cancer patient determined based on the protein tumor marker content of the test sample, the proportion of mitochondrial DNA fragments, the plasma cfDNA concentration, the sample mutation burden, the fragment size difference between SNV and SNP; and a determination device, wherein the determination device is connected to the standardization processing device, and configured to determine the probability that the sample to be tested is derived from a cancer patient based on the standardization-processed sample data obtained by the standardization processing device and a prediction model.

In some embodiments, the system for cancer detection, recurrence monitoring and treatment response assessment of a sample to be tested further includes at least one of the following additional features.

In an embodiment of the present disclosure, an artificial intelligence method or statistical method (e.g., logistic regression, random forest or Gradient Boosting Regression Tree for obtaining a probability that the sample to be tested is derived from a cancer patient) is used.

In some embodiments, an algorithm for obtaining a score indicating the likelihood that the subject has a cancer or the probability that the sample to be tested is derived from a cancer patient in the determination device is expressed in the following calculation formula:

$$P = \frac{1}{1 + e^{-(\alpha+\beta_1*x_1+\beta_2*x_2+\beta_3*x_3+\beta_4*x_4+\beta_5*x_5)}}$$

wherein $x_1$ represents the chromosome instability index;

$x_2$ represents the probability that the sample to be tested is derived from a cancer patient determined based on the fragment size;

$x_3$ represents the probability that the sample to be tested is derived from a cancer patient determined based on the protein tumor marker content;

$x_4$ represents the proportion of mitochondrial DNA fragments (e.g., below 150 bp) among all reads;

$x_5$ represents the plasma cfDNA concentration; and

α is a constant, β1, β2, β3, β4, and β5 are regression coefficients predicted by machine learning logistic regression.

In some embodiments, the algorithm for the logistic regression is expressed in the following calculation formula:

$$P = \frac{1}{1 + e^{-(\alpha+\beta_1*x_1+\beta_2*x_2+\beta_3*x_3+\beta_4*x_4+\beta_5*x_5+\beta_6*x_6+\beta_7*x_7)}}$$

In some embodiments, $x_1$ represents the chromosome instability index;

$x_2$ represents the probability that the sample to be tested is derived from a cancer patient determined based on the fragment size;

$x_3$ represents the probability that the sample to be tested is derived from a cancer patient determined based on the protein tumor marker content;

$x_4$ represents the proportion of mitochondrial DNA reads among all reads;

$x_5$ represents the plasma cfDNA concentration;

$x_6$ represents tumor mutation burden;

$x_7$ represents the fragment size difference between SNV and SNP; and

α is a constant, β1, β2, β3, β4, β5, β6, β7 are regression coefficients predicted by logistic regression.

In some embodiments, the system further includes a prediction model obtaining device. The prediction model obtaining device is configured to obtain the prediction model by the following steps:

determining a chromosomal instability index, a fragment size, a tumor protein content, a proportion of mitochondrial DNA and a plasma cfDNA content of a known type of sample to obtain the chromosomal instability index, the fragment size, the tumor protein content, the proportion of mitochondrial DNA the plasma cfDNA content of the known type of sample, the sample mutation burden of the known type of sample, the fragment size difference between SNV and SNP of the known type of sample, and wherein the known type of sample is composed of a known number of healthy samples and a known number of tumor samples;

standardization processing the data of the known type of sample to obtain a standard deviation and a variance of the data of the known type of sample, the data comprising the chromosome instability index, the fragment size, the tumor protein content, the proportion of mitochondrial DNA with insert size below 150 bp, and the plasma cfDNA concentration.

In some embodiments, the prediction model further involves determining a prediction effect, variance and bias of the machine learning model by using a machine learning model: and a 10-fold cross-validation method.

In some embodiments, the prediction model further involves determining the prediction model based on the prediction effect, variance and bias of the machine learning model.

Preferably, the machine learning model is selected from at least one of SVM, LASSO, or GBM.

In some embodiments, the fragment size measuring device determines the probability that the sample to be tested is derived from a cancer patient based on the fragment size by the following steps:

(2-1) obtaining a cfDNA sample from the sample to be tested;

(2-2) constructing a sequencing library based on the cfDNA sample;

(2-3) sequencing the sequencing library to obtain a sequencing result, the sequencing result consisting of a plurality of sequencing reads;

(2-4) statistically analyzing P100, P180, P250, a peak-to-valley spacing, and optionally a fragment length corresponding to a peak value in an fragment size distribution based on the plurality of sequencing reads; or statistically analyzing P150, P180, P250, a peak-to-valley spacing;

(2-5) obtaining a genome of the sample to be tested, constructing a sequencing library and sequencing to obtain, based on sequencing reads in a sequencing result, a ratio of the numbers of the sequencing reads of insert size in different predetermined length ranges in different chromosomal regions, and calculating a sum of deviation; and (2-6) modeling the results obtained in (2-4) and (2-5) by means of machine learning, and predicting the probability of the test sample from cancer based on a modeling result, wherein P100 refers to a ratio of the number of inserts of 30-100 bp to the total number of inserts in the sample;

wherein P150 refers to a ratio of the number of inserts of 30-150 bp to the total number of inserts in the sample;

P180 refers to a ratio of the number of inserts of 180-220 bp to the total number of inserts in the sample;

P250 refers to a ratio of the number of inserts of 250-300 bp to the total number of inserts in the sample;

the peak-to-valley spacing refers to a difference between a ratio of a peak and a ratio of a valley adjacent to the peak, wherein the peak and the valley are observed in a insert size distribution of cfDNA samples shallow-WGS data in a range of insert length smaller than 150 bp; a position of the peak corresponds an insert length of x, the ratio of the peak is calculated by dividing the number of reads with insert length in [x−2, x+2] by the total number of reads; a position of the valley corresponds an insert length of y, the ratio of the valley is calculated by dividing the number of reads with insert length in [y−2, y+2] by the total number of reads; and the fragment length corresponding to the peak value in the insert length distribution is a fragment length corresponding to the most abundant sequencing reads based on the number of sequencing reads corresponding to different insert lengths of a sample.

In some embodiments, in step (2-5), the ratio of the sequencing reads numbers with different predetermined insert length ranges in different chromosomal regions is obtained by the following steps:

a) dividing a human reference genome evenly into non-overlapping bins, optionally, each of the bins having a size of 100 kb;

b) determining the numbers of sequencing reads with different predetermined insert length ranges in each bins, optionally, the different predetermined length ranges are 100-150 bp and 151-220 bp; and c) determining a ratio of sequencing reads number within different predetermined insert length ranges in each bins.

Optionally, the number of sequencing reads within predetermined insert length ranges in each bins is further subjected to a correction processing.

In each bins, the correction processing is performed by adding a fragment number residual error to a median value of the numbers of sequencing reads within predetermined insert length ranges in each bins.

The fragment number residual error is obtained by the following steps:

(i) determining the GC content and the mappability in each o bins;

(ii) combining and grouping the GC content and the mappability in each bins obtained in step (i), and obtaining a median value of the numbers of sequencing reads in bins corresponding to each combination of the GC content and the mappability;

(iii) based on a locally weighted non-parametric regression method, constructing a fitted curve of the median value of the numbers of sequencing reads within predetermined insert length ranges to each combination of the GC content and the mappability with respect to the GC content and mappability;

(iv) determining the theoretical number of sequencing reads in each bins based on the fitted curve and the GC content and mappability in each bins; and (v) subtracting the theoretical number of sequencing reads obtained in step (iv) from the number of sequencing reads within predetermined molecular length in each bins, to obtain a residual error of the number of sequencing reads with predetermined insert length in each bins.

In some embodiments, the sum of deviations is calculated by summing up absolute ratio of the total reads number among different predetermined insert length range minus a median value of all ratios in each bins, according to the following formula:

$$\Sigma \mathrm{abs}(S_i/L\text{-}\mathrm{median}(S_1/L_1, S_2/L_2, \ldots, S_n/L_n));$$

wherein S represents the sequencing reads number with short insert length (100-150 bp) in one bins, L represents the sequencing reads number with long insert length (151-220 bp), abs( ) denotes calculating an absolute value in the parentheses, median( ) denotes calculating median value in the parentheses, i represents a genomic region in human genome, and n is the total number of bins.

The ratio of the S to L obtained by the following steps:

1) calculating a sum of reads number within predetermined insert length ranges in one new predetermined bin, which comprises: in one new predetermined bin, calculating a sum of the reads numbers with inserts in a length range of 100 to 150 bp, and calculating a sum of the reads number with inserts in a length range of 151 to 220 bp;

optionally, after the summing up, the length of bin is 5M; and 2) dividing the sum of the numbers of reads of inserts in a length range of 100 to 150 bp by the sum of the numbers of reads of inserts in a length range of 151 to 220 bp, to obtain the ratio of S to L in each 5M bins.

Optionally, the machine learning model is selected from at least one of SVM, LASSO, or GBM.

Optionally, a model established by the machine learning is LASSO, and a corresponding threshold is determined based on a ROC curve and a predetermined sensitivity or specificity.

Optionally, the predetermined specificity is 98%, and the threshold is 0.40.

In some embodiments, the proportion of mitochondrial DNA is determined by the following steps:

determining the number of sequencing reads aligned to a reference mitochondrial genome sequence and divide mitochondrial DNA reads by the total number of sequence reads.

In some embodiments, the sample to be tested is derived from a patient suspected of having cancer.

Optionally, the sample to be tested is blood, body fluid, urine, saliva or skin.

In one aspect, the disclosure provides a method for detecting a cancer in a subject, the method comprising:

(a) providing a sample from the subject comprising cfDNA;

(b) detecting one or more single nucleotide variants in the cfDNA by the method as described herein.

(c) counting the single nucleotide variants in the cfDNA in the sample from the subject, thereby determining the tumor mutation burden in the subject;

(d) determining that tumor mutation burden is more than a reference mutation burden; and (e) determining that the subject has a cancer.

In some embodiments, the reference mutation burden is an average mutation burden of a group of subjects that do not have cancer.

In some embodiments, the tumor mutation burden is at least 5, 10, 50, 100, 500, or 1000 times greater than the reference mutation burden.

In one aspect, the disclosure provides a method for detecting a cancer in a subject, the method comprising:

(a) providing a sample from the subject comprising cfDNA;

(b) determining probabilities of one or more single nucleotide variants in the cfDNA by the method as described herein;

(c) determining the sum of the probabilities of the one or more single nucleotide variants in the cfDNA in the sample from the subject, thereby determining the tumor mutation burden in the subject;

(d) determining that tumor mutation burden is more than a reference mutation burden; and (e) determining that the subject has a cancer.

In some embodiments, the reference mutation burden is the average of the sum of the probabilities of single nucleotide variants in the cfDNA in a group of subjects that do not have cancer.

In some embodiments, the tumor mutation burden is at least 5, 10, 50, 100, 500, or 1000 times greater than the reference mutation burden.

In some embodiments, the method further comprises administering a treatment for cancer to the subject. In some embodiments, the subject is administered with a chemotherapy.

In some embodiments, the subject is administered with an immunotherapy.

Additional aspects and advantages of the present disclosure will be partly provided in the following description, and parts of them will become obvious from the following description or can be understood through the practice of the present disclosure.

BRIEF DESCRIPTION OF DRAWINGS

The above and/or additional aspects of the present disclosure and advantages will become obvious and easy to understand from the description of embodiments in conjunction with the following drawings, in which.

SEQUENCE LISTING

This application contains a Sequence Listing that has been submitted electronically as an ASCII text file named "46708-0005001Sequence.txt". The ASCII text file, created on Oct. 20, 2021, is 2564 bytes in size. The material in the ASCII text file is hereby incorporated by reference in its entirety.

DETAILED DESCRIPTION

The present application adopts a cfDNA shallow whole-genome sequencing and plasma tumor marker detection, and constructs a multivariate prediction model by means of machine learning, in order to distinguish whether the sample to be tested is derived from a tumor sample or a healthy sample. The method/model provided by the present application for predicting the source of the sample to be tested uses one or more (e.g., 1, 2, 3, 4, 5, 6, 7) indicators as described herein. These indicators include e.g., a concentration of cfDNA in plasma, gene copy number aberration, fragment size, protein tumor markers, and the proportion of mitochondrial, sample mutation burden, and/or fragment difference between SNV and SNP. All of these quantitative indicators can be standardized and transformed, to build the model by machine learning to predict cancer, the probability that the test sample is derived from a cancer patient can be obtained. In this way, the source of the sample to be tested can be more sensitively and specifically predicted under the premise of more controllable testing costs.

Cancer Risk Value

Figure 1:
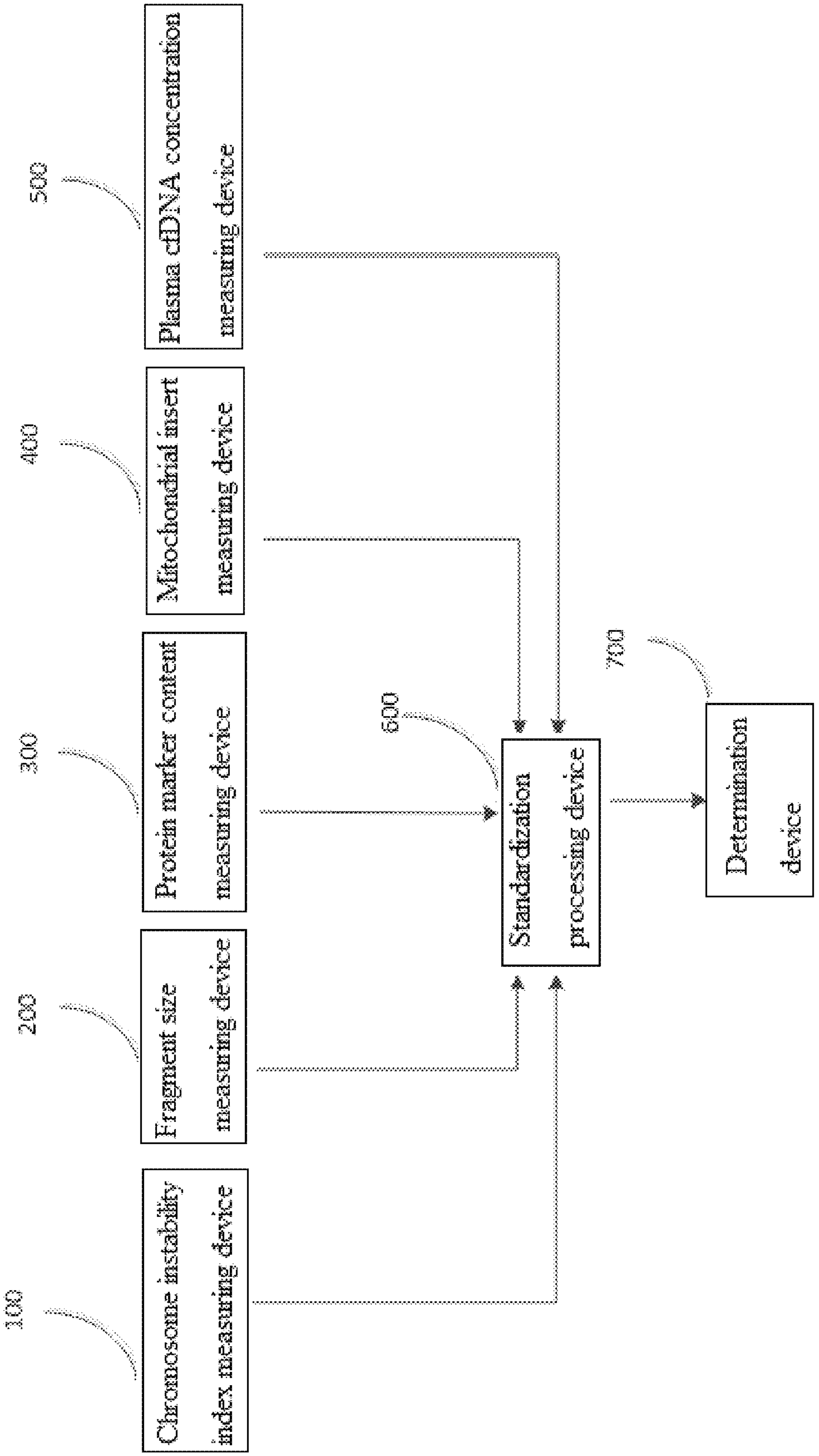
FIG. 1 shows a flowchart of a method for cancer detection, recurrence monitoring and treatment response assessment of a sample according to an embodiment of the present disclosure.

For the convenience of description, FIG. 1 shows a structural diagram of a system for cancer detection, recurrence monitoring and treatment response assessment of a sample to be tested as proposed in the present disclosure. According to an embodiment of the present disclosure, the system includes one or more of the following:

- a chromosome instability index measuring device 100, which is configured to determine a chromosome instability index of the sample to be tested;
- a fragment size measuring device 200, which is configured to determine a probability that the sample to be tested is derived from a cancer patient based on a fragment size;
- a protein marker content measuring device 300, which is configured to determine a probability that the test sample is derived from a cancer patient based on a protein tumor marker content of the test sample;
- a mitochondrial insert measuring device 400, which is configured to determine a proportion of mitochondrial DNA in the sample to be tested; in some embodiments, the mitochondrial DNA fragment is below 150 bp;

a plasma cfDNA concentration measuring device 500, which is configured to measure a plasma cfDNA concentration of the sample to be tested;

a standardization processing device 600, which is connected to the chromosome instability index measuring device 100, the fragment size measuring device 200, the protein marker content measuring device 300, the mitochondrial insert measuring device 400, the plasma cfDNA concentration measuring device 500, in order to perform standardization processing of the obtained chromosome instability index of the sample to be tested, the probability that the sample to be tested is derived from a cancer patient determined based on the fragment size, the probability that the sample to be tested is derived from a cancer patient determined based on the protein tumor marker content of the test sample, the proportion of mitochondrial DNA fragments below 150 bp, and the plasma cfDNA concentration; and a determination device 700, which is connected to the standardization processing device 600 and is configured to determine the probability that the sample to be tested is derived from a cancer patient based on the standardization-processed sample data obtained by the standardization processing device 600 and a prediction model.

In some embodiments, the system further includes a sample mutation burden measuring device configured to measure average single nucleotide mutation number per megabase (M); and/or a fragment size difference measuring device configured to measure fragment size between SNV and SNP. The standardization processing device 600 can be connected to the sample mutation burden measuring device and the fragment size difference measuring device and preform standardization processing on the sample mutation burden on the fragment size difference.

According to a specific embodiment of the present disclosure, an algorithm for said determining the probability that the sample to be tested is derived from a cancer patient in the determination device 700, which is machine learning model (random forest, logistic regression, Gradient Boosting Regression Tree. The logistic regression model is expressed in the following calculation formula:

$$P = \frac{1}{1 + e^{-(\alpha+\beta_1 * x_1+\beta_2 * x_2+\beta_3 * x_3+\beta_4 * x_4+\beta_5 * x_5+\beta_6 * x_6+\beta_7 * x_7)}}$$

In some embodiments, $x_1$ represents the chromosome instability index;

$x_2$ represents the probability that the sample to be tested is derived from a cancer patient determined based on the fragment size;

$x_3$ represents the probability that the sample to be tested is derived from a cancer patient determined based on the protein tumor marker content;

$x_4$ represents the proportion of mitochondrial DNA reads among all reads;

$x_5$ represents the plasma cfDNA concentration;

$x_6$ represents tumor mutation burden;

$x_7$ represents the fragment size difference between SNV and SNP; and

In some embodiments, the logistic regression model is expressed in the following formula:

$$P = \frac{1}{1 + e^{-(\alpha+\beta_1 * x_1+\beta_2 * x_2+\beta_3 * x_3+\beta_4 * x_4+\beta_5 * x_5)}}$$

wherein $x_1$ represents the chromosome instability index;

$x_2$ represents the probability that the sample to be tested is derived from a cancer patient determined based on the fragment size;

$x_3$ represents the probability that the sample to be tested is derived from a cancer patient determined based on the protein tumor marker content;

$x_4$ represents the proportion of mitochondrial DNA fragments (e.g., below 150 bp) among all reads;

$x_5$ represents the plasma cfDNA concentration; and

α is a constant, β1, β2, β3, β4, and β5 are regression coefficients predicted by machine learning logistic regression.

Figure 2:
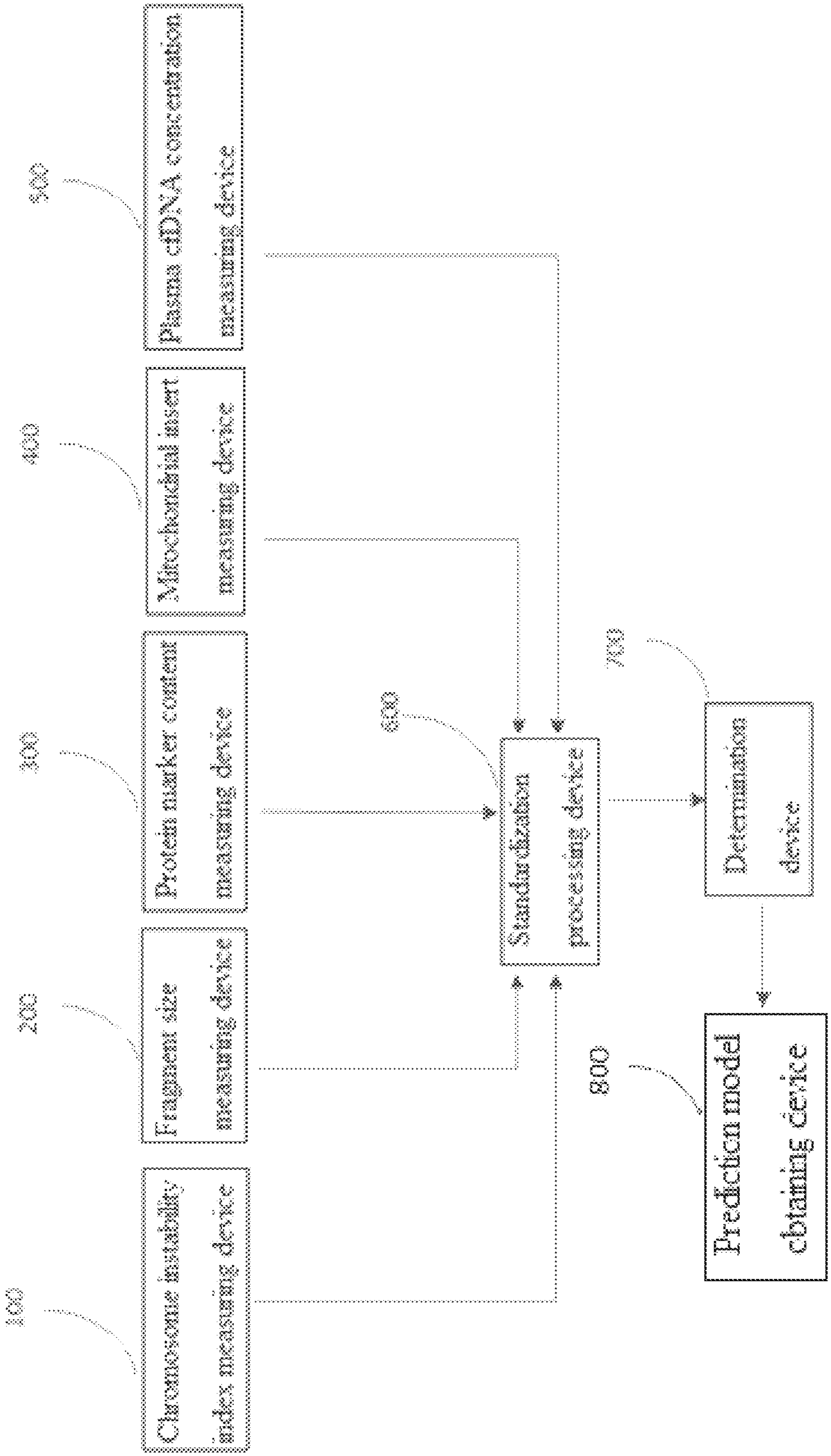
FIG. 2 shows a flowchart of a method for cancer detection, recurrence monitoring and treatment response assessment of a sample according to another embodiment of the present disclosure.

According to a specific embodiment of the present disclosure, referring to FIG. 2, the system further includes a prediction model obtaining device 800. The prediction model obtaining device 800 is connected to the determination device 700, and the prediction model obtaining device 800 is configured to obtain a prediction model as follows:

(M1) determining a chromosomal instability index, a fragment size, a tumor protein content, a plasma cfDNA content, and a proportion of mitochondrial DNA fragments of a known type of samples to obtain the chromosomal instability index, the fragment size, the tumor protein content, the plasma cfDNA content, the mutation burden and fragment difference between SNP and SNV, and the proportion of mitochondrial DNA fragments of the known type of sample, wherein the known type of samples is composed of a known number of healthy samples and a known number of tumor samples;

(M2) standardization processing the data of the known type of samples to obtain the standard deviation and variance of the data of the known type of samples, the data including the chromosome instability index, the fragment size, the tumor protein content, the proportion of mitochondrial DNA, and the plasma cfDNA concentration that are obtained in step (M1);

(M3) using a machine learning model and a 10-fold cross-validation method to determine the prediction effect, variance and bias of the machine learning model; and (M4) determining the prediction model based on the prediction effect, variance and bias of the machine learning model.

Preferably, the machine learning model is selected from at least one of SVM, Lasso, or GBM.

According to a specific embodiment of the present disclosure, the determination of the probability that the sample to be tested is derived from a cancer patient based on the fragment size with the fragment size measuring device 200 includes the following steps:

(2-1) obtaining a cfDNA sample from the sample to be tested;

(2-2) constructing a sequencing library based on the cfDNA sample;

(2-3) sequencing the sequencing library to obtain a sequencing result, the sequencing result consisting of a plurality of sequencing reads;

(2-4) statistically analyzing P100, P150, P180, P250, a peak-to-valley spacing, and a fragment length corresponding to a peak value in an insert length distribution based on the plurality of sequencing reads;

(2-5) obtaining a genome of the sample to be tested, constructing a sequencing library and sequencing to obtain, based on sequencing reads in a sequencing result, a ratio of the numbers of the sequencing reads of inserts in different predetermined length ranges in different chromosomal regions, and calculating a sum of deviations; and (2-6) modeling the results obtained in (2-4) and (2-5) by means of machine learning, and predicting a score of the source of the sample to be tested based on a modeling result, wherein P100 refers to a ratio of the number of inserts of 30-100 bp in the sample to the total number of inserts;

P150 refers to a ratio of the number of inserts of 30-150 bp in the sample to the total number of inserts;

P180 refers to a ratio of the number of inserts of 180-220 bp in the sample to the total number of inserts;

P250 refers to a ratio of the number of inserts of 250-300 bp in the sample to the total number of inserts;

the peak-to-valley spacing refers to a difference between a ratio of a peak and a ratio of a valley adjacent to the peak, wherein the peak and the valley are observed in a size distribution of cfDNA samples shallow WGS data in a range of insert length smaller than 150 bp; a position of the peak corresponds an insert length of x, the ratio of the peak is calculated by dividing the number of reads in [x−2, x+2] by the total number of reads; a position of the valley corresponds an insert length of y, the ratio of the valley is calculated by dividing the number of reads in [y−2, y+2] by the total number of reads; and the fragment length corresponding to the peak value in the insert length distribution is a fragment length corresponding to the most abundant sequencing reads based on the number of sequencing reads corresponding to different insert lengths of a statistical sample.

In some embodiments, in step (2-5), the ratio of the numbers of the sequencing reads of inserts in different predetermined length ranges in different chromosomal regions is obtained by the following steps:

a) dividing a human reference genome evenly into a plurality of window bins, optionally, each of the plurality of window bins having a size of 100 kb;

b) determining the numbers of sequencing reads of inserts in different predetermined length ranges in each of the plurality of window bins, optionally, the different predetermined length ranges are 100-150 bp and 151-220 bp; and c) determining a ratio of the numbers of sequencing reads of inserts in different predetermined length ranges in each of the plurality of window bins.

Optionally, the number of sequencing reads of inserts in predetermined length ranges in each of the plurality of window bins is further subjected to a correction processing.

In each of the plurality of window bins, the correction processing is performed by adding a fragment number residual error to a median value of the numbers of sequencing reads of inserts in predetermined length ranges in each of in the plurality of window bins.

The fragment number residual error is obtained by the following steps:

(i) determining a GC content and a mappability in each of the plurality of window bins;

(ii) combining and grouping the GC content and the mappability in each of the plurality of window bins obtained in step (i), and obtaining a median value of the numbers of sequencing reads in window bins corresponding to each combination of the GC content and the mappability;

(iii) constructing, based on a locally weighted non-parametric regression method (LOESS), a fitted curve of the median value of the numbers of sequencing reads in the window bins corresponding to each combination of the GC content and the mappability with respect to the GC content and mappability;

(iv) determining a theoretical number of inserts in each of the plurality of window bins based on the fitted curve and the GC content and mappability in each of the plurality of window bins; and (v) subtracting the theoretical number of inserts obtained in step (iv) from the number of sequencing reads of inserts of predetermined length in each of the plurality of window bins, to obtain a residual error of the number of inserts of predetermined length in each of the plurality of window bins.

In some embodiments, the sum of deviations is calculated by summing up absolute values of a ratio of the sums of the numbers of reads of inserts minus a median value of all ratios of the sums of the numbers of reads of inserts, according to the following formula:

$$\Sigma abs(S_1/L\text{-median}(S_1/L_1,S_2/L_2, \ldots ,S_n/L_n));$$

wherein S represents an insert of 100-150 bp, L represents an insert of 151-220 bp, abs( ) denotes calculating an absolute value of values in the parentheses, median( ) denotes calculating median value of values in the parentheses, i represents a genomic region in human genome, and n is the total number of bins.

The ratio of the sums of the numbers of reads of inserts is obtained by the following steps:

1) calculating a sum of the numbers of reads of inserts of predetermined length ranges in one predetermined bin, which comprises: in the one predetermined bin, calculating a sum of the numbers of reads of inserts in a length range of 100 to 150 bp, and calculating a sum of the numbers of reads of inserts in a length range of 151 to 220 bp;

optionally, after the summing up, the bin has a length of 5M; and 2) dividing the sum of the numbers of reads of inserts in a length range of 100 to 150 bp by the sum of the numbers of reads of inserts in a length range of 151 to 220 bp, to obtain the ratio of the sums of the numbers of reads of inserts.

Optionally, the machine learning model is selected from at least one of SVM, Lasso, or GBM.

Optionally, a model established by the machine learning is Lasso, and a corresponding threshold is determined based on a ROC curve and a predetermined sensitivity or specificity.

Optionally, the predetermined specificity is 95%, and the threshold is 0.40.

In some embodiments, the proportion of mitochondrial DNA in the sample to be test is determined by the following steps:

determining the number of sequencing reads aligned to a reference mitochondrial gene sequence and divide the number by the total number of sequencing reads.

The embodiments of the present disclosure are described in detail below. The embodiments described below are exemplary and are only intended to explain the present disclosure, but should not be construed as limitations of the present disclosure. Techniques or conditions that are not specifically indicated in the embodiments shall be carried out in accordance with the techniques or conditions known in the literatures in the related art or in accordance with the product instructions. Reagents or instruments used without indicating the manufacturers are all conventional products that are commercially available.

cfDNA Concentration

In one aspect, the disclosure is related to a method to predict cancer by determining the concentration of cfDNA (cell-free DNA) isolated (e.g., extracted using any of the methods described herein) from a sample (e.g., any of the tumor samples or healthy samples described herein). The method can include steps of separating plasma from the sample, followed by extraction of cfDNA from the plasma, and quantify the total amount of DNA, and calculate the cfDNA concentration.

In some embodiments, the concentration of cfDNA isolated from a subject is compared with that of a reference value (e.g., cfDNA concentration from a healthy subject or average cfDNA concentration of a group of healthy subjects). For example, if the concentration of cfDNA isolated from the subject is higher (e.g., at least 10%, at least 20%, at least 30%, at least 40%, at least 50%, at least 60%, at least 70%, at least 80%, at least 90%, or at least 1-fold higher) than that of the reference value, the subject is likely to have cancer. In some embodiments, a ROC curve can be made according to the cfDNA concentration, and the AUC value can be at least or about 0.65, at least or about 0.66, at least or about 0.67, at least or about 0.68, at least or about 0.69, at least or about 0.70, at least or about 0.71, at least or about 0.72, at least or about 0.73, at least or about 0.74, at least or about 0.75, at least or about 0.76, at least or about 0.77, at least or about 0.78, at least or about 0.79, at least or about 0.80.

Protein Marker Content

In one aspect, the disclosure is related to a method to predict cancer by determining the expression levels of one or more protein markers (e.g., any of the protein markers described herein) from a sample (e.g., any of the tumor samples or healthy samples described herein). In some embodiments, the one or more protein markers include carbohydrate antigen 15-3 (CA15-3); α-fetoprotein (AFP), carcinoembryonic antigen (CEA), carbohydrate antigen 19-9 (CA199), carbohydrate antigen 125 (CA125), cancer antigen 72-4 (CA72-4), human cytokeratin fragment antigen 21-1 (CYFRA21-1). In some embodiments, the determination process includes classification methods. In some embodiments, the classification methods can be Bayesian model, decision tree, support vector machine, neural network, or LASSO, etc. In some embodiments, the classification methods are used in connection with machine learning.

In some embodiments, the optimal parameter and cut-off value can be obtained by using the 10-fold cross-validation. In some embodiments, a score indicating the likelihood that the subject has cancer can be obtained. In some embodiments, the cut-off value for the score is about 90%, about 91%, about 92%, about 93%, about 94%, about 95%, about 96%, about 97%, about 98%, or about 99%. In some embodiments, a ROC curve can be made according to the score and/or the expression levels of the one or more protein markers, and the AUC value is at least or about 0.70, at least or about 0.71, at least or about 0.72, at least or about 0.73, at least or about 0.74, at least or about 0.75, at least or about 0.76, at least or about 0.77, at least or about 0.78, at least or about 0.79, at least or about 0.80.

Chromosomal Instability Index

In one aspect, the disclosure is related to a method to predict cancer by determining the chromosome instability index (CIN) value (or score) using any of the methods described herein.

In some embodiments, the chromosome instability index CIN score can be calculated based on the following formula:

$$CIN\ \text{score} = \sum_{k=1}^{n} Ri * \frac{lk}{a} * fk * \text{abs}(\log R)$$

$$R_i = \begin{Bmatrix} 1 & \text{abs}(Z - \text{score}) > 3 \\ 0 & \text{abs}(Z - \text{score}) \leq 3 \end{Bmatrix}$$

wherein n represents the number of all window;

a represents a predetermined constant, which is dependent on a size of the window;

$l_k$ represents a length of the k-th abnormal window;

$f_k$ represents a probability that CNV occurs in the k-th abnormal window sequence;

Z-score represents an absolute value of a standard score of the k-th window;

abs(log R) represents an absolute value of log R ratio of the k-th window after smoothing.

In some embodiments, the CIN score determined from a subject sample is compared with that of a reference value (e.g., the CIN score from a healthy subject) or is compared against the distribution of CIN scores of a group of healthy subjects. For example, if the CIN score is higher (e.g., at least 10%, at least 20%, at least 30%, at least 40%, at least 50%, at least 60%, at least 70%, at least 80%, at least 90%, at least 1-fold, at least 2-fold, at least 5-fold, or at least 10-fold higher) than that of the reference value, the subject is more likely to have cancer.

In some embodiments, a ROC curve can be made according to the CIN score, and the AUC value is at least or about 0.65, at least or about 0.66, at least or about 0.67, at least or about 0.68, at least or about 0.69, at least or about 0.70, at least or about 0.70, at least or about 0.71, at least or about 0.72, at least or about 0.73, at least or about 0.74, at least or about 0.75, at least or about 0.76, at least or about 0.77, at least or about 0.78, at least or about 0.79, at least or about 0.80.

Fragment Size

In one aspect, the disclosure is related to a method to predict cancer by determining the ratio of the number of inserts of 30-150 bp among the number of inserts of 30-300 bp, or P150. In some embodiments, the ratio of P150 determined from a subject sample is compared with that of a reference value (e.g., the ratio of P150 from a healthy sample). For example, if the ratio of P150 is higher (e.g., at least 10%, at least 20%, at least 30%, at least 40%, at least 50%, at least 60%, at least 70%, at least 80%, at least 90%, or at least 1-fold higher) than that of the reference value, the subject is likely to have cancer.

In one aspect, the disclosure is related to a method to predict cancer by determining the ratio of the number of inserts of 250-300 bp among the number of inserts of 30-300 bp, or P250. In some embodiments, the ratio of P250 determined from a subject sample is compared with that of a reference sample (e.g., the ratio of P250 from a healthy sample). For example, if the ratio of P250 is higher (e.g., at least 10%, at least 20%, at least 30%, at least 40%, at least 50%, at least 60%, at least 70%, at least 80%, at least 90%, or at least 1-fold higher) than that of the reference value, the subject is likely to have cancer.

In one aspect, the disclosure is related to a method to predict cancer by determining the peak-valley spacing. The peak is the length of reads with a local maximum number of sequencing reads. It typically corresponds to the insert lengths of about 81 bp, about 92 bp, about 102 bp, about 112 bp, about 122 bp, and/or about 134 bp. The peak is the length of reads with a local minimum number of sequencing reads. It typically corresponds to the insert lengths of about 84 bp, about 96 bp, about 106 bp, about 116 bp, about 126 bp, and/or about 137 bp. In some embodiments, the difference between a peak and the corresponding valley is determined. In some embodiments, the sum of the differences (e.g., amplitude) of 1, 2, 3, 4, 5, or 6 peak-valley pairs are determined. In some embodiments, the peak-valley spacing determined from a subject sample is compared with that of a reference value (e.g., the peak-valley spacing from a healthy sample). For example, if the peak-valley spacing is higher (e.g., at least 10%, at least 20%, at least 30%, at least 40%, at least 50%, at least 60%, at least 70%, at least 80%, at least 90%, or at least 1-fold higher) than that of the reference value, the subject is likely to have cancer.

In one aspect, the disclosure is related to a method to predict cancer by determining the sum of deviation. The sum of deviation is calculated by summing up absolute values of a ratio of the sums of the numbers of reads of inserts minus a median value of all ratios of the sums of the numbers of reads of inserts, according to the following formula:

$$\Sigma abs(S_1/L\text{-}median(S_1/L_1,S_2/L_2, \ldots ,S_n/L_n));$$

wherein S represents an insert of 100-150 bp, L represents an insert of 151-220 bp, abs( ) denotes calculating an absolute value of values in the parentheses, median( ) denotes calculating median value of values in the parentheses, i represents a genomic region in human genome, and n is the total number of bins. In some embodiments, the sum of deviation determined from a subject sample is compared with that of a reference value (e.g., the sum of deviation from a healthy subject). For example, if the sum of deviation is higher (e.g., at least 10%, at least 20%, at least 30%, at least 40%, at least 50%, at least 60%, at least 70%, at least 80%, at least 90%, or at least 1-fold higher) than that of the reference value, the subject is likely to have cancer.

In one aspect, the disclosure is related to a method to predict cancer by determining the highest peak value of sequencing reads. In some embodiments, the highest peak value described herein is 163, 164, 165, 166, 167, 168, 169, or 170. In some embodiments, the highest peak value determined from a subject sample is compared with that of a reference sample (e.g., the highest peak value from a healthy sample). For example, if the highest peak value is lower (e.g., e.g., less than 90%, less than 80%, less than 70%, less than 60%, or less than 50% lower, less than 40%, less than 30%, less than 20%, or less than 10%)) than that of the reference value, the subject is likely to have cancer.

In one aspect, the disclosure is related to a method to predict cancer and the method includes: determining ratios of the number of short fragments (e.g., the number of reads of inserts having a length ranging from 100 to 150 bp) divided by the number of long fragments (e.g., the number of reads of inserts having a length ranging from 151 to 220 bp) within one or more genome regions (e.g., one or more bins); calculating the median value of the ratios; and calculating the sum of the absolute value of the deviation of each bin from the median value. In some embodiments, the calculated sum described herein is compared with that of a reference value (e.g., the calculated sum from a healthy sample). For example, if the sum is higher (e.g., at least 10%, at least 20%, at least 30%, at least 40%, at least 50%, at least 60%, at least 70%, at least 80%, at least 90%, or at least 1-fold higher) than that of the reference value, the subject is likely to have cancer.

In some embodiments, a prediction model can be established using one or more of the determined values described herein. In some embodiments, a ROC curve can be made, and the AUC value is at least or about 0.75, at least or about 0.76, at least or about 0.77, at least or about 0.78, at least or about 0.79, at least or about 0.80, at least or about 0.81, at least or about 0.82, at least or about 0.83, at least or about 0.84, at least or about 0.85, at least or about 0.86, at least or about 0.87, at least or about 0.88, at least or about 0.89, at least or about 0.90.

In some embodiments, the fragment size difference for sequence reads with SNV and SNP mutation is calculated. The SNV/SNP mutations are classified based on the based on published database and inhouse database. In some examples, SNP is defined as a germline substitution of a single nucleotide at a specific position in the genome with the frequency in the population greater than e.g., 1% or 5%, more preferably greater than 1%. All other mutations are then filtered, for example mutations with frequency less than 0.3% are removed, and clonal hematopoiesis of indeterminate potential (CHIP) mutations are removed. The remaining mutations are SNV mutations. In some embodiments, the maximum difference of the fragment size cumulative distribution of SNP and SNV is calculated. In some embodiments, the value is greater than 0.01, 0.05, 0.1, 0.2, 0.3, 0.4, or 0.5.

Mitochondrial DNA Fragments

In one aspect, the disclosure is related to a method to predict cancer by determining the proportion of reads corresponding to mitochondrial DNA fragments among all reads. In some embodiments, the proportion of reads corresponding to mitochondrial DNA fragments determined from a subject sample is compared with that of a reference value (e.g., the proportion of reads corresponding to mitochondrial DNA fragments from a healthy sample). For example, if the proportion of reads corresponding to mitochondrial DNA fragments is higher (e.g., at least 10%, at least 20%, at least 30%, at least 40%, at least 50%, at least 60%, at least 70%, at least 80%, at least 90%, or at least 1-fold higher) than that of the reference value, the subject is likely to have cancer.

In some embodiments, the method described herein includes determining the proportion of reads corresponding to mitochondrial DNA fragments, wherein the mitochondrial DNA fragments are less than less than 160 bp, less than 150 bp, less than 140 bp, less than 130 bp, less than 120 bp, less than 110 bp, or less than 100 bp. In some embodiments, the mitochondrial DNA fragments are less than 150 bp.

Blood Sample Mutation Burden (bTMB)

In one aspect, the disclosure is related to a method to predict cancer by determining the blood sample mutation burden (bTMB). In some embodiments, the sample mutation burden is the average number of single nucleotide mutations per megabase (M).

In some embodiments, the bTMB determined from a subject sample is compared with that of a reference value (e.g., the bTMB of a healthy sample). For example, if the bTMB is higher (e.g., at least 10%, at least 20%, at least 30%, at least 40%, at least 50%, at least 60%, at least 70%, at least 80%, at least 90%, or at least 1-fold higher) than that of the reference value, the subject is likely to have cancer.

In some embodiments, a ROC curve can be made according to the bTMB, and the AUC value is at least or about 0.75, at least or about 0.76, at least or about 0.77, at least or about 0.78, at least or about 0.79, at least or about 0.80, at least or about 0.81, at least or about 0.82, at least or about 0.83, at least or about 0.84, at least or about 0.85, at least or about 0.86, at least or about 0.87, at least or about 0.88, at least or about 0.89, at least or about 0.90.

Fragment Size Difference Between SNV and SNP

In one aspect, the disclosure is related to a method to predict cancer by determining the fragment size difference between SNV and SNP (FS_Diff). In some embodiments, the value of FS_Diff determined from a subject sample is compared with that of a reference value (e.g., the FS_Diff of a healthy sample). For example, if the FS_Diff is higher (e.g., at least 10%, at least 20%, at least 30%, at least 40%, at least 50%, at least 60%, at least 70%, at least 80%, at least 90%, or at least 1-fold higher) than that of the reference value, the subject is likely to have cancer.

In some embodiments, a ROC curve can be made according to the value of FS_Diff, and the AUC value is at least or about 0.65, at least or about 0.66, at least or about 0.67, at least or about 0.68, at least or about 0.69, at least or about 0.70, at least or about 0.70, at least or about 0.71, at least or about 0.72, at least or about 0.73, at least or about 0.74, at least or about 0.75, at least or about 0.76, at least or about 0.77, at least or about 0.78, at least or about 0.79, at least or about 0.80.

Sample Preparation

Provided herein are methods and compositions for analyzing nucleic acids. In some embodiments, nucleic acid fragments in a mixture of nucleic acid fragments are analyzed. A mixture of nucleic acids can comprise two or more nucleic acid fragment species having different nucleotide sequences, different fragment lengths, different origins (e.g., genomic origins, cell or tissue origins, tumor origins, cancer origins, sample origins, subject origins, fetal origins, maternal origins), or combinations thereof.

Nucleic acid or a nucleic acid mixture described herein can be isolated from a sample obtained from a subject. A subject can be any living or non-living organism, including but not limited to a human, a non-human animal, a mammal, a plant, a bacterium, a fungus or a virus. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject can be a male or female.

Nucleic acid can be isolated from any type of suitable biological specimen or sample (e.g., a test sample). A sample or test sample can be any specimen that is isolated or obtained from a subject (e.g., a human subject). Non-limiting examples of specimens include fluid or tissue from a subject, including, without limitation, blood, serum, umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy sample, celocentesis sample, fetal cellular remnants, urine, feces, sputum, saliva, nasal mucous, prostate fluid, lavage, semen, lymphatic fluid, bile, tears, sweat, breast milk, breast fluid, embryonic cells and fetal cells (e.g. placental cells).

In some embodiments, a biological sample can be blood, plasma or serum. As used herein, the term "blood" encompasses whole blood or any fractions of blood, such as serum and plasma. Blood or fractions thereof can comprise cell-free or intracellular nucleic acids. Blood can comprise buffy coats. Buffy coats are sometimes isolated by utilizing a ficoll gradient. Buffy coats can comprise white blood cells (e.g., leukocytes, T-cells, B-cells, platelets). Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to or after preparation. A fluid or tissue sample from which nucleic acid is extracted can be acellular (e.g., cell-free). In some embodiments, a fluid or tissue sample can contain cellular elements or cellular remnants. In some embodiments, cancer cells or tumor cells can be included in the sample.

A sample often is heterogeneous. In many cases, more than one type of nucleic acid species is present in the sample. For example, heterogeneous nucleic acid can include, but is not limited to, cancer and non-cancer nucleic acid, pathogen and host nucleic acid, and/or mutated and wild-type nucleic acid. A sample may be heterogeneous because more than one cell type is present, such as a cancer and non-cancer cell, or a pathogenic and host cell.

In some embodiments, the sample comprise cell free DNA (cfDNA) or circulating tumor DNA (ctDNA). As used herein, the term "cell-free DNA" or "cfDNA" refers to DNA that is freely circulating in the bloodstream. These cfDNA can be isolated from a source having substantially no cells. In some embodiments, these extracellular nucleic acids can be present in and obtained from blood. Extracellular nucleic acid often includes no detectable cells and may contain cellular elements or cellular remnants. Non-limiting examples of acellular sources for extracellular nucleic acid are blood, blood plasma, blood serum and urine. As used herein, the term "obtain cell-free circulating sample nucleic acid" includes obtaining a sample directly (e.g., collecting a sample, e.g., a test sample) or obtaining a sample from another who has collected a sample. Without being limited by theory, extracellular nucleic acid may be a product of cell apoptosis and cell breakdown, which provides basis for extracellular nucleic acid often having a series of lengths across a spectrum (e.g., a "ladder").

Extracellular nucleic acid can include different nucleic acid species. For example, blood serum or plasma from a person having cancer can include nucleic acid from cancer cells and nucleic acid from non-cancer cells. As used herein, the term "circulating tumor DNA" or "ctDNA" refers to tumor-derived fragmented DNA in the bloodstream that is not associated with cells. ctDNA usually originates directly from the tumor or from circulating tumor cells (CTCs). The circulating tumor cells are viable, intact tumor cells that shed from primary tumors and enter the bloodstream or lymphatic system. The ctDNA can be released from tumor cells by apoptosis and necrosis (e.g., from dying cells), or active release from viable tumor cells (e.g., secretion). Studies show that the size of fragmented ctDNA is predominantly 166 bp long, which corresponds to the length of DNA wrapped around a nucleosome plus a linker. Fragmentation of this length might be indicative of apoptotic DNA fragmentation, suggesting that apoptosis may be the primary method of ctDNA release. Thus, in some embodiments, the length of ctDNA or cfDNA can be at least or about 70, 80, 90, 100, 110, 120, 130, 140, 150, 160, 170, 180, 190, or 200 bp. In some embodiments, the length of ctDNA or cfDNA can be less than about 70, 80, 90, 100, 110, 120, 130, 140, 150, 160, 170, 180, 190, or 200 bp. In some embodiments, the cell-free nucleic acid is of a length of about 500, 250, or 200 base pairs or less.

The present disclosure provides methods of separating, enriching and analyzing cell free DNA or circulating tumor DNA found in blood as a non-invasive means to detect the presence and/or to monitor the progress of a cancer. Thus, the first steps of practicing the methods described herein are to obtain a blood sample from a subject and extract DNA from the subject.

A blood sample can be obtained from a subject (e.g., a subject who is suspected to have cancer). The procedure can be performed in hospitals or clinics. An appropriate amount of peripheral blood, e.g., typically between 1 and 50 ml (e.g., between 1 and 10 ml), can be collected. Blood samples can be collected, stored or transported in a manner known to the person of ordinary skill in the art to minimize degradation or the quality of nucleic acid present in the sample. In some embodiments, the blood can be placed in a tube containing EDTA to prevent blood clotting, and plasma can then be obtained from whole blood through centrifugation. Serum can be obtained with or without centrifugation-following blood clotting. If centrifugation is used then it is typically, though not exclusively, conducted at an appropriate speed, e.g., 1,500-3,000×g. Plasma or serum can be subjected to additional centrifugation steps before being transferred to a fresh tube for DNA extraction.

In addition to the acellular portion of the whole blood, DNA can also be recovered from the cellular fraction, enriched in the buffy coat portion, which can be obtained following centrifugation of a whole blood sample.

There are numerous known methods for extracting DNA from a biological sample including blood. The general methods of DNA preparation (e.g., described by Sambrook and Russell, Molecular Cloning: A Laboratory Manual 3d ed., 2001) can be followed; various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), may also be used to obtain DNA from a blood sample.

cfDNA purification is prone to contamination due to ruptured blood cells during the purification process. Because of this, different purification methods can lead to significantly different cfDNA extraction yields. In some embodiments, purification methods involve collection of blood via venipuncture, centrifugation to pellet the cells, and extraction of cfDNA from the plasma. In some embodiments, after extraction, cell-free DNA can be about or at least 50% of the overall nucleic acid (e.g., about or at least 50%, 60%, 70%, 80%, 90%, 91%, 92%, 93%, 94%, 95%, 96%, 97%, 98%, or 99% of the total nucleic acid is cell-free DNA).

The nucleic acid that can be analyzed by the methods described herein include, but are not limited to, DNA (e.g., complementary DNA (cDNA), genomic DNA (gDNA), cfDNA, or ctDNA), ribonucleic acid (RNA) (e.g., message RNA (mRNA), short inhibitory RNA (siRNA), ribosomal RNA (rRNA), transfer RNA (tRNA), or microRNA), and/or DNA or RNA analogs (e.g., containing base analogs, sugar analogs and/or a non-native backbone and the like), RNA/DNA hybrids and polyamide nucleic acids (PNAs), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, supercoiled, single-stranded, or double-stranded). A nucleic acid in some embodiments can be from a single chromosome or fragment thereof (e.g., a nucleic acid sample may be from one chromosome of a sample obtained from a diploid organism). In certain embodiments nucleic acids comprise nucleosomes, fragments or parts of nucleosomes or nucleosome-like structures.

Nucleic acid provided for processes described herein can contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

In some embodiments, the nucleic acid can be extracted, isolated, purified, partially purified or amplified from the samples before sequencing. In some embodiments, nucleic acid can be processed by subjecting nucleic acid to a method that generates nucleic acid fragments. Fragments can be generated by a suitable method known in the art, and the average, mean or nominal length of nucleic acid fragments can be controlled by selecting an appropriate fragment-generating procedure. In certain embodiments, nucleic acid of a relatively shorter length can be utilized to analyze sequences that contain little sequence variation and/or contain relatively large amounts of known nucleotide sequence information. In some embodiments, nucleic acid of a relatively longer length can be utilized to analyze sequences that contain greater sequence variation and/or contain relatively small amounts of nucleotide sequence information.

Sequencing

Nucleic acids (e.g., nucleic acid fragments, sample nucleic acid, cell-free nucleic acid, circulating tumor nucleic acids) are sequenced before the analysis.

As used herein, "reads" or "sequence reads" are short nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads).

Sequence reads obtained from cell-free DNA can be reads from a mixture of nucleic acids derived from normal cells or tumor cells. A mixture of relatively short reads can be transformed by processes described herein into a representation of a genomic nucleic acid present in a subject. In certain embodiments, "obtaining" nucleic acid sequence reads of a sample can involve directly sequencing nucleic acid to obtain the sequence information.

Sequence reads can be mapped and the number of reads or sequence tags mapping to a specified nucleic acid region (e.g., a chromosome, a bin, a genomic section) are referred to as counts. In some embodiments, counts can be manipulated or transformed (e.g., normalized, combined, added, filtered, selected, averaged, derived as a mean, the like, or a combination thereof).

In some embodiments, a group of nucleic acid samples from one individual are sequenced. In certain embodiments, nucleic acid samples from two or more samples, wherein each sample is from one individual or two or more individuals, are pooled and the pool is sequenced together. In some embodiments, a nucleic acid sample from each biological sample often is identified by one or more unique identification tags.

The nucleic acids can also be sequenced with redundancy. A given region of the genome or a region of the cell-free DNA can be covered by two or more reads or overlapping reads (e.g., "fold" coverage greater than 1). Coverage (or depth) in DNA sequencing refers to the number of unique reads that include a given nucleotide in the reconstructed sequence. In some embodiments, a fraction of the genome is sequenced, which sometimes is expressed in the amount of the genome covered by the determined nucleotide sequences (e.g., "fold" coverage less than 1). Thus, in some embodiments, the fold is calculated based on the entire genome. In some embodiments, cell free DNAs are sequenced and the fold is calculated based on the entire genome. Thus, it is easier to compare the amount of sequencing and the amount of sequencing reads that are generated for different projects.

The fold can also be calculated based on the length of the reconstructed sequence (e.g., cfDNA). When the cell free DNA is sequenced with about 1-fold coverage that is calculated based on the reconstructed sequence (e.g., panel sequencing), the number of nucleotides in all unique reads would be roughly the same as the entire nucleotide sequence of the cfDNA in the sample.

In some embodiments, the nucleic acid is sequenced with about 0.1-fold to about 100-fold coverage, about 0.2-fold to 20-fold coverage, or about 0.2-fold to about 1-fold coverage. In some embodiments, sequencing is performed by about or at least 0.2, 0.3, 0.4, 0.5, 0.6, 0.7, 0.8, 0.9, 1, 2, 3, 4, 5, 6, 7, 8, 9, 10, 15, 20, 30, 40, 50, 60, 70, 80, 90, 100, 200, 300, 400, 500, or 1000 fold coverage. In some embodiments, sequencing is performed by no more than 0.2, 0.3, 0.4, 0.5, 0.6, 0.7, 0.8, 0.9, 1, 2, 3, 4, 5, 6, 7, 8, 9, 10, 15, 20, 30, 40, 50, 60, 70, 80, 90, 100, 200, 300, 400, 500, or 1000 coverage. In some embodiments, sequencing is performed by no more than 15, 20, 30, 40, 50, 60, 70, 80, 90 or 100 fold coverage.

In some embodiments, the sequence coverage is performed by about or at least 0.2, 0.3, 0.4, 0.5, 0.6, 0.7, 0.8, 0.9, 1, 2, 3, 4, or 5 fold (e.g., as determined by the entire genome).

In some embodiments, the sequence coverage is performed by no more than 0.2, 0.3, 0.4, 0.5, 0.6, 0.7, 0.8, 0.9, 1, 2, 3, 4, or 5 fold (e.g., as determined by the entire genome).

In some embodiments, the sequence coverage is performed by about or at least 100, 150, 200, 250, 300, 350, 400, 450, or 500 fold (e.g., as determined by reconstructed sequence). In some embodiments, the sequence coverage is performed by no more than 100, 150, 200, 250, 300, 350, 400, 450, or 500 fold (e.g., as determined by reconstructed sequence).

In some embodiments, a sequencing library can be prepared prior to or during a sequencing process. Methods for preparing the sequencing library are known in the art and commercially available platforms may be used for certain applications. Certain commercially available library platforms may be compatible with sequencing processes described herein. For example, one or more commercially available library platforms may be compatible with a sequencing by synthesis process. In certain embodiments, a ligation-based library preparation method is used (e.g., ILLUMINA TRUSEQ, Illumina, San Diego CA). Ligation-based library preparation methods typically use a methylated adaptor design which can incorporate an index sequence at the initial ligation step and often can be used to prepare samples for single-read sequencing, paired-end sequencing and multiplexed sequencing. In certain embodiments, a transposon-based library preparation method is used (e.g., EPICENTRE NEXTERA, Epicentre, Madison WI). Transposon-based methods typically use in vitro transposition to simultaneously fragment and tag DNA in a single-tube reaction (often allowing incorporation of platform-specific tags and optional barcodes), and prepare sequencer-ready libraries.

Any sequencing method suitable for conducting methods described herein can be used. In some embodiments, a high-throughput sequencing method is used. High-throughput sequencing methods generally involve clonally amplified DNA templates or single DNA molecules that are sequenced in a massively parallel fashion within a flow cell. Such sequencing methods also can provide digital quantitative information, where each sequence read is a countable "sequence tag" or "count" representing an individual clonal DNA template, a single DNA molecule, bin or chromosome.

Next generation sequencing techniques capable of sequencing DNA in a massively parallel fashion are collectively referred to herein as "massively parallel sequencing" (MPS). High-throughput sequencing technologies include, for example, sequencing-by-synthesis with reversible dye terminators, sequencing by oligonucleotide probe ligation, pyrosequencing and real time sequencing. Non-limiting examples of MPS include Massively Parallel Signature Sequencing (MPSS), Polony sequencing, Pyrosequencing, Illumina (Solexa) sequencing, SOLiD sequencing, Ion semiconductor sequencing, DNA nanoball sequencing, Helioscope single molecule sequencing, single molecule real time (SMRT) sequencing, nanopore sequencing, ION Torrent and RNA polymerase (RNAP) sequencing. Some of these sequencing methods are described e.g., in US20130288244A1, which is incorporated herein by reference in its entirety.

Systems utilized for high-throughput sequencing methods are commercially available and include, for example, the Roche 454 platform, the Applied Biosystems SOLID platform, the Helicos True Single Molecule DNA sequencing technology, the sequencing-by-hybridization platform from Affymetrix Inc., the single molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and nanopore sequencing also can be used in high-throughput sequencing approaches.

The length of the sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, the sequence reads are of a mean, median or average length of about 15 bp to 900 bp long (e.g., about or at least 20 bp, 25 bp, 30 bp, 35 bp, 40 bp, 45 bp, 50 bp, 55 bp, 60 bp, 65 bp, 70 bp, 75 bp, 80 bp, 85 bp, 90 bp, 95 bp, 100 bp, 110 bp, 120 bp, 130, 140 bp, 150 bp, 200 bp, 250 bp, 300 bp, 350 bp, 400 bp, 450 bp, or 500 bp). In some embodiments, the sequence reads are of a mean, median or average length of about 1000 bp or more. In some embodiments, the sequence reads are of less than 60 bp, 65 bp, 70 bp, 75 bp, 80 bp, 85 bp, 90 bp, 95 bp, 100 bp, 110 bp, 120 bp, 130, 140 bp, 150 bp, 200 bp, 250 bp, 300 bp, 350 bp, 400 bp, 450 bp, or 500 bp are removed because of poor quality.

Mapping nucleotide sequence reads (i.e., sequence information from a fragment whose physical genomic position is unknown) can be performed in a number of ways, and often comprises alignment of the obtained sequence reads with a matching sequence in a reference genome (e.g., Li et al., "Mapping short DNA sequencing reads and calling variants using mapping quality score," Genome Res., 2008 Aug. 19.) In such alignments, sequence reads generally are aligned to a reference sequence and those that align are designated as being "mapped" or a "sequence tag." In certain embodiments, a mapped sequence read is referred to as a "hit" or a "count".

As used herein, the terms "aligned", "alignment", or "aligning" refer to two or more nucleic acid sequences that can be identified as a match (e.g., 100% identity) or partial match. Alignments can be done manually or by a computer algorithm, examples including the Efficient Local Alignment of Nucleotide Data (ELAND) computer program distributed as part of the Illumina Genomics Analysis pipeline. The alignment of a sequence read can be a 100% sequence match. In some cases, an alignment is less than a 100% sequence match (i.e., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand. In certain embodiments, a nucleic acid sequence is aligned with the reverse complement of another nucleic acid sequence.

Various computational methods can be used to map each sequence read to a genomic region. Non-limiting examples of computer algorithms that can be used to align sequences include, without limitation, BLAST, BLITZ, FASTA, BOWTIE 1, BOWTIE 2, ELAND, MAQ, PROBEMATCH, SOAP or SEQMAP, or variations thereof or combinations thereof. In some embodiments, sequence reads can be aligned with sequences in a reference genome. In some embodiments, the sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search the identified sequences against a sequence database. Search hits can then be used to sort the identified sequences into appropriate genomic sections, for example. Some of the methods of analyzing sequence reads are described e.g., US20130288244A1, which is incorporated herein by reference in its entirety.

Detecting Cancer

The present disclosure provides methods of detecting and/or treating cancer.

In some embodiments, sequencing cell free DNA permits broader inquiries, allowing assessment of the mutation status of thousands/millions of positions. In some embodiments, detection of mutations at oncogenes or tumor suppressor genes indicate that the subject is likely to have cancer.

In some embodiments, the methods involve detection of specific mutations at oncogenes and/or tumor suppressor genes, e.g., detection of one or more mutations in EGFR, KRAS, TP53, IDH1, PIK3CA, BRAF, and/or NRAS In some embodiments, copy number variations and structural variants in the oncogenes and/or tumor suppressor genes indicate that the subject is likely to have cancer.

In some embodiments, mutation burden is used to detect cancer. As used herein, the term "mutation burden" refers to the level, e.g., number, of an alteration (e.g., one or more alterations, e.g., one or more somatic alterations) per a preselected unit (e.g., per megabase) in a predetermined set of genes (e.g., in the coding regions of the predetermined set of genes). Mutation load can be measured, e.g., on a whole genome or exome basis, on the basis of a subset of genome or exome, or on cfDNA. In certain embodiments, the mutation load measured on the basis of a subset of genome or exome can be extrapolated to determine a whole genome or exome mutation load.

In some embodiments, the tumor mutation burden are limited to non-synonymous mutations. In some embodiments, the tumor mutation burden are limited to oncogenes and/or tumor suppressor genes. In some embodiments, the tumor mutation burden are limited to single nucleotide mutations, In some embodiments, the tumor mutation burden are including short insertion/deletion (InDel)

In certain embodiments, the mutation load is measured in a sample, e.g., a tumor sample (e.g., a tumor sample or a sample derived from a tumor), from a subject, e.g., a subject described herein. In certain embodiments, the mutation load is expressed as a percentile, e.g., among the mutation loads in samples from a reference population. In certain embodiments, the reference population includes patients having the same type of cancer as the subject. In other embodiments, the reference population includes patients who are receiving, or have received, the same type of therapy, as the subject. In some embodiments, a subject is likely to have cancer if the mutation load is higher than a reference threshold. The subject is less likely to have cancer if the mutation load is lower than a reference threshold.

In some embodiments, the mutation burden can determine sensitivity to a therapeutic agent, e.g., a checkpoint inhibitor (e.g., anti-PD-1 antibody). In some embodiments, the therapy is an immunotherapy.

Some of these methods involving tumor mutation burden are described e.g., in Rizvi et al. "Mutational landscape determines sensitivity to PD-1 blockade in non-small cell lung cancer." Science 348.6230 (2015): 124-128; Addeo et al., "Measuring tumor mutation burden in cell-free DNA: advantages and limits." Translational Lung Cancer Research (2019), which are incorporated herein by reference in the entirety.

In some aspects, the methods described herein can also be used to detect recurrence. Thus, the methods described herein can be used to predict eventual recurrence, e.g., after surgery, chemotherapy, or some other curative treatments.

In some aspects, the methods described herein can also be used to evaluate treatment response and progression. Sequencing cell free DNA or circulating tumor DNA can be used to guide the choice of therapeutic agent and to monitor dynamic tumor responses throughout treatment. For example, the reemergence or significant increase in plasma tumor DNA during drug treatment, is strongly correlated with radiographic/clinical progression. Thus, in some embodiments, a decrease of plasma tumor DNA (while tumor or cancer symptoms persist) after the significant increase suggests the development of drug resistance, and the need of switching therapies. Some of these methods are described, e.g., in Ulrich et al, "Cell-free DNA in oncology: gearing up for clinic." Annals of laboratory medicine 38.1 (2018): 1-8; Babayan et al., "Advances in liquid biopsy approaches for early detection and monitoring of cancer." Genome medicine 10.1 (2018): 21, which are incorporated herein by reference in the entirety.

In some embodiments, certain medical procedures can be performed if a subject is identified as having an increased risk of having cancer. In some embodiments, these medical procedures can further confirm whether the subject has cancer. Some embodiments further include imaging procedures (e.g., CT scan, nuclear scan, ultrasound, MRI, PET scan, X-rays), biopsy (e.g., with a needle, with an endoscope, with surgery, excisional biopsy, incisional biopsy), or further lab tests (e.g., testing blood, urine, or other body fluids).

Some embodiments further include updating or recording the subject's risk of a cancer (e.g., a subject's increased risk of having cancer or tumor) in a clinical record or database. Some embodiments further include performing increased monitoring on a subject identified as having an increased risk of a cancer (e.g., increased periodicity of physical examination, and increased frequency of clinic visits). Some embodiments further include recording the need for increased monitoring in a clinical record or database for a subject identified as having an increased risk of having cancer. Some embodiments further include informing the subject to self-monitor for the symptoms of cancer. Some embodiments of the methods described herein include recommending a lifestyle change. Some of the lifestyle change include, but are not limited to, dietary change (e.g., eating more fruits and vegetables, eating less red meat, reduce alcohol consumption), taking vaccination (e.g., taking human papillomavirus vaccine, or hepatitis B vaccine), taking medications (e.g., nonsteroidal anti-inflammatory drug, COX-2 inhibitors, tamoxifen or raloxifene), lose weight, and/or do more exercise.

Methods of Treatment

The present disclosure provides methods of treating a disease or a disorder as described herein. In some embodiments, the disease or the disorder is cancer. In one aspect, the disclosure provides methods for treating a cancer in a subject, methods of reducing the rate of the increase of volume of a tumor in a subject over time, methods of reducing the risk of developing a metastasis, or methods of reducing the risk of developing an additional metastasis in a subject. In some embodiments, the treatment can halt, slow, retard, or inhibit progression of a cancer. In some embodiments, the treatment can result in the reduction of in the number, severity, and/or duration of one or more symptoms of the cancer in a subject. In some embodiments, the compositions and methods disclosed herein can be used for treatment of patients at risk for a cancer.

The treatments can generally include e.g., surgery, chemotherapy, radiation therapy, hormonal therapy, targeted therapy, and/or a combination thereof. Which treatments are used depends on the type, location and grade of the cancer as well as the patient's health and preferences. In some embodiments, the therapy is chemotherapy or chemoradiation.

In one aspect, the disclosure features methods that include administering a therapeutically effective amount of a therapeutic agent to the subject in need thereof (e.g., a subject having, or identified or diagnosed as having, a cancer). In some embodiments, the subject has e.g., breast cancer (e.g., triple-negative breast cancer), carcinoid cancer, cervical cancer, endometrial cancer, glioma, head and neck cancer, liver cancer, lung cancer, small cell lung cancer, lymphoma, melanoma, ovarian cancer, pancreatic cancer, prostate cancer, renal cancer, colorectal cancer, gastric cancer, testicular cancer, thyroid cancer, bladder cancer, urethral cancer, or hematologic malignancy. In some embodiments, the cancer is unresectable melanoma or metastatic melanoma, non-small cell lung carcinoma (NSCLC), small cell lung cancer (SCLC), bladder cancer, or metastatic hormone-refractory prostate cancer. In some embodiments, the subject has a solid tumor. In some embodiments, the cancer is squamous cell carcinoma of the head and neck (SCCHN), renal cell carcinoma (RCC), triple-negative breast cancer (TNBC), or colorectal carcinoma. In some embodiments, the subject has triple-negative breast cancer (TNBC), gastric cancer, urothelial cancer, Merkel-cell carcinoma, or head and neck cancer.

As used herein, by an "effective amount" is meant an amount or dosage sufficient to effect beneficial or desired results including halting, slowing, retarding, or inhibiting progression of a disease, e.g., a cancer. An effective amount will vary depending upon, e.g., an age and a body weight of a subject to which the therapeutic agent is to be administered, a severity of symptoms and a route of administration, and thus administration can be determined on an individual basis. An effective amount can be administered in one or more administrations. By way of example, an effective amount is an amount sufficient to ameliorate, stop, stabilize, reverse, inhibit, slow and/or delay progression of a cancer in a patient or is an amount sufficient to ameliorate, stop, stabilize, reverse, slow and/or delay proliferation of a cell (e.g., a biopsied cell, any of the cancer cells described herein, or cell line (e.g., a cancer cell line)) in vitro.

In some embodiments, the methods described herein can be used to monitor the progression of the disease, determine the effectiveness of the treatment, and adjust treatment strategy. For example, cell free DNA can be collected from the subject to detect cancer and the information can also be used to select appropriate treatment for the subject. After the subject receives a treatment, cell free DNA can be collected from the subject. The analysis of these cfDNA can be used to monitor the progression of the disease, determine the effectiveness of the treatment, and/or adjust treatment strategy. In some embodiments, the results are then compared to the early results. In some embodiments, a dramatic increase of circulating tumor DNA indicates apoptosis at the tumor cells, which may suggest that the treatment is effective.

In some embodiments, the therapeutic agent can comprise one or more inhibitors selected from the group consisting of an inhibitor of B-Raf, an EGFR inhibitor, an inhibitor of a MEK, an inhibitor of ERK, an inhibitor of K-Ras, an inhibitor of c-Met, an inhibitor of anaplastic lymphoma kinase (ALK), an inhibitor of a phosphatidylinositol 3-kinase (PI3K), an inhibitor of an Akt, an inhibitor of mTOR, a dual PI3K/mTOR inhibitor, an inhibitor of Bruton's tyrosine kinase (BTK), and an inhibitor of Isocitrate dehydrogenase 1 (IDH1) and/or Isocitrate dehydrogenase 2 (IDH2). In some embodiments, the additional therapeutic agent is an inhibitor of indoleamine 2,3-dioxygenase-1) (IDO1) (e.g., epacadostat).

In some embodiments, the therapeutic agent can comprise one or more inhibitors selected from the group consisting of an inhibitor of HER3, an inhibitor of LSD1, an inhibitor of MDM2, an inhibitor of BCL2, an inhibitor of CHK1, an inhibitor of activated hedgehog signaling pathway, and an agent that selectively degrades the estrogen receptor.

In some embodiments, the therapeutic agent can comprise one or more therapeutic agents selected from the group consisting of Trabectedin, nab-paclitaxel, Trebananib, Pazopanib, Cediranib, Palbociclib, everolimus, fluoropyrimidine, IFL, regorafenib, Reolysin, Alimta, Zykadia, Sutent, temsirolimus, axitinib, everolimus, sorafenib, Votrient, Pazopanib, IMA-901, AGS-003, cabozantinib, Vinflunine, an Hsp90 inhibitor, Ad-GM-CSF, Temazolomide, IL-2, IFNa, vinblastine, Thalomid, dacarbazine, cyclophosphamide, lenalidomide, azacytidine, lenalidomide, bortezomid, amrubicine, carfilzomib, pralatrexate, and enzastaurin.

In some embodiments, the therapeutic agent can comprise one or more therapeutic agents selected from the group consisting of an adjuvant, a TLR agonist, tumor necrosis factor (TNF) alpha, IL-1, HMGB1, an IL-10 antagonist, an IL-4 antagonist, an IL-13 antagonist, an IL-17 antagonist, an HVEM antagonist, an ICOS agonist, a treatment targeting $Cx_3CL1$, a treatment targeting CXCL9, a treatment targeting CXCL10, a treatment targeting CCL5, an LFA-1 agonist, an ICAM1 agonist, and a Selectin agonist.

In some embodiments, carboplatin, nab-paclitaxel, paclitaxel, cisplatin, pemetrexed, gemcitabine, FOLFOX, or FOLFIRI are administered to the subject.

In some embodiments, the therapeutic agent is an antibody or antigen-binding fragment thereof. In some embodiments, the therapeutic agent is an antibody that specifically binds to PD-1, CTLA-4, BTLA, PD-L1, CD27, CD28, CD40, CD47, CD137, CD154, TIGIT, TIM-3, GITR, or OX40.

In some embodiments, the therapeutic agent is an anti-PD-1 antibody, an anti-OX40 antibody, an anti-PD-L1 antibody, an anti-PD-L2 antibody, an anti-LAG-3 antibody, an anti-TIGIT antibody, an anti-BTLA antibody, an anti-CTLA-4 antibody, or an anti-GITR antibody.

In some embodiments, the therapeutic agent is an anti-CTLA4 antibody (e.g., ipilimumab), an anti-CD20 antibody (e.g., rituximab), an anti-EGFR antibody (e.g., cetuximab), an anti-CD319 antibody (e.g., elotuzumab), or an anti-PD1 antibody (e.g., nivolumab).

Systems, Software, and Interfaces

The methods described herein (e.g., quantifying, mapping, normalizing, range setting, adjusting, categorizing, counting and/or determining sequence reads, and counts) often require a computer, processor, software, module or other apparatus. Methods described herein typically are computer-implemented methods, and one or more portions of a method sometimes are performed by one or more processors. Embodiments pertaining to methods described herein generally are applicable to the same or related processes implemented by instructions in systems, apparatus and computer program products described herein. In some embodiments, processes and methods described herein are performed by automated methods. In some embodiments, an automated method is embodied in software, modules, processors, peripherals and/or an apparatus comprising the like, that determine sequence reads, counts, mapping, mapped sequence tags, elevations, profiles, normalizations, comparisons, range setting, categorization, adjustments, plotting, outcomes, transformations and identifications. As used herein, software refers to computer readable program instructions that, when executed by a processor, perform computer operations, as described herein.

Sequence reads, counts, elevations, and profiles derived from a subject (e.g., a control subject, a patient or a subject is suspected to have tumor) can be analyzed and processed to determine the presence or absence of a genetic variation. Sequence reads and counts sometimes are referred to as "data" or "datasets". In some embodiments, data or datasets can be characterized by one or more features or variables. In some embodiments, the sequencing apparatus is included as part of the system. In some embodiments, a system comprises a computing apparatus and a sequencing apparatus, where the sequencing apparatus is configured to receive physical nucleic acid and generate sequence reads, and the computing apparatus is configured to process the reads from the sequencing apparatus. The computing apparatus sometimes is configured to determine the presence or absence of a genetic variation (e.g., copy number variation, mutations) from the sequence reads.

Implementations of the subject matter and the functional operations described herein can be implemented in digital electronic circuitry, in tangibly-embodied computer software or firmware, in computer hardware, including the structures described herein and their structural equivalents, or in combinations of one or more of the structures. Implementations of the subject matter described herein can be implemented as one or more computer programs, i.e., one or more modules of computer program instructions encoded on a tangible program carrier for execution by, or to control the operation of, a processing device. Alternatively, or in addition, the program instructions can be encoded on a propagated signal that is an artificially generated signal, e.g., a machine-generated electrical, optical, or electromagnetic signal that is generated to encode information for transmission to suitable receiver apparatus for execution by a processing device. A machine-readable medium can be a machine-readable storage device, a machine-readable storage substrate, a random or serial access memory device, or a combination of one or more of them.

Figure 21:
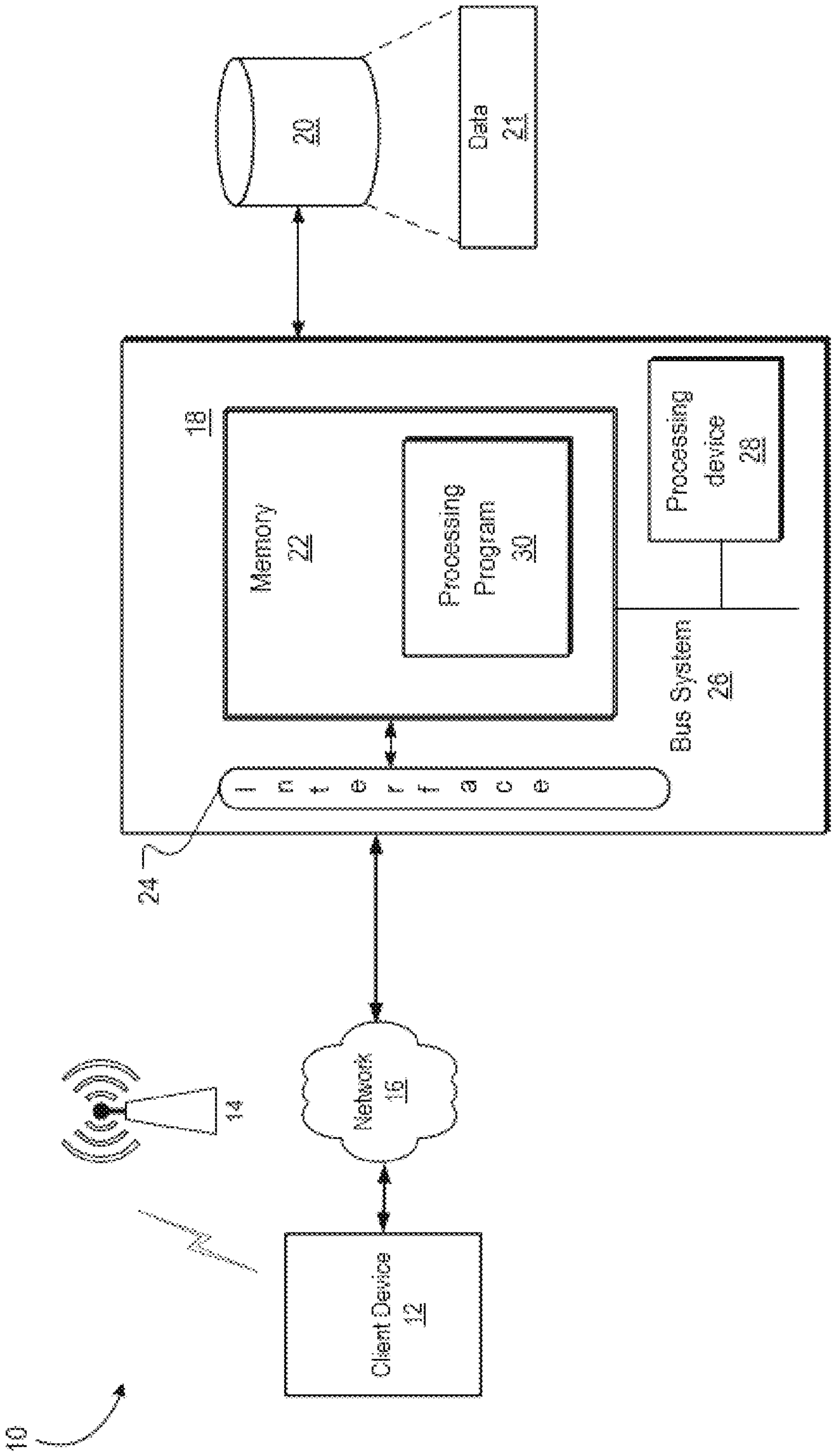
FIG. 21 is a schematic diagram showing a system for determining cancer risk.

Referring to FIG. 21, system 10 processes data via binding data to parameters and applying a processor to the input data, and outputs information (e.g., quality score, Information Score, probabilities) indicative of cancer risk. System 10 includes client device 12, data processing system 18, data repository 20, network 16, and wireless device 14. The processor processes the input data based on the methods described herein. In some embodiments, the processor generates a quality score (e.g., information score) based on the methods described herein.

Data processing system 18 retrieves, from data repository 20, data 21 representing one or more values for the processor parameter, including e.g., the chromosome instability index, fragment size, protein tumor markers, the proportion of mitochondrial DNA fragments below certain sizes, concentration of cfDNA, etc. Data processing system 18 inputs the retrieved data into a processor, e.g., into data processing program 30. In this embodiment, data processing program 30 is programmed to determine the risk of cancer or the probability of having a cancer. In some embodiments, the probability is calculated by a logistic regression.

In some embodiments, data processing system 18 binds to parameter one or more values representing information associated with cfDNA. Data processing system 18 binds values of the data to the parameter by modifying a database record such that a value of the parameter is set to be the value of data 21 (or a portion thereof). Data 21 includes a plurality of data records that each have one or more values for the parameter. In some embodiments, data processing system 18 applies data processing program 30 to each of the records by applying data processing program 30 to the bound values for the parameter. Based on application of data processing program 30 to the bound values (e.g., as specified in data 21 or in records in data 21), data processing system 18 determines a score indicating whether the test sample is derived from a cancer patient. In some embodiments, data processing system 18 outputs, e.g., to client device 12 via network 16 and/or wireless device 14, data indicative of the determined quality score, or data indicating whether the test sample is derived from a cancer patient.

In some embodiments, based on the data related to cfDNA or some other relevant information as described herein, data processing system 18 can be configured to determine whether a subject has cancer or is at risk of having cancer.

If the data processing system 18 determines that the subject has cancer or is at risk of having cancer, data processing system 18 can further update a clinical record in the data 21, indicating the subject has cancer or is at risk of having cancer. In some embodiments, the record includes the need of performing increased monitoring (e.g., increased periodicity of physical examination, and increased frequency of clinic visits), the need for further procedures (e.g., diagnostics, lab tests, or treatment procedures), and recommendation for a lifestyle change.

Data processing system 18 generates data for a graphical user interface that, when rendered on a display device of client device 12, display a visual representation of the output. In some embodiments, the values for these parameters can be stored in data repository 20 or memory 22.

Client device 12 can be any sort of computing device capable of taking input from a user and communicating over network 16 with data processing system 18 and/or with other client devices. Client device 12 can be a mobile device, a desktop computer, a laptop computer, a cell phone, a personal digital assistant (PDA), a server, an embedded computing system, and so forth.

Data processing system 18 can be any of a variety of computing devices capable of receiving data and running one or more services. In some embodiments, data processing system 18 can include a server, a distributed computing system, a desktop computer, a laptop computer, a cell phone, and the like. Data processing system 18 can be a single server or a group of servers that are at a same position or at different positions (i.e., locations). Data processing system 18 and client device 12 can run programs having a client-server relationship to each other. Although distinct modules are shown in the figure, in some embodiments, client and server programs can run on the same device.

Data processing system 18 can receive data from wireless device 14 and/or client device 12 through input/output (I/O) interface 24 and data repository 20. Data repository 20 can store a variety of data values for data processing program 30. The processing program (which may also be referred to as a program, software, a software application, a script, or code) can be written in any form of programming language, including compiled or interpreted languages, or declarative or procedural languages, and it can be deployed in any form, including as a stand-alone program or as a module, component, subroutine, or other unit suitable for use in a computing environment. The data processing program may, but need not, correspond to a file in a file system. The program can be stored in a portion of a file that holds other programs or information (e.g., one or more scripts stored in a markup language document), in a single file dedicated to the program in question, or in multiple coordinated files (e.g., files that store one or more modules, sub programs, or portions of code). The data processing program can be deployed to be executed on one computer or on multiple computers that are located at one site or distributed across multiple sites and interconnected by a communication network.

In some embodiments, data repository 20 stores data 21 indicative of sequencing reads of samples from control subjects and sequencing reads of samples from tumor patients or patients who are suspected to have tumor. In another embodiment, data repository 20 stores parameters of the processor. Interface 24 can be a type of interface capable of receiving data over a network, including, e.g., an Ethernet interface, a wireless networking interface, a fiber-optic networking interface, a modem, and so forth. Data processing system 18 also includes a processing device 28. As used herein, a "processing device" encompasses all kinds of apparatuses, devices, and machines for processing information, such as a programmable processor, a computer, or multiple processors or computers. The apparatus can include special purpose logic circuitry, e.g., an FPGA (field programmable gate array) or an ASIC (application specific integrated circuit) or RISC (reduced instruction set circuit). The apparatus can also include, in addition to hardware, code that creates an execution environment for the computer program in question, e.g., code that constitutes processor firmware, a protocol stack, an information base management system, an operating system, or a combination of one or more of them.

Data processing system 18 also includes a memory 22 and a bus system 26, including, for example, a data bus and a motherboard, which can be used to establish and to control data communication between the components of data processing system 18. Processing device 28 can include one or more microprocessors. Generally, processing device 28 can include an appropriate processor and/or logic that is capable of receiving and storing data, and of communicating over a network. Memory 22 can include a hard drive and a random access memory storage device, including, e.g., a dynamic random access memory, or other types of non-transitory, machine-readable storage devices. Memory 22 stores data processing program 30 that is executable by processing device 28. These computer programs may include a data engine for implementing the operations and/or the techniques described herein. The data engine can be implemented in software running on a computer device, hardware or a combination of software and hardware.

Various methods and formulae can be implemented, in the form of computer program instructions, and executed by a processing device. Suitable programming languages for expressing the program instructions include, but are not limited to, C, C++, an embodiment of FORTRAN such as FORTRAN77 or FORTRAN90, Java, Visual Basic, Perl, Tcl/Tk, JavaScript, ADA, and statistical analysis software, such as SAS, R, MATLAB, SPSS, and Stata etc. Various aspects of the methods may be written in different computing languages from one another, and the various aspects are caused to communicate with one another by appropriate system-level-tools available on a given system.

The processes and logic flows described in this disclosure can be performed by one or more programmable computers executing one or more computer programs to perform functions by operating on input information and generating output. The processes and logic flows can also be performed by, and apparatus can also be implemented as, special purpose logic circuitry, e.g., an FPGA (field programmable gate array) or an ASIC (application specific integrated circuit) or RISC.

Computers suitable for the execution of a computer program include, by way of example, general or special purpose microprocessors, or both, or any other kind of central processing unit. Generally, a central processing unit will receive instructions and information from a read only memory or a random access memory or both. The essential elements of a computer are a central processing unit for performing or executing instructions and one or more memory devices for storing instructions and information. Generally, a computer will also include, or be operatively coupled to receive information from or transfer information to, or both, one or more mass storage devices for storing information, e.g., magnetic, magneto optical disks, or optical disks. However, a computer need not have such devices. Moreover, a computer can be embedded in another device, e.g., a mobile telephone, a smartphone or a tablet, a touchscreen device or surface, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and information include various forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and (Blue Ray) DVD-ROM disks. The processor and the memory can be supplemented by, or incorporated in, special purpose logic circuitry.

To provide for interaction with a user, implementations of the subject matter described in this disclosure can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well. In addition, a computer can interact with a user by sending documents to and receiving documents from a device that is used by the user; for example, by sending web pages to a web browser on a user's client device in response to requests received from the web browser.

Implementations of the subject matter described herein can be implemented in a computing system that includes a back end component, e.g., as an information server, or that includes a middleware component, e.g., an application server, or that includes a front end component, e.g., a client computer having a graphical user interface or a Web browser through which a user can interact with an implementation of the subject matter, or any combination of one or more such back end, middleware, or front end components. The components of the system can be interconnected by any form or medium of digital information communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, the server can be in the cloud via cloud computing services.

While this disclosure includes many specific implementation details, these should not be construed as limitations on the scope of any of what may be claimed, but rather as descriptions of features that may be specific to particular implementations. Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are described in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Particular implementations of the subject matter have been described. Other implementations are within the scope of the following claims. For example, the actions recited in the claims can be performed in a different order and still achieve desirable results. In one embodiment, the processes depicted in the accompanying figures do not necessarily require the particular order shown, or sequential order, to achieve desirable results. In some implementations, multitasking and parallel processing may be advantageous.

Kits

The present disclosure also provides kits for collecting, transporting, and/or analyzing samples. Such a kit can include materials and reagents required for obtaining an appropriate sample from a subject, or for measuring the levels of particular biomarkers. In some embodiments, the kits include those materials and reagents that would be required for obtaining and storing a sample from a subject. The sample is then shipped to a service center for further processing (e.g., sequencing and/or data analysis).

The kits may further include instructions for collect the samples, performing the assay and methods for interpreting and analyzing the data resulting from the performance of the assay.

EXAMPLES

The invention is further described in the following examples, which do not limit the scope of the invention described in the claims.

Example 1

1. Plasma Separation
   - a) The equipment, reagents, and consumables needed for the experiment were prepared, and a high-speed freezing centrifuge was pre-cooled to 4° C. in advance.
   - b) If the peripheral blood sample was collected in an EDTA anticoagulation tube, the blood should be placed in a refrigerator at 4° C. immediately after the blood was drawn, and the plasma separation was conducted within 2 hours. If the peripheral blood sample was collected in a cell-free nucleic acid storage tube such as streck tube, it could be placed at room temperature, and the plasma was separated within the time specified in the manual of the blood collection tube.
   - c) The sample information was recorded, the blood collection tube was balanced, the high-speed freezing centrifuge was replaced with a horizontal rotor, and the parameters were set to be: temperature at 4° C., centrifugal force of 1600 g, time for 10 min. After balancing the blood collection tube, it was placed in a centrifuge for centrifugation.
   - d) After the centrifugation was completed, the blood collection tube was placed on biological safety cabin. After centrifugation, transferred the supernatant into a new 15 mL tube, and marked with the sample number and operating time on the tube wall. The supernatant should be carefully collected to avoid sucking in white blood cells.

e) The high-speed freezing centrifuge was replaced with an angle rotor, and the parameters were set as: temperature at 4° C., centrifugal force of 16000 g, and time for 10 min. The 15 mL tube containing the supernatant was balanced and placed in a centrifuge for centrifugation.

f) After the centrifugation was completed, the 15 mL tube containing the supernatant was placed on the biological safety cabin. After centrifugation, transferred the supernatant into a new 15 mL tube, and 500 μl of the supernatant was pipetted and stored in a 1.5 mL tube for subsequent tumor marker detection. The supernatant should be carefully collected to avoid sucking in the precipitate. The purpose of this step is to remove impurities such as cell debris in the plasma.

g) The plasma and blood cells were placed in a refrigerator at −80° C. for later use.

h) After the experiment was completed, all items were put in place, the lab bench was cleaned, the UV lamp of the biological safety cabin was switched on and then switched off after 30 minutes of irradiation. The detailed experiment records were recorded.

2. cfDNA Extraction i) The equipment, reagents, and consumables required for the experiment were prepared. A water bath was switched on and adjusted to the temperature of 60° C. A heating block was switched on and adjusted to the temperature of 56° C. It should be confirmed that the kit was within the expiration date, buffer ACB was added with an appropriate volume of isopropanol, buffer ACW1 and buffer ACW1 were added with an appropriate volume of ethanol (96-100%).

j) Recorded the sample number and other information.

k) If the plasma was fresh, cfDNA extraction was performed directly. If the plasma frozen at −80° C., thawed plasma tubes at room temperature. Centrifuged plasma samples for 5 min at 16,000×g and 4° C. temperature setting.

l) The required amount of ACL mixture was prepared according to Table 1.

TABLE 1

Volumes of Buffer ACL and carrier RNA (dissolved in Buffer AVE) required for processing 4 ml plasma

| The number of samples | Buffer ACL (ml) | carrier RNA in buffer AVE (μl) |
|---|---|---|
| 1 | 3.5 | 5.6 |
| 2 | 7.0 | 11.3 |
| 3 | 10.6 | 16.9 |
| 4 | 14.1 | 22.5 |
| 5 | 17.6 | 28.1 |
| 6 | 21.1 | 33.8 |
| 7 | 24.6 | 39.4 |
| 8 | 28.2 | 45.0 |
| 9 | 31.7 | 50.6 |
| 10 | 35.2 | 56.3 |
| 11 | 38.7 | 61.9 |
| 12 | 42.2 | 67.5 |
| 13 | 45.8 | 73.1 |
| 14 | 49.3 | 78.8 |
| 15 | 52.8 | 84.4 |
| 16 | 56.3 | 90.0 |
| 17 | 59.8 | 95.6 |
| 18 | 63.4 | 101.3 |
| 19 | 66.9 | 106.9 |

TABLE 1-continued

Volumes of Buffer ACL and carrier RNA (dissolved in Buffer AVE) required for processing 4 ml plasma

| The number of samples | Buffer ACL (ml) | carrier RNA in buffer AVE (μl) |
|---|---|---|
| 20 | 70.4 | 112.5 |
| 21 | 73.9 | 118.1 |
| 22 | 77.4 | 123.8 |
| 23 | 81.0 | 129.4 |
| 24 | 84.5 | 135.0 |

m) Pipetted 400 μl proteinase K into a 50 ml centrifuge tube containing 4 ml plasma, and vortexed intermittently for 30 s.

n) Added 3.2 ml Buffer ACL (containing 1.0 μg carrier RNA). Closed the cap and mixed by pulse-vortexing for 30 s. Make sure that a visible vortex forms in the tube. To ensure efficient lysis, it was essential that the sample and Buffer ACL were mixed thoroughly to yield a homogeneous solution.o) Note:

Did not interrupt the procedure at this time. Proceeded immediately to start the lysis incubation.

p) Incubated at 60° C. for 30 min·q) Added 7.2 ml Buffer ACB to the lysate in the tube. Closed the cap and mixed thoroughly by pulse-vortexing for 15 s·r) Incubated the lysate—Buffer ACB mixture in the tube for 5 min on ice or refrigerate.s) Assembling of a suction filtration device: Connected the QIAvac 24 Plus to a vacuum source. Inserted a VacValve into each luer slot of the QIAvac 24 Plus. Inserted a VacConnector into each VacValve. Placed the QIAamp Mini columns into the VacConnectors on the manifold. Finally inserted a tube extender (20 ml) into each QIAamp Mini column. Make sure that the tube extender was firmly inserted into the QIAamp Mini column to avoid leakage of sample. Note: the 2 ml collection tube was remained for the subsequent operation. Marked the sample number on the QIAamp Mini silica membrane column. VacValve ensured a steady flow rate. VacConnectors prevented direct contact between the spin column and VacValve during purification, thereby avoiding any cross-contamination between samples. The QIAamp Mini silica membrane column adsorbed DNA, and the tube extender could hold large volumes of plasma.

t) Carefully applied the lysate—Buffer ACB mixture into the tube extender of the QIAamp Mini column. Switched on the vacuum pump. When all lysates had been drawn through the columns completely, switched off the vacuum pump and opened the exhaust valve to release the pressure to 0 mbar. Carefully removed and discarded the tube extender.

u) Applied 600 μl Buffer ACW1 to the QIAamp Mini column. Closed the exhaust valve and switched on the vacuum pump. After all of Buffer ACW1 had been drawn through the QIAamp Mini column, switched off the vacuum pump and opened the exhaust valve to release the pressure to 0 mbar.

v) Applied 750 μl Buffer ACW2 to the QIAamp Mini column. Closed the exhaust valve and switched on the vacuum pump. After all of Buffer ACW2 had been drawn through the QIAamp Mini column, switched off the vacuum pump and opened the exhaust valve to release the pressure to 0 mbar.

w) Applied 750 μl ethanol (96-100%) to the QIAamp Mini column. Closed the exhaust valve and switched on the vacuum pump. After all of ethanol had been drawn through the QIAamp Mini column, switched off the vacuum pump and opened the exhaust valve to release the pressure to 0 mbar.

x) Closed the lid of the QIAamp Mini column. Removed it from the vacuum manifold, and discarded the Vac-Connector. Placed the QIAamp Mini column in a clean 2 ml collection tube, and centrifuged at full speed (20,000×g; 14,000 rpm) for 3 min.

y) Placed the QIAamp Mini Column into a new 2 ml collection tube. Opened the lid, and incubated the assembly at 56° C. for 10 min to dry the membrane completely.

z) Placed the QIAamp Mini column in a clean 1.5 ml elution tube (included in the kit), and discarded the 2 ml collection tube.

aa) Carefully applied 20-60 μl of nuclease-free water to center of the QIAamp Mini membrane. Closed the lid and incubated at room temperature for 3 min.

bb) Centrifuged in a microcentrifuge at full speed (20, 000×g; 14,000 rpm) for 1 min to elute the nucleic acids.

cc) Quality Standards and Evaluation

Qubit HS quantification: 1 μl of cfDNA was taken for quantitative determination using Qubit 4.0 (Thermo Fisher Scientific, Q33226) in combination with Qubit dsDNA HS Assay Kits (Thermo Fisher Scientific, Q32854), and the concentration was recorded as ng/μl.

Agilent 2100 detection: 1 μl of cfDNA was taken for cfDNA peak pattern detection using Agilent 2100 bioanalyzer (Agilent, G29939BA) in combination with Agilent High Sensitivity DNA Kit (Agilent, 5067-4626), to determine the distribution of cfDNA fragments.

dd) When all the experiment finished, cleaned the lab bench, switched on the UV lamp of the biological safety cabin and then switched off after 30 minutes of irradiation. Recorded the details of experiment.

Calculation of cfDNA concentration: Qublit concentration(ng/μl)*elution volume/plasma volume 3. cfDNA Library Construction ee) Preparation Before the Library Construction i. Take the magnetic beads (AMPureXP beads, Beckman) out of the refrigerator at 4° C. and incubated at room temperature for 30 minutes before use.

ii. Take End Repair & A-Tailing Buffer and End Repair reagent & A-Tailing Buffer enzyme mix out of the refrigerator at −20° C. and thawed on the ice box.

iii. Recorded the details about the name, sampling date, and DNA concentration on the experimental record books and numbered each sample.

iv. Take some 200 μl PCR tubes and marked with numbers (both the cap and the wall of the tube were labeled).

v. A volume of the DNA solution required for each cfDNA sample was calculated based on a standard of 10 ng≤X≤100 ng for an initial amount of cfDNA library construction, recorded on the experiment notebook, and the corresponding volume was taken and transferred to a 200 μl PCR tube.

vi. Added appropriate amount of nuclease-free water to each 200 μl PCR tube up to the final volume of 50 μl.

vii. Note: The following rules should be followed when preparing all reaction systems during the library construction process: if the number of samples was smaller than four, it was unnecessary to prepare a mixed system, and each sample was independently added with each component solution in the reaction system; if the number of samples was more than four, the mixed system was prepared by using 105% of the required amount of each component solution, and each component solution was added to each sample.

ff) End Repair & A-Tailing i. Prepare the end repair & A-Tailing reaction system according to Table 2.

TABLE 2

| Component | 1 reaction system | 8 reaction systems (excess 5%) |
|---|---|---|
| End Repair & A-Tailing Buffer | 7 μl | 58.8 μl |
| End Repair & A-Tailing enzyme mix | 3 μl | 25.2 μl |
| Total volume | 10 μl | 84 μl |

ii. 10 μl of the above-mentioned end repair reaction system was added to each 200 μl PCR tube, mixed well, and centrifuged at low speed. The thermocycler was set to perform the program as shown in Table 3.

TABLE 3

| Step | Temperature | Time |
|---|---|---|
| End Repair and A-Tailing | 20° C. | 30 min |
| | 65° C. | 30 min |
| HOLD | 4° C. | ∞ |

iii. The reaction system was taken out of the thermocycler and placed on the small yellow plate, and carried out an adapter ligation reaction.

Gg) Adapter Ligation Reaction System i. An adapter ligation reaction system was prepared according to Table 4.

TABLE 4

| Component | 1 reaction system | 8 reaction systems (excess 5%) |
|---|---|---|
| PCR-grade water | 5 μl | 42 μl |
| Ligation Buffer | 30 μl | 252 μl |
| DNA Ligase | 10 μl | 84 μl |
| Total volume | 45 μl | 378 μl |

ii. 45 μL of the above reaction system was added to each reaction tube, mixed gently, and centrifuged at low speed.

iii. Added an appropriate amount of adapter corresponding to the amount of input DNA. Adapter and insert molar ratio were as shown in Table 5. 5 μL of the adapter was added to each reaction tube. In addition, according to the sequencing requirements, each sample was added with a unique adapter, to avoid the situation that two samples using the same adapter occurred on the same lane. The information about the adapters used in each sample was well recorded.

TABLE 5

| Amount of insert DNA (Input DNA) (ng) | Molar concentration of adapter |
|---|---|
| X ≥ 50 ng | 15 μM |
| 15 ng ≤ X < 50ng | 7.5 μM |
| X ≤ 15 ng | 3 μM |

The above reaction system was mixed well and placed into the PCR amplifier, the temperature was set to be 20° C., and reacted for 15 min.

hh) DNA Purification i. Prepared 80% ethanol (for example, 50 mL of 80% ethanol: 40 mL of absolute ethanol+10 mL of nuclease-free water) before use.

ii. The corresponding number of 1.5 mL sample tubes was prepared and marked.

iii. The magnetic beads, which had been pre-equilibrated at room temperature, were fully vortexed and mixed, 88 μl of which was added into each tube.

iv. The above DNA mixture was mixed with the magnetic beads, and incubated at room temperature for 10 min.

v. The 1.5 mL tube was placed on the magnet to capture the magnetic beads until the liquid became clear.

vi. Carefully removed and discarded the supernatant, then added 200 μL of 80% ethanol into the tube. Rotated the tube 360 degrees horizontally and incubated the tube on the magnet at room temperature for 30 s, and then the supernatant was discarded. (During this process, the centrifuge tube had been kept on the magnet.)

vii. The above step were repeated once.

viii. Try to remove all residual ethanol without disturbing the beads. Opened the cap of the tube to dry the magnetic beads at room temperature and volatilized the ethanol, preventing the effect of the enzyme in the subsequent reaction system from being affected by the excess ethanol. Note: the magnetic beads should not be excessively dried, otherwise the DNA would not be easily eluted from the magnetic beads, resulting in yield loss. The drying should be stopped once the surface of the magnetic beads was no longer shiny.

ix. Added 21 μL of nuclease-free water into each sample tube to resuspend the magnetic beads, mixed well and incubated at room temperature for 5 min.

x. A new batch of 200 μL PCR tubes was prepared and marked with the corresponding sample number on the wall and cap of the tube.

xi. The tube was placed on the magnet to capture the magnetic beads until the solution was clear, then the supernatant was transferred to the corresponding PCR tube as a template for the PCR experiment.

ii) Library Amplification i. The library amplification reaction system was prepared according to Table 6.

TABLE 6

| Component | 1 reaction system | 8 reaction systems (excess 5%) |
|---|---|---|
| 2 × KAPA HiFi Hotstart ReadyMix | 25 μl | 210 μl |
| 10 × KAPA Library Amplification Primer mix | 5 μl | 42 μl |
| Total master mix volume | 30 μl | 252 μl |

ii. Added 30 μL of Pre-PCR amplification reaction system to each 0.2 mL PCR tube, mixed gently and centrifuged at low speed, and then placed in the thermocycler for reaction.

iii. The thermocycler was set as the following program, and the PCR cycles should be adjusted appropriately according to the amount of input DNA, as shown in Table 7.

TABLE 7

| Step | Temperature | Reaction time | Cycle number |
|---|---|---|---|
| Preliminary denaturation | 98° C. | 45 s | 1 |
| Denaturation | 98° C. | 15 s | Refer to the cycle number selection reference table for specific cycle number |
| Annealing | 60° C. | 30 s | |
| Elongation | 72° C. | 30 s | |
| Final elongation | 72° C. | 1 min | 1 |
| Storage | 4° C. | ∞ | 1 |

The selection of cycle number refers to Table 8.

TABLE 8

| Amount of Input DNA (ng) | PCR cycle |
|---|---|
| X > 50 ng | 4 |
| 25 ng < X ≤ 50 ng | 5 |
| 10 ng < X ≤ 25 ng | 6 |
| X ≤ 10 ng | 7 |

v. After the Pre-PCR reaction was finished, the library purification began.

jj) Library Purification i. The corresponding number of 1.5 mL sample tubes was prepared and marked accordingly.

ii. The magnetic beads, which had been pre-equilibrated at room temperature, were fully vortexed and mixed, 50 μL of which was added into each tube.

iii. The above-mentioned DNA mixture was mixed with the magnetic beads, and incubated at room temperature for 10 min.

iv. The 1.5 mL tube was placed on the magnet to capture the magnetic beads until the liquid became clear.

v. Carefully removed and discarded the supernatant, then added 200 μL of 80% ethanol into the tube. Rotated the tube 360 degrees horizontally and incubated the tube on the magnet at room temperature for 30 s, and then the supernatant was discarded. (During this process, the centrifuge tube had been kept on the magnet.)

vi. The above step were repeated once.

vii. Try to remove all residual ethanol without disturbing the beads. Unscrewed the cap of the tube to dry the magnetic beads at room temperature and volatilize the ethanol, preventing the effect of the enzyme in the subsequent reaction system from being affected by the excess ethanol. Note: the magnetic beads should not be excessively dried, otherwise the DNA would not be easily eluted from the magnetic beads, resulting in yield loss. The drying should be stopped once the surface of the magnetic beads was no longer shiny.

viii. 35 μL of nuclease-free water was added to each sample tube to resuspend the magnetic beads, mixed well and incubated at room temperature for 5 min.

ix. A new batch of PCR tubes was prepared, and marked with the item, sampling date, and sample name on the tube cap and marked with the adapter information, library construction date, and concentration on the tube wall.

x. The 1.5 mL sample tube was placed on the magnet to capture the magnetic beads until the solution was clear, then the supernatant was transferred to a new 1.5 mL tube with sample information.

xi. 1 μl of the library was taken for quantification using Qubit, and 1 μl of the library was taken for measuring the size of library fragments using Agilent 2100. The information was recorded.

xii. The samples were placed in the freezer boxes of the corresponding item and stored at −20° C.

xiii. After the experiment was completed, all items were put in place, the lab bench lab bench was cleaned, the UV lamp of the biological safety cabin was switched on and then switched off after 30 minutes of irradiation. The detailed experiment records were recorded.

4. Library Pooling kk) The equipment, reagents, and consumables needed for the experiment were prepared.

ll) A pooling volume of each sample was calculated according to the concentration of library and the sequence depth.

mm) A new 1.5 ml centrifuge tube was taken and labeled. Each sample was subjected to pooling in the same 1.5 ml centrifuge tube according to the calculated volume.

nn) After mixing thoroughly to yield a homogeneous solution, the concentration was measured, and the information is recorded.

oo) After the experiment was completed, all items were put in place, and the lab bench lab bench was cleaned.

5. Sequencing

The above pooled library was diluted and denatured with Tris-HCl and NaOH, and then sequenced.

6. Protein Quantification

Roche cobas e411 which was a electrochemistry luminescence automatic immunoassay analyzer was utilized to measure the concentration of plasma tumor markers following the manufacturer's instructions. The plasma tumor markers included CEA, AFP,CA-724,CA-199,CA-125,CA-153 and CYFRA. Used the reagents which was suitable for the instrument.

(1) Sample pretreatment: 500 μl of plasma was placed in a centrifuge, centrifuged at 1000 g for 1 min, then the supernatant was transferred to a labeled tube.

(2) The routine maintenance, calibration and quality control of the instruments were carried out regularly before sample testing. The instruments can be used for subsequent testing of sample only when the calibration and quality control were qualified.

(3) The sample was placed into the sample hole of the instrument, and the reagents required for the above 7 items were added into the reagent hole, the program was set up for detection, to obtain the quantitation of the above 7 kinds of proteins.

Example 2

The concentration of cfDNA was calculated based on the data obtained in the experimental process in Example 1: Qubit concentration (ng/μl)*elution volume/plasma volume. Some samples in Table 9 below are known types of samples, and the concentrations of cfDNA, which were measured according to the method in Example 1, are shown in Table 9 below.

TABLE 9

| Name of sample | Age | Gender | Category | cfDNA concentration (ng/μl) |
|---|---|---|---|---|
| S1 | 64 | M | Cancer | 121.275 |
| S2 | 53 | M | Cancer | 14.85 |
| S3 | 62 | M | Cancer | 14.83429 |
| S4 | 49 | F | Cancer | 10.9725 |
| S5 | 45 | F | Cancer | 11.5225 |
| S6 | 46 | F | Cancer | 9.515 |

TABLE 9-continued

| Name of sample | Age | Gender | Category | cfDNA concentration (ng/μl) |
|---|---|---|---|---|
| S7 | 70 | M | Cancer | 13.2 |
| S8 | 50 | F | Cancer | 6.947368 |
| S9 | 67 | F | Cancer | 10.83077 |
| S10 | 66 | F | Cancer | 17.20513 |
| S11 | 75 | M | Cancer | 10.35294 |
| S12 | 69 | F | Cancer | 11.0275 |
| S13 | 70 | M | Cancer | 10.84722 |
| S14 | 32 | M | Cancer | 9.364865 |
| S15 | 68 | M | Cancer | 28.875 |
| S16 | 66 | M | Cancer | 15.48684 |
| S17 | 58 | M | Cancer | 18.89744 |
| S18 | 71 | M | Cancer | 11.77 |
| S19 | 69 | M | Cancer | 18.61538 |
| S20 | 52 | M | Cancer | 65.71053 |
| S21 | 51 | M | Cancer | 6.757143 |
| S22 | 78 | M | Cancer | 9.9275 |
| S23 | 60 | F | Cancer | 9.033333 |
| S24 | 47 | M | Cancer | 11.20263 |
| S25 | 61 | F | Cancer | 17.36842 |
| S26 | 55 | F | Cancer | 8.077143 |
| S27 | 57 | F | Cancer | 8.687179 |
| S28 | 72 | F | Cancer | 25.1625 |
| S29 | 64 | F | Cancer | 29.8913 |
| S30 | 77 | F | Cancer | 9.9 |
| S31 | 69 | M | Cancer | 10.51111 |
| S32 | 72 | M | Cancer | 9.13 |
| S33 | 56 | M | Cancer | 13.26286 |
| S34 | 55 | M | Cancer | 11.935 |
| S35 | 67 | F | Cancer | 17.11111 |
| S36 | 43 | F | Cancer | 10.835 |
| S37 | 42 | F | Cancer | 77.34375 |
| S38 | 72 | F | Cancer | 13.34103 |
| S39 | 46 | M | Cancer | 9.13 |
| S40 | 64 | F | Cancer | 23.06944 |
| S41 | 37 | F | Cancer | 4.315385 |
| S42 | 56 | M | Cancer | 8.407143 |
| S43 | 44 | F | Cancer | 16.64103 |
| S44 | 66 | F | Cancer | 11.94286 |
| S45 | 55 | M | Cancer | 36.27027 |
| S46 | 57 | M | Cancer | 26.23077 |
| S47 | 66 | F | Cancer | 14.56757 |
| S48 | 63 | M | Cancer | 10.74615 |
| S49 | 56 | M | Cancer | 13.62778 |
| S50 | 75 | F | Cancer | 25.38462 |
| S51 | 50 | F | Cancer | 16.5 |
| S52 | 39 | F | Cancer | 31.02564 |
| S53 | 53 | F | Cancer | 13.8875 |
| S54 | 48 | M | Cancer | 8.926923 |
| S55 | 57 | F | Cancer | 10.83077 |
| S56 | 68 | F | Cancer | 14.38462 |
| S57 | 50 | F | Cancer | 8.525 |
| S58 | 67 | F | Cancer | 20.26316 |
| S59 | 69 | F | Cancer | 13.3375 |
| S60 | 51 | M | Cancer | 16.81429 |
| S61 | 55 | M | Cancer | 26.95 |
| S62 | 41 | M | Cancer | 19.9375 |
| S63 | 63 | F | Cancer | 37.23077 |
| S64 | 53 | F | Cancer | 90.60526 |
| S65 | 48 | M | Cancer | 28.63793 |
| S66 | 58 | M | Cancer | 12.88571 |
| S67 | 61 | M | Cancer | 10.23846 |
| S68 | 52 | M | Cancer | 12.32564 |
| S69 | 65 | F | Cancer | 14.17059 |
| S70 | 56 | M | Cancer | 7.497368 |
| S71 | 83 | F | Cancer | 52.46154 |
| S72 | 73 | M | Cancer | 4.34359 |
| S539 | 52 | F | Healthy | 14.14286 |
| S540 | 43 | M | Healthy | 6.294118 |
| S541 | 34 | F | Healthy | 6.625 |
| S542 | 37 | M | Healthy | 7.694444 |
| S543 | 44 | M | Healthy | 6.028571 |
| S544 | 37 | F | Healthy | 5.725 |
| S545 | 63 | M | Healthy | 13.2 |
| S546 | 30 | F | Healthy | 4.65 |
| S547 | 52 | F | Healthy | 7.7 |
| S548 | 50 | F | Healthy | 6.05 |

TABLE 9-continued

| Name of sample | Age | Gender | Category | cfDNA concentration (ng/μl) |
|---|---|---|---|---|
| S549 | 41 | M | Healthy | 11.175 |
| S550 | 80 | F | Healthy | 21.625 |
| S551 | 38 | M | Healthy | 14.60526 |
| S552 | 37 | F | Healthy | 12.175 |
| S553 | 39 | M | Healthy | 12.59375 |
| S554 | 40 | M | Healthy | 10.10256 |
| S555 | 39 | F | Healthy | 8.575 |
| S556 | 51 | M | Healthy | 7.37 |
| S557 | 43 | M | Healthy | 15.98667 |
| S558 | 39 | F | Healthy | 6.05 |
| S559 | 28 | F | Healthy | 4.3725 |
| S560 | 31 | F | Healthy | 5.335 |
| S561 | 31 | F | Healthy | 5.94 |
| S562 | 31 | F | Healthy | 7.92 |
| S563 | 31 | M | Healthy | 12.33333 |
| S564 | 29 | F | Healthy | 6.092308 |
| S565 | 47 | M | Healthy | 14.66667 |
| S566 | 43 | F | Healthy | 11.36667 |
| S567 | 36 | M | Healthy | 18.128 |
| S568 | 13 | F | Healthy | 10.945 |
| S569 | 56 | F | Healthy | 7.59 |
| S570 | 41 | M | Healthy | 5.94 |
| S571 | 37 | M | Healthy | 11.50541 |
| S572 | 54 | M | Healthy | 8.235897 |
| S573 | 40 | M | Healthy | 10.56 |
| S574 | 36 | M | Healthy | 11.13333 |
| S575 | 37 | F | Healthy | 9.2 |
| S576 | 50 | M | Healthy | 9.646154 |
| S577 | 46 | M | Healthy | 13.31579 |
| S578 | 53 | F | Healthy | 19.525 |
| S579 | 51 | F | Healthy | 8.4425 |
| S580 | 75 | F | Healthy | 7.728205 |
| S581 | 62 | M | Healthy | 25.88235 |
| S582 | 58 | F | Healthy | 16.92308 |
| S583 | 34 | M | Healthy | 13.62778 |
| S584 | 45 | M | Healthy | 21.26667 |
| S585 | 39 | M | Healthy | 19.8 |
| S586 | 72 | M | Healthy | 6.631429 |
| S587 | 73 | M | Healthy | 7.354286 |
| S588 | 62 | F | Healthy | 13.79714 |
| S589 | 64 | M | Healthy | 9.377049 |
| S590 | 61 | F | Healthy | 8.0025 |
| S591 | 63 | F | Healthy | 13.44444 |
| S592 | 36 | F | Healthy | 5.076923 |
| S593 | 41 | F | Healthy | 8.4975 |
| S594 | 41 | M | Healthy | 29.04 |
| S595 | 50 | F | Healthy | 7.8375 |
| S596 | 49 | M | Healthy | 10.53067 |
| S597 | 34 | M | Healthy | 10.24878 |
| S598 | 46 | F | Healthy | 19.61667 |
| S599 | 49 | M | Healthy | 14.75294 |
| S600 | 31 | M | Healthy | 10.15882 |
| S601 | 55 | F | Healthy | 7.766667 |
| S602 | 49 | M | Healthy | 13.53 |
| S603 | 67 | F | Healthy | 76.175 |
| S604 | 49 | M | Healthy | 17.13462 |
| S605 | 44 | F | Healthy | 8.158333 |
| S606 | 42 | F | Healthy | 12.15946 |
| S607 | 35 | F | Healthy | 15.95 |
| S608 | 25 | M | Healthy | 13.76571 |
| S609 | 49 | M | Healthy | 9.119355 |
| S610 | 55 | M | Healthy | 8.097222 |
| S611 | 43 | F | Healthy | 6.628947 |
| S612 | 42 | M | Healthy | 9.722581 |
| S613 | 53 | M | Healthy | 8.903125 |
| S614 | 53 | F | Healthy | 7.786842 |
| S615 | 64 | M | Healthy | 8.292308 |
| S616 | 51 | F | Healthy | 10.37949 |
| S617 | 75 | M | Healthy | 8.737143 |
| S618 | 29 | F | Healthy | 7.931579 |
| S619 | 34 | M | Healthy | 24.96154 |
| S620 | 32 | F | Healthy | 6.853846 |
| S621 | 60 | M | Healthy | 13.22973 |
| S622 | 47 | F | Healthy | 10.076 |
| S623 | 44 | M | Healthy | 18.66207 |
| S624 | 44 | M | Healthy | 9.8175 |

TABLE 9-continued

| Name of sample | Age | Gender | Category | cfDNA concentration (ng/μl) |
|---|---|---|---|---|
| S625 | 57 | M | Healthy | 6.2975 |
| S626 | 80 | M | Healthy | 11.31842 |
| S627 | 54 | F | Healthy | 7.2875 |
| S628 | 43 | M | Healthy | 11.93077 |
| S629 | 39 | F | Healthy | 5.838462 |
| S630 | 46 | M | Healthy | 11.36667 |
| S631 | 52 | F | Healthy | 18.7 |
| S632 | 44 | M | Healthy | 9.936667 |

Figure 3:
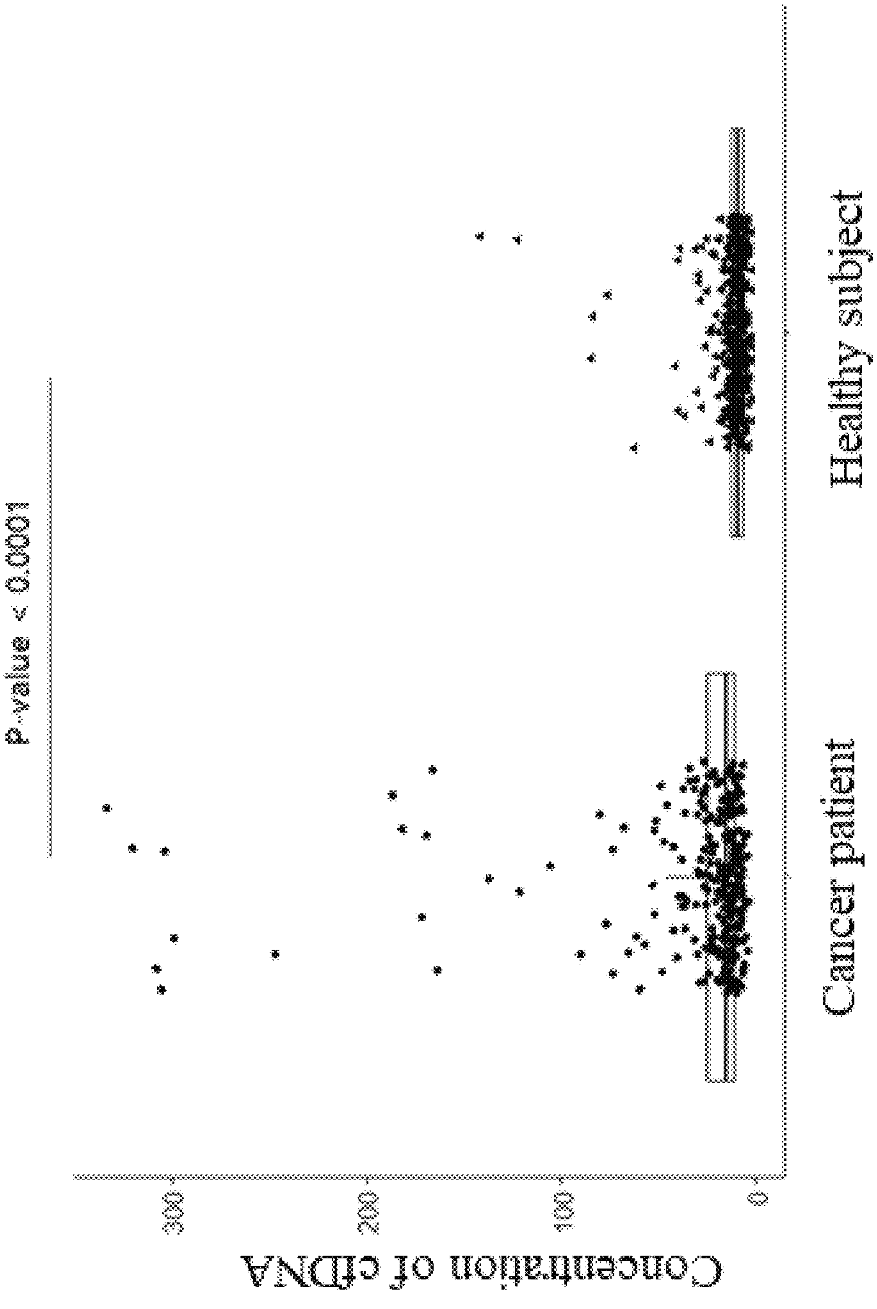
FIG. 3 shows a box plot comparing cfDNA concentrations between cancer patients and healthy subjects in Example 2 of the present disclosure.
Figure 4:
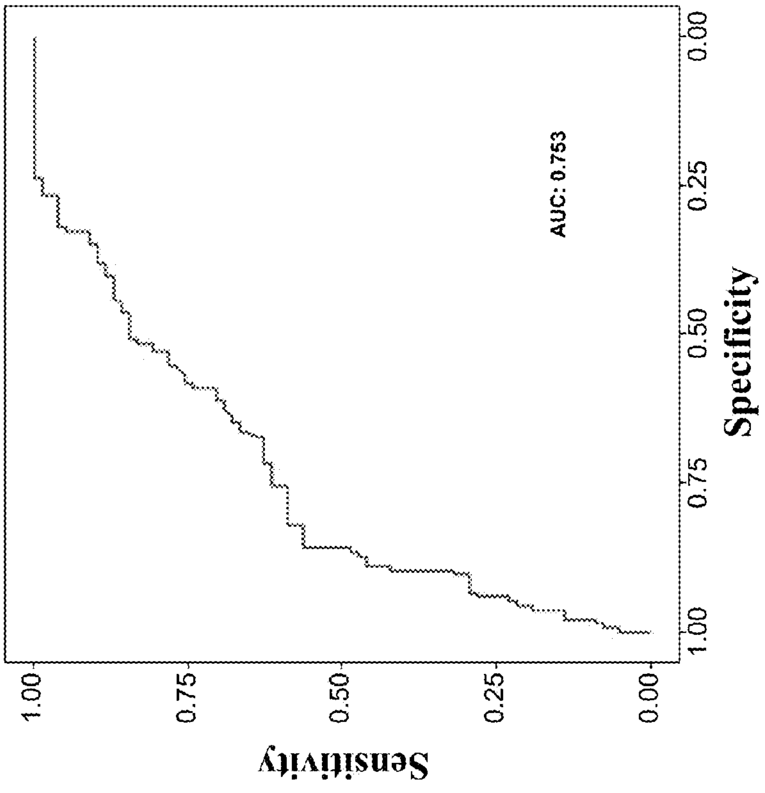
FIG. 4 shows a ROC curve graph obtained by plotting data in Table 9 in Example 2 of the present disclosure.

Through the t test, it was found that the concentrations of cfDNA in the tumor samples were significantly higher than those of healthy subjects in Table 9. FIG. 3 shows a box plot comparing the cfDNA concentrations of tumor samples and healthy samples. FIG. 4 shows a ROC curve graph obtained by plotting data in Table 9. The ROC curve graph proves that the cfDNA concentration can be adopted to help predict cancer.

Example 3

The protein quantification method in Example 1 was used to quantify the tumor markers. The expression levels of protein markers of some samples are shown in Table 10 below.

TABLE 10

| Name of sample | AFP | CEA | CA199 | CA125 | CA153 | CA211 | CA724 |
|---|---|---|---|---|---|---|---|
| S491 | 0.89 | 0.77 | 13.71 | 12.71 | 11.42 | 0.69 | 0.66 |
| S417 | 1.46 | 0.51 | 6.86 | 5.41 | 7.92 | 0.85 | 0.95 |
| S416 | 3.31 | 0.62 | 8.13 | 11.53 | 15.26 | 0.38 | 9.77 |
| S418 | 4.7 | 0.96 | 4.07 | 7.56 | 11.94 | 0.66 | 1.34 |
| S419 | 2.3 | 1.2 | 5.9 | 9.87 | 14.25 | 0.887 | 6.42 |
| S420 | 1.48 | 1.15 | 7.49 | 7.08 | 8.32 | 1.07 | 0.855 |
| S421 | 1.13 | 0.857 | 4.71 | 18.5 | 13.04 | 1.41 | 3.06 |
| S422 | 4.14 | 1.32 | 8.03 | 7.35 | 17.34 | 1.08 | 4.25 |
| S423 | 2.26 | 0.777 | 3.1 | 5.88 | 6.73 | 0.924 | 4.29 |
| S424 | 3.17 | 1.8 | 11.54 | 9.72 | 7.96 | 1.27 | 1.41 |
| S425 | 1.72 | 0.971 | 6.84 | 7.31 | 7.9 | 0.427 | 4.83 |
| S426 | 1.2 | 2.6 | 7.81 | 13.44 | 8.12 | 0.933 | 19.99 |
| S427 | 1.66 | 0.485 | 5.18 | 11.08 | 8.69 | 0.546 | 1.24 |
| S428 | 2.37 | 0.62 | 7.69 | 15.38 | 7.88 | 1.19 | 2.88 |
| S429 | 6.55 | 1.97 | 3.28 | 18.41 | 4.74 | 1.45 | 0.786 |
| S430 | 1.22 | 1.97 | 23.51 | 16.12 | 7.17 | 1.07 | 36.4 |
| S431 | 3.48 | 1.15 | 8.81 | 49.38 | 12.24 | 0.662 | 11.08 |
| S432 | 7.54 | 2.71 | 8.47 | 8.6 | 9.87 | 1.79 | 3.19 |
| S683 | 2.9 | 1.88 | 15.22 | 6.09 | 13.42 | 1.22 | 3.36 |
| S433 | 3.31 | 1.35 | 8.31 | 5.41 | 9.44 | 0.631 | 9.02 |
| S434 | 2.58 | 1.67 | 8.21 | 9.15 | 7.58 | 0.93 | 0.879 |
| S435 | 4.4 | 0.975 | 6.1 | 8.33 | 7.15 | 1.37 | 5.8 |
| S436 | 3.73 | 1.32 | 7.22 | 9.02 | 5.66 | 3.79 | 0.824 |
| S437 | 2.44 | 1.15 | 2.98 | 15.78 | 9.1 | 1.86 | 2.17 |
| S438 | 4.28 | 1.39 | 22.84 | 13.97 | 8.66 | 0.968 | 0.907 |
| S439 | 1.07 | 1.16 | 7.19 | 41.37 | 6.87 | 2.02 | 4.82 |
| S440 | 1.67 | 3.91 | 0.6 | 15.23 | 11.09 | 1.62 | 4.65 |
| S441 | 3.23 | 1.31 | 12.48 | 19.55 | 10.99 | 1.44 | 0.926 |
| S442 | 6.08 | 2.05 | 10.55 | 12.47 | 6.35 | 2.98 | 4.82 |
| S443 | 1.56 | 1.54 | 5.63 | 19.03 | 21.36 | 2.26 | 1.79 |
| S444 | 2.16 | 2.22 | 3.25 | 8.95 | 14.3 | 0.864 | 0.841 |
| S445 | 2.96 | 0.881 | 0.6 | 7.77 | 2.61 | 2.17 | 2.33 |
| S446 | 3.63 | 1.96 | 4.46 | 18.47 | 7.78 | 0.721 | 3.6 |
| S447 | 2.99 | 1.03 | 5.5 | 22.69 | 6.33 | 0.836 | 17.82 |
| S448 | 2.33 | 1.64 | 23.43 | 12.43 | 12.27 | 0.762 | 2 |
| S449 | 6.95 | 2.47 | 11.14 | 8.48 | 7.44 | 1.49 | 2.85 |
| S450 | 3.38 | 2.37 | 0.6 | 5.18 | 8.93 | 2.73 | 1.88 |
| S451 | 1.93 | 2.09 | 0.6 | 23.02 | 14.74 | 0.981 | 5.48 |
| S452 | 3.95 | 3.05 | 6.24 | 18.96 | 14.34 | 1.93 | 1.77 |
| S453 | 2.54 | 0.655 | 11.02 | 14 | 5.82 | 1.25 | 1.39 |
| S454 | 1 | 1.54 | 0.6 | 17.6 | 12.57 | 1.49 | 2.24 |

TABLE 10-continued

| Name of sample | AFP | CEA | CA199 | CA125 | CA153 | CA211 | CA724 |
|---|---|---|---|---|---|---|---|
| S455 | 8.93 | 0.857 | 6.43 | 14.68 | 5.02 | 1.92 | 0.716 |
| S456 | 2.02 | 2.13 | 6.04 | 7.59 | 10.81 | 1.06 | 1.43 |
| S488 | 1.73 | 6.27 | 3.95 | 8.27 | 14.02 | 1.59 | 0.919 |

The method for determining the content of protein tumor markers in the sample is as follows:

(I) Data filtering and preprocessing: for some of the missing data, the k-Means clustering algorithm was used to find samples closest to the sample with the missing value, and the mean of these samples was used as the missing value of the sample to polish the data.

(II) Data standardization processing:

The different quantitative methods and platforms of different protein markers may result in large differences in the range of protein expression. In order to eliminate such influence, the standardization method of Z-score was used to standardize the data.

(III) Establishing a model:

(1) Model selection and parameter optimization. Common classification algorithms in machine learning include: Bayesian model, decision tree, support vector machine, neural network, LASSO, etc.

(2) A cross-validation method was used. In this example, 10-fold cross-validation was used. For each classification method, the data set was divided into 10 parts sequentially, and 9 parts of them were randomly selected as the training set to construct the classification model, and the remaining 1 part served as a validation set data for validation, the above process was repeated. The ROC curve of each method on the prediction set was obtained, and independent hospital data was used for independent validation (to prevent the model from overfitting). Through comparison, LASSO was finally chosen as the classifier.

Figure 5:
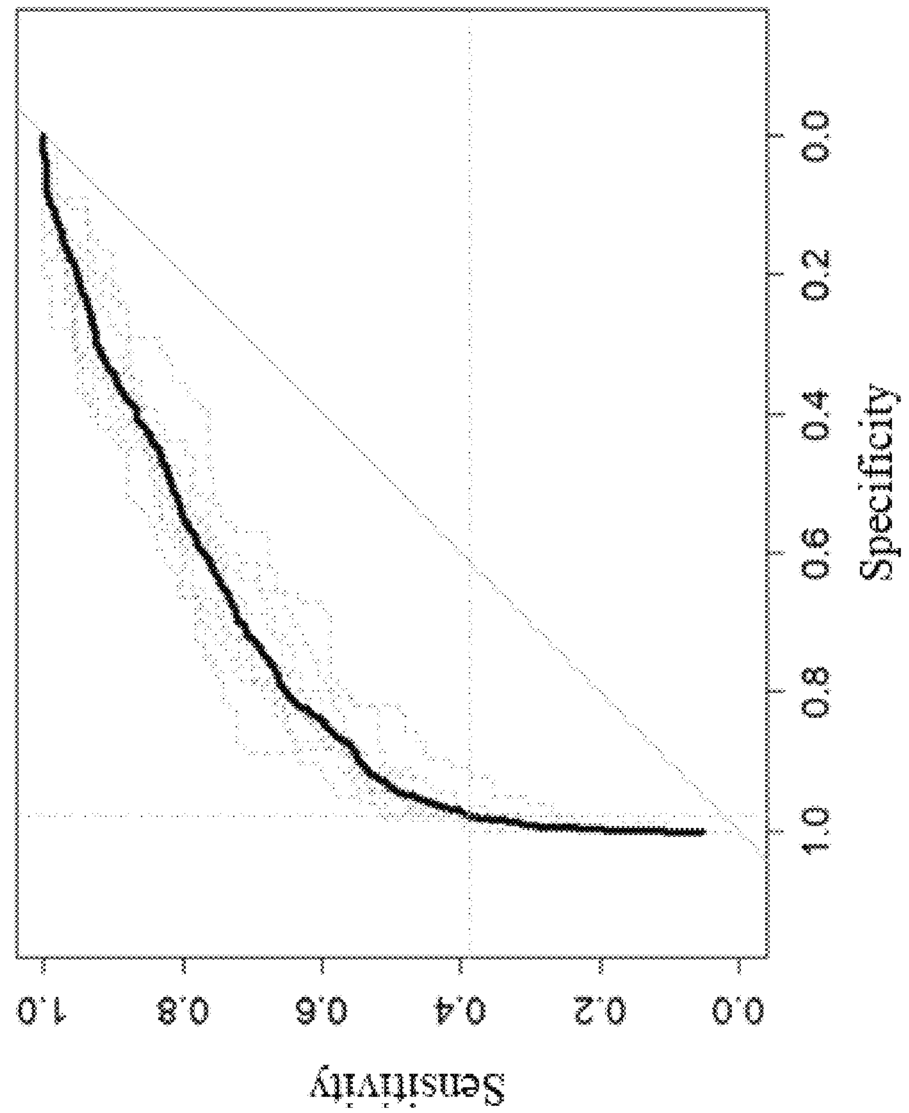
FIG. 5 shows ROC curve graph of LASSO 10-fold cross validation based on protein tumor markers established in Example 3 of the present disclosure.

(3) According to the selected model (LASSO), the optimal parameter and cut-off value were obtained by using the 10-fold cross-validation. Due to the low tumor incidence and the large population, the obtained cut-off value must be highly specific level, 98% specificity was finally selected as the cut-off value. The performance of cancer prediction model building by LASSO with 10-fold cross-validation was shown, as illustrated in FIG. 5. The black line showed the average results for the 10-fold cross-validation (4) The test data was preprocessed according to the above steps (1) and (2), and the model established in step (3) was used to predict a probability (p-value) that the sample is derived from a cancer patient. P-value>0.9 was an indicator that the sample is derived from a cancer patient.

Example 4

According to the method of Example 1, the library construction and sequencing of the samples were performed to obtain the off-machine data (1) After filtering out low-quality reads, an alignment software (bwa) was used to align these sequencing reads to the human reference genome (hg19).

(2) The mapping results were filtered, a mapping quality score was required to be greater than 30, and duplicate reads as well as reads that were not propre pair alignment, etc., were removed. Bedtools were used to count the reads number of each pre-defined bins.

(3) According to the reads count of each bins (for example: 1 kb, 5 kb, 10 kb, 20 kb, 30 kb, 50 kb, 100 kb, 200 kb, 300 kb, 500 kb, 1000 kb), the Akaike's information criterion and the cross-validation Log-likelihood were calculated (Gusnanto et al. (2014)). Finally, 100,000 bp was selected as the bin size.

(4) The reference genome was divided into bins, each of the bins was 100,000 bp, and the comparison reads of each bin were counted.

Figure 6:
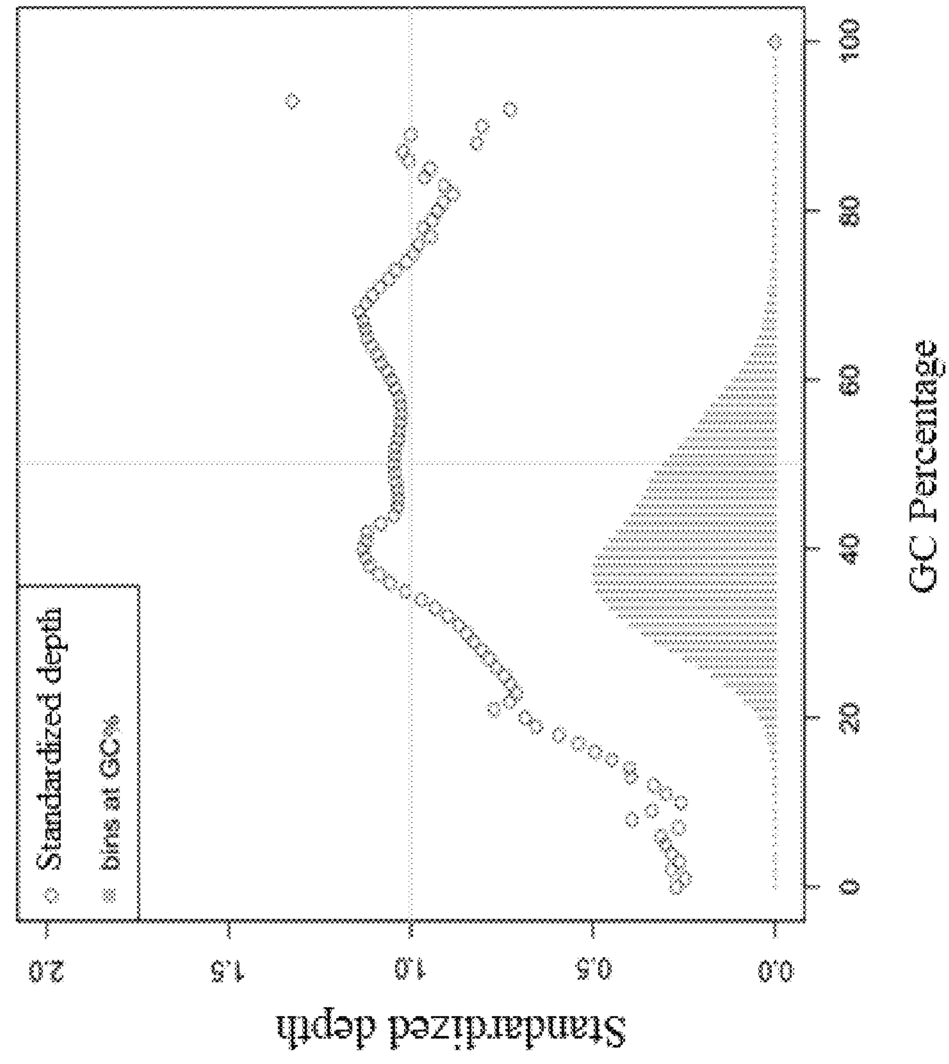
FIG. 6 shows a relationship between the number of reads and a GC content of bins of sample to be tested in Example 4 of the present disclosure.

(5) The filtering of bins includes: 1) mappability>0.5; 2) a ratio of N<0.5; 3) not in the region files wgEncodeDacMapabilityConsensusExcludable.bed and wgEncodeDukeMapabilityRegionsExcludable.bed downloaded from UCSC; 4) filtering out X and Y chromosomes; 5) using normal reference set, calculating the average reads count in each bins, and filter bins with more than 3 times the standard deviation of all bins;

(6) The number of reads of each sample was corrected by a length of bins (divided by a non-N ratio of the bin);

(7) Calculate GC ratio of each bin: the number of A, T, C, and G bases in each window (bin), and the number of G and C were counted. A proportion of GC was a ratio of GC of this window. FIG. 6 shows a relationship between the sequencing depth and GC ratio of the sample window to be tested and a GC ratio distribution diagram of the window.

(8) Mappability calculation: according to the ENCODE's mappability bigwig file downloaded from UCSC, the mappability of each region in the file was compared with the bin, and an average mappability of all regions in each bin was calculated as the mappability value of the bin.

(9) The bins with an abnormal number of reads were filter out: the bins of 1%-99% quantile were remained;

(10) The GC ratio and mappability of each bin were combined, the bins were grouped according to the combination thereof, and a median number of reads of all bins corresponding to each combination of GC and mappability.

(11) Using a generalized cross-validation method, the bins were divided into 10 parts on average, most parts (such as 9) of which were used to fit non-parametric regression curve by locally weighted scatterplot smoothing (LOESS), and the remaining 1 part was used as the test set to predict, calculate AIC, and the like.

After a fitted curve was established by LOESS, based on the GC ratio and mappability of each bin, the expected value of each bins was calculated by the fitted curve/formula. In order to calculate the adjusted value of each bin, the reads number of each bin (step 6) was divided by the expected value of the same bin, optionally was minus the expected value of the same bin, and add the median reads number of all bins.

(12) In a healthy sample, there is almost no change in CNV, and genetic CNV occurs randomly. In the normal population, the corrected depths at the same bin satisfy the normal distribution. Therefore, we sequenced and analyzed more than 300 normal populations using the same method, and calculate the mean and standard deviation (SD) of the normal distribution of each bin based on the population samples. Z-score of each bins was calculated by subtracting the mean value and dividing it by SD value. If the absolute value of the subject's Z-score was greater than 3, it was considered that this bin of the sample was missing or amplified in this region. The abnormal biomarkers were picked out, and log R ratio: log 2 of each bin to the reference set (reads of the sample to be tested/average number of reads in the reference set) was calculated for the test sample.

Furthermore, the chromosome instability index CIN score was calculated based on the following formula:

$$CIN\ \text{score} = \sum_{k=1}^{n} Ri * \frac{lk}{a} * fk * \text{abs}(\log R)$$

$$R_i = \begin{cases} 1 & \text{abs}(Z-\text{score}) > 3 \\ 0 & \text{abs}(Z-\text{score}) \le 3 \end{cases}$$

wherein n represents the number of all window sequences;

a represents a predetermined constant, which is dependent on a size of the window;

$l_k$ represents a length of the k-th abnormal window;

$f_k$ represents a probability that CNV occurs in the k-th abnormal window sequence;

Z-score represents an absolute value of a standard score of the k-th window;

abs(log R) represents an absolute value of log R ratio of the k-th window after smoothing.

Figure 7:
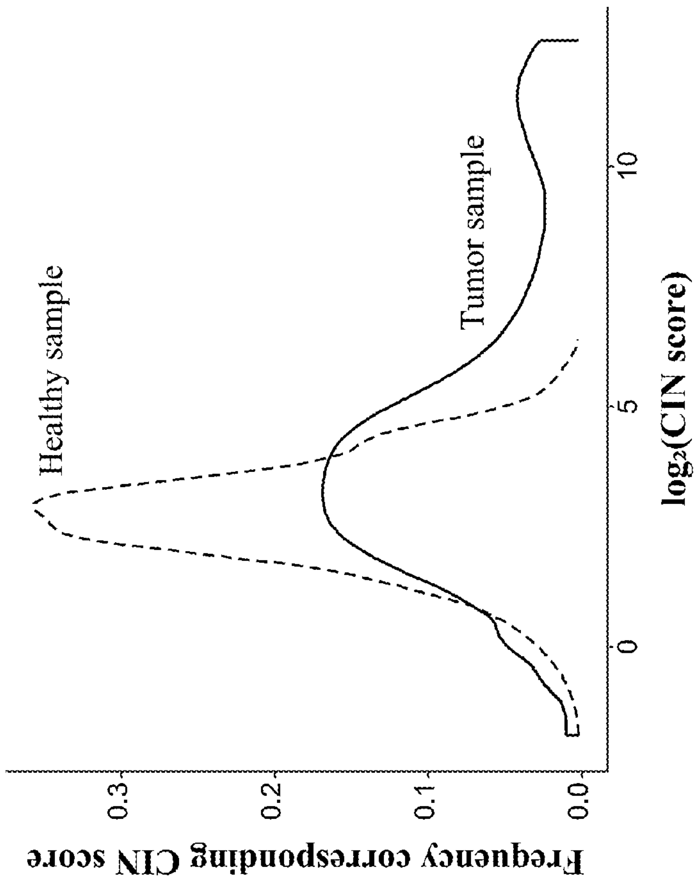
FIG. 7 shows a distribution of CIN values in cancer samples and healthy samples in Example 4 of the present disclosure.

FIG. 7 shows a distribution of CIN values in a liver cancer sample and a healthy sample in Example 4.

Example 5

Sequencing data was obtained according to Example 1, and filtering comparison results were obtained by following the steps (1) and (2) in Example 4.

(1) The total number of PE reads on the normal alignment of the sample. For example, S85 sample in the embodiment, the total number of reads: 17352335;

(2) Two paired reads were selected and aligned with the reference genome of the mitochondria (chrM) at the same time. The length of the insert was calculated, and the corresponding reads under different inserts were statistically analyzed. Table 11 below shows the statistical results of a sample of an example. The ratio of mitochondria DNA was calculated by dividing the total mitochondria DNA reads number of all fragment size by the total number of reads, and multiplying it by 1000000.

TABLE 11

| Length of FS | The number of reads |
|---|---|
| 69 | 1 |
| 70 | 1 |
| 72 | 7 |
| 73 | 7 |
| 74 | 11 |
| 75 | 9 |
| 76 | 7 |
| 77 | 9 |
| 78 | 5 |
| 79 | 9 |
| 80 | 9 |
| 81 | 13 |
| 82 | 9 |
| 83 | 13 |
| 84 | 13 |
| 85 | 7 |
| 86 | 16 |
| 87 | 11 |
| 88 | 15 |
| 89 | 10 |
| 90 | 12 |
| 91 | 10 |
| 92 | 11 |
| 93 | 12 |
| 94 | 11 |
| 95 | 4 |
| 96 | 12 |
| 97 | 13 |
| 98 | 18 |
| 99 | 10 |
| 100 | 10 |
| 101 | 11 |
| 102 | 7 |
| 103 | 13 |
| 104 | 7 |
| 105 | 7 |
| 106 | 10 |
| 107 | 11 |
| 108 | 12 |
| 109 | 15 |
| 110 | 10 |
| 111 | 14 |
| 112 | 11 |
| 113 | 9 |
| 114 | 13 |
| 115 | 18 |
| 116 | 7 |
| 117 | 11 |
| 118 | 4 |
| 119 | 16 |
| 120 | 8 |
| 121 | 8 |
| 122 | 12 |
| 123 | 9 |
| 124 | 6 |
| 125 | 14 |
| 126 | 14 |
| 127 | 10 |
| 128 | 7 |
| 129 | 15 |
| 130 | 9 |
| 131 | 13 |
| 132 | 9 |
| 133 | 6 |
| 134 | 7 |
| 135 | 12 |
| 136 | 9 |
| 137 | 11 |
| 138 | 9 |
| 139 | 10 |
| 140 | 13 |
| 141 | 6 |
| 142 | 13 |
| 143 | 10 |
| 144 | 6 |
| 145 | 7 |
| 146 | 8 |
| 147 | 3 |
| 148 | 12 |
| 149 | 12 |
| 150 | 10 |
| 151 | 6 |
| 152 | 11 |
| 153 | 8 |
| 154 | 11 |
| 155 | 3 |
| 156 | 11 |
| 157 | 10 |
| 158 | 5 |
| 159 | 10 |
| 160 | 4 |
| 161 | 7 |

TABLE 11-continued

TABLE 11-continued

| Length of FS | The number of reads |
|---|---|
| 162 | 10 |
| 163 | 10 |
| 164 | 8 |
| 165 | 4 |
| 166 | 7 |
| 167 | 6 |
| 168 | 4 |
| 169 | 7 |
| 170 | 8 |
| 171 | 10 |
| 172 | 8 |
| 173 | 8 |
| 174 | 5 |
| 175 | 4 |
| 176 | 10 |
| 177 | 8 |
| 178 | 9 |
| 179 | 7 |
| 180 | 5 |
| 181 | 9 |
| 182 | 6 |
| 183 | 4 |
| 184 | 5 |
| 185 | 4 |
| 186 | 5 |
| 187 | 7 |
| 188 | 4 |
| 189 | 10 |
| 190 | 6 |
| 191 | 5 |
| 192 | 5 |
| 193 | 3 |
| 194 | 1 |
| 195 | 7 |
| 196 | 8 |
| 197 | 7 |
| 198 | 6 |
| 199 | 6 |
| 200 | 4 |
| 201 | 5 |
| 202 | 6 |
| 203 | 3 |
| 204 | 8 |
| 205 | 11 |
| 206 | 7 |
| 207 | 5 |
| 208 | 7 |
| 209 | 4 |
| 210 | 3 |
| 211 | 3 |
| 212 | 2 |
| 213 | 4 |
| 214 | 7 |
| 215 | 10 |
| 216 | 2 |
| 217 | 5 |
| 218 | 5 |
| 219 | 8 |
| 220 | 3 |
| 221 | 6 |
| 222 | 3 |
| 223 | 6 |
| 224 | 2 |
| 225 | 3 |
| 226 | 4 |
| 227 | 2 |
| 228 | 3 |
| 229 | 3 |
| 230 | 6 |
| 231 | 6 |
| 232 | 3 |
| 233 | 2 |
| 234 | 5 |
| 235 | 5 |
| 236 | 2 |
| 237 | 2 |
| 238 | 7 |

TABLE 11-continued

| Length of FS | The number of reads |
|---|---|
| 239 | 2 |
| 241 | 5 |
| 242 | 5 |
| 243 | 4 |
| 244 | 3 |
| 245 | 2 |
| 246 | 1 |
| 247 | 4 |
| 248 | 3 |
| 249 | 3 |
| 250 | 4 |
| 251 | 2 |
| 252 | 3 |
| 255 | 3 |
| 256 | 1 |
| 257 | 2 |
| 258 | 2 |
| 259 | 1 |
| 260 | 2 |
| 261 | 2 |
| 263 | 4 |
| 264 | 1 |
| 265 | 3 |
| 267 | 3 |
| 268 | 2 |
| 269 | 2 |
| 270 | 3 |
| 271 | 1 |
| 272 | 3 |
| 273 | 3 |
| 274 | 2 |
| 275 | 1 |
| 276 | 2 |
| 277 | 2 |
| 279 | 1 |
| 280 | 2 |
| 282 | 2 |

Figure 8A:
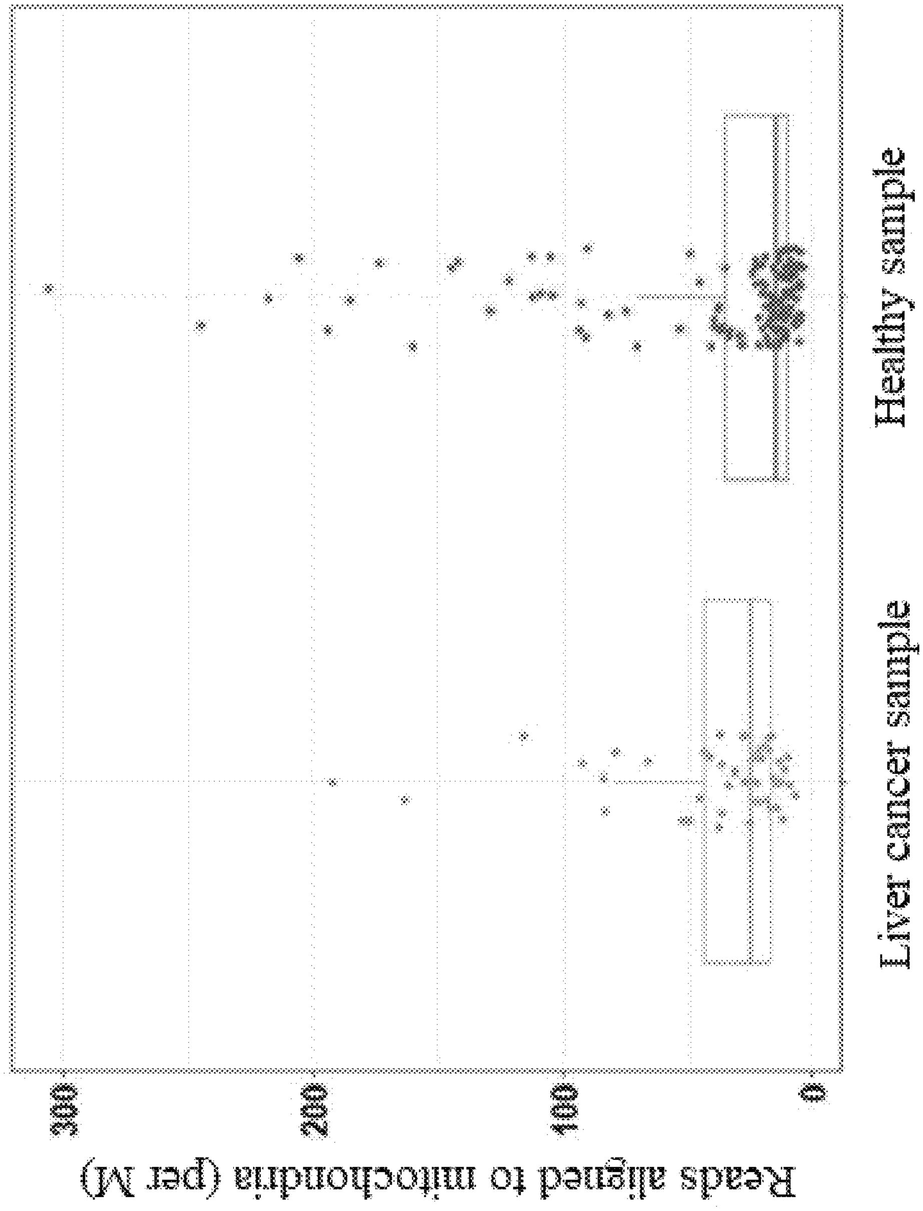
FIG. 8A shows all sequencing reads aligned to a mitochondrial reference genome (p-value=0.0004939)
Figure 8B:
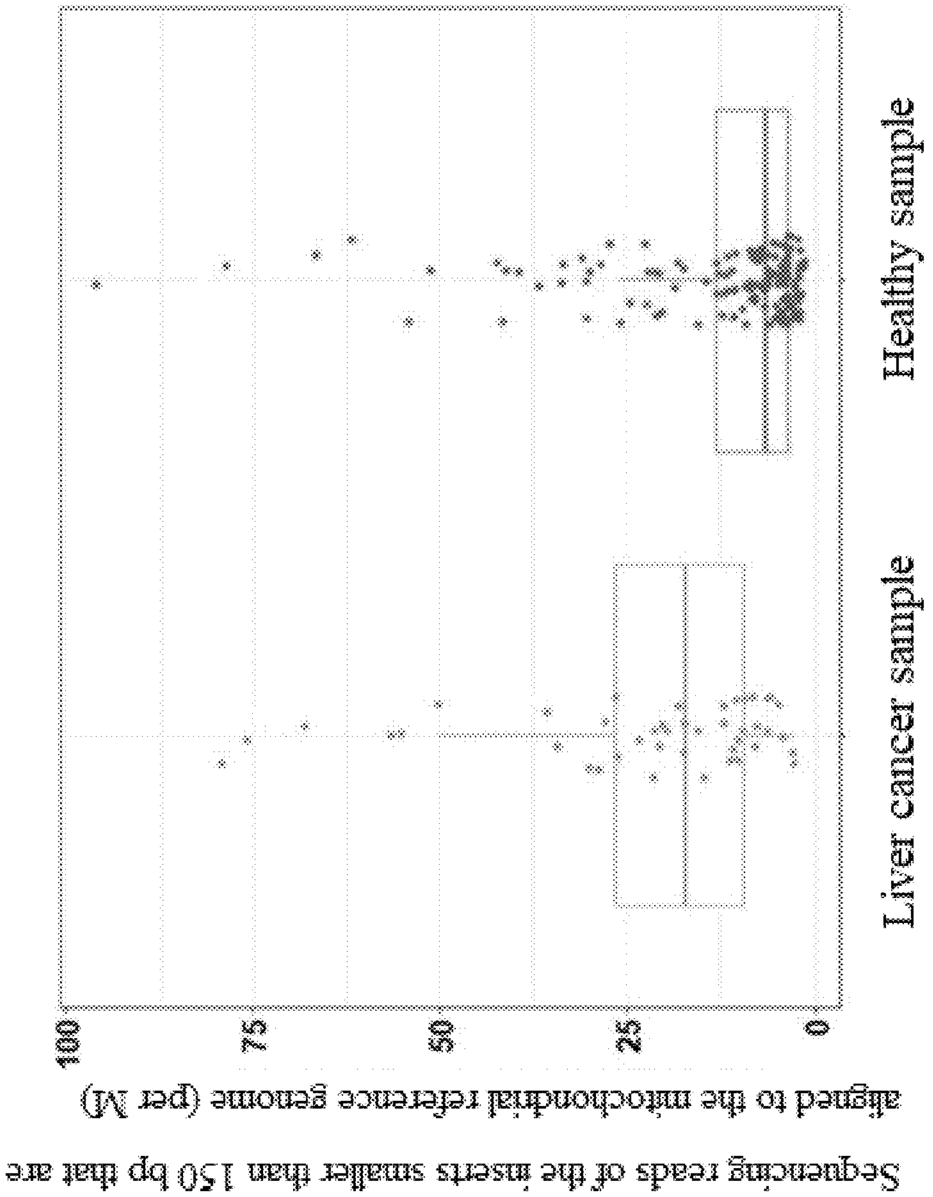
FIG. 8B shows sequencing reads aligned to a human mitochondrial reference genome and corresponding to inserts smaller than 150 bp (p-value=3.601e-06)

(3) The number of reads corresponding the insert with a length smaller than 150 bp was summed up. In the example, P150 of the S85 sample was 809 reads, which was divide by the total number of reads (17352335), and then multiplied by the 6th power of 10 to obtain a proportion of the mitochondria per M of reads. As shown in FIGS. 8A and 8B, the amount of mitochondrial DNA fragments is much higher in tumor samples than that in healthy samples, even more the difference between the hepatocellular Carcinoma samples and healthy samples is more significant among the mitochondrial DNA fragments below 150 bp.

Example 6

For the proper pair aligned reads with high alignment quality (>30), the fragment size of sequencing reads (FS) (a distance between two ends of the reads normally aligned on the chromosome) were statistically analyzed. The ratios of FS in 30-100 bp, 180-220 bp, and 250-300 bp were obtained, and were labeled as P100, P180, and P250. P100 represents a ratio of the number of sequencing reads with FS within 30-100 bp in the sample to the total number of sequencing reads with all FS; P180 represents a ratio of the number of inserts of 180 to 220 bp in the sample to the total number of sequencing reads with all FS; and P250 represents a ratio of the number of inserts of 250 to 300 bp in the sample to the total number of sequencing reads with all FS.

Figure 9:
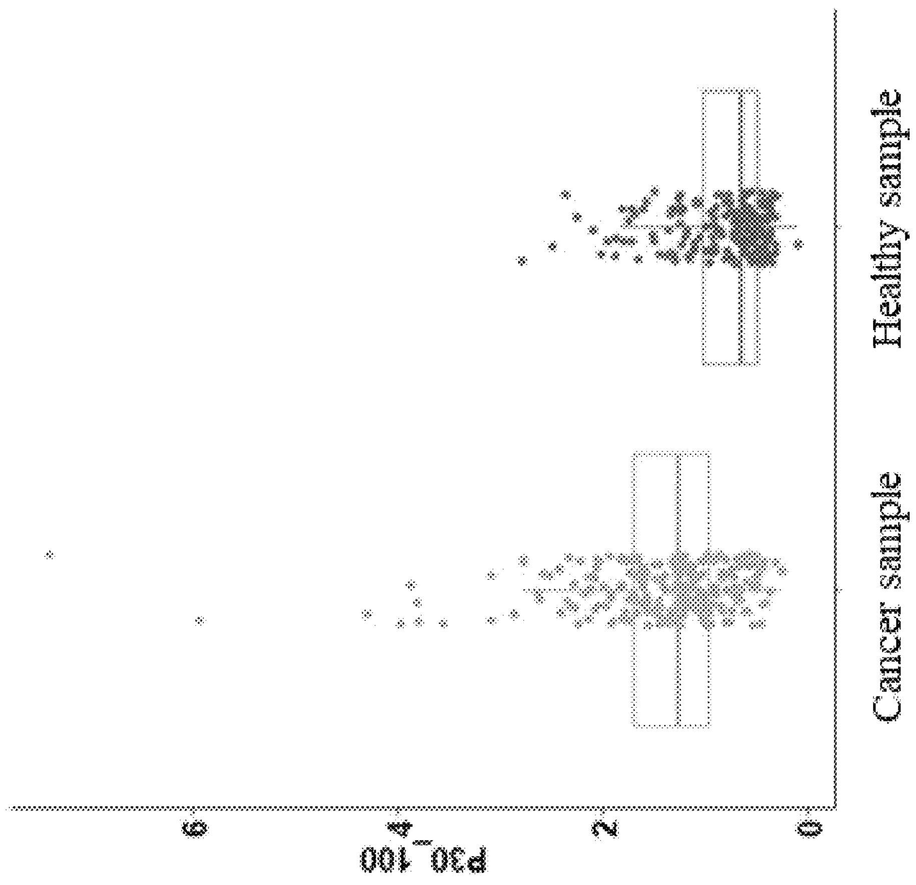
FIG. 9 shows a box plot comparing P100 between cancer samples and healthy samples in Example 6 of the present disclosure.
Figure 10:
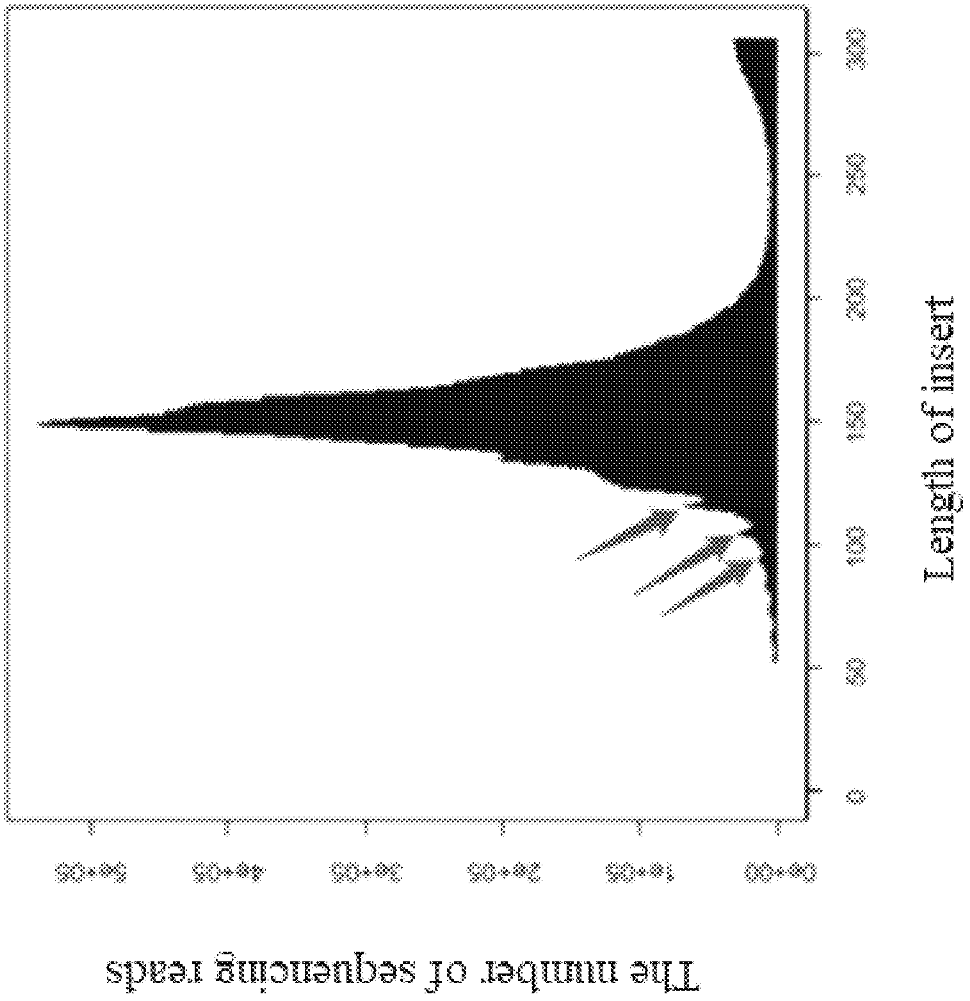
FIG. 10 shows a distribution diagram of insert lengths of sequencing reads of a sample in Example 6 of the present disclosure.

FIG. 9 shows difference between P100 of the cancer sample and P100 of the healthy sample, and the box distinguishability of the cancer sample and the healthy sample is good. As shown in FIG. 10, in the section smaller than 150 bp, there are small peaks and valleys (indicated with the arrows), and the positions of the peaks and valleys are the same for different samples. Therefore, the difference between the peak (the peaks respectively corresponding the insert lengths of 81 bp, 92 bp, 102 bp, 112 bp, 122 bp, 134 bp) and the corresponding valley (the peaks respectively corresponding the insert lengths of 84 bp, 96 bp, 106 bp, 116 bp, 126 bp, 137 bp) was calculated. A sum of the 6 differences was calculated and named as the "peak-valley spacing". Together with the highest peak value (peak), the final sample statistics are shown in Table 12 below.

At the same time, the entire genome was evenly split into regions (bins), wherein each bin has a size of 100 kb. The number of reads with FS ranging from 100 to 150 bp in each bin was counted and recorded as "the number of short fragments". Meanwhile, the number of reads with FS ranging from 151 to 220 bp in each bin was counted and recorded as "the number of long fragments". Since the GC content and mappability of each region are different, the number of short fragments and the number of long fragments were corrected by using locally weighted non-parametric regression parameters (LOESS).

The specific process was as follows: 1) the filtering of bins includes: 1) mappability>0.6; 2) a ratio of N<0.5; 3) not in the region files wgEncodeDacMapabilityConsensusExcludable.bed and wgEncodeDukeMapabilityRegionsExcludable.bed downloaded from UCSC; and 4) filtering out X and Y chromosomes;

Calculate the GC ratio of each bin: the number of A, T, C, and G bases in each window (bin), and the number of G and C were counted. A proportion of GC was the GC ratio of this window.

Mappability calculation: according to the ENCODE's mappability bigwig file downloaded from UCSC, the mappability of each region in the file was compared with the bin, and an average mappability of all regions in each bin was calculated as the mappability value of the bin.

Each bin's reads count was corrected by the length of bins (divided by a non-N ratio of the bin).

The GC and mappability of each bin were combined, the bins were grouped according to the combination thereof, and a median number of reads of all bins corresponding to each combination of GC and mappability.

Using the LOESS method, a fitted curve of the GC and mappability with respect to the number of long fragments or the number of short fragments was established. Finally, for each bin, according to its corresponding GC content and mappability, as well as the above fitted curve, the expected number of fragments corresponding to this bin was calculated, and subtract the expected number of fragments from the statical number of fragments in this bin, to obtain a fragment number residual error.

The median value of the numbers of long fragments or short fragments of all bins plus the residual error as the final corrected value of this bin. The corrected number of long fragments and the corrected number of short fragments for every 5M region were calculated by adding up the adjacent bins.

Figure 11:
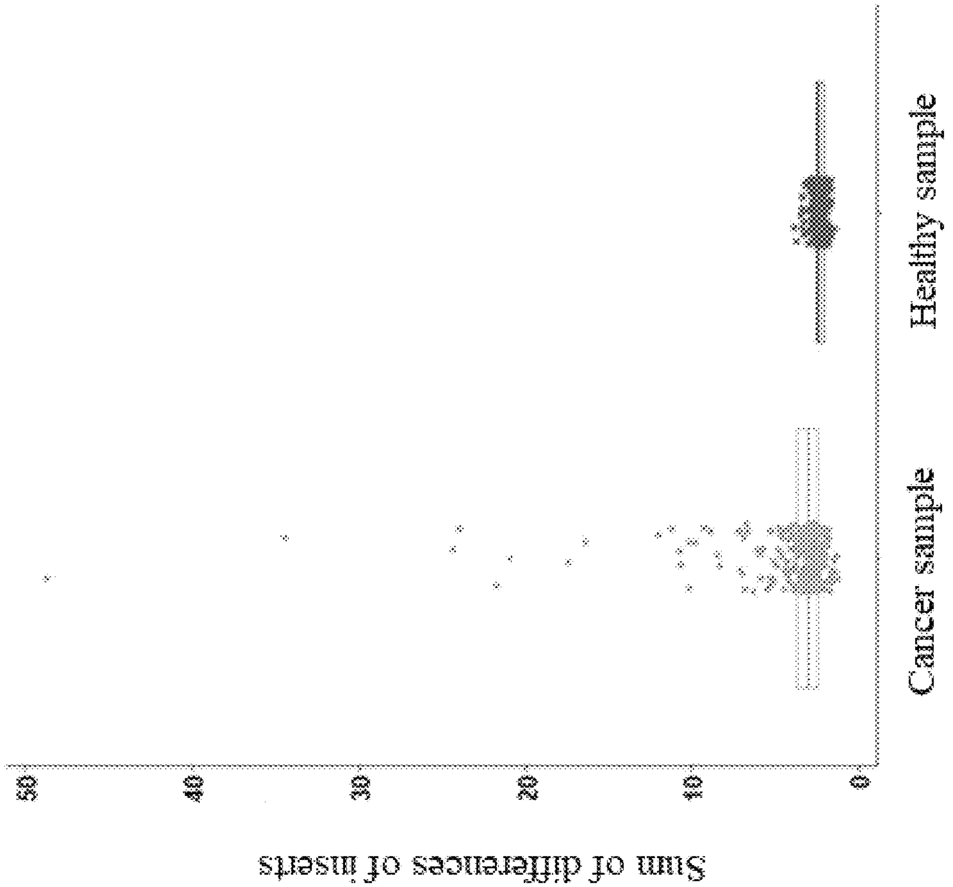
FIG. 11 shows a box plot comparing a sum of deviations of DNA fragment size between cancer samples and a healthy sample in Example 6 of the present disclosure.

Based on the number of short/long fragments in each 5M bin of the healthy sample, the bins were filtered to remove the bins wherein the number of short/long fragments was significantly greater than 3 times the standard deviation, and finally 537 5M bins were obtained;

After the filtering, for each bin, the number of short fragments was divided by the number of long fragments to obtain a fragment ratio of each bin. Use the fragment ratio of each bin minus the median fragment ratio of all bins to obtain the deviation value of each bin. FIG. 11 shows the difference in the sum of absolute deviations between cancer and healthy samples, wherein t-check value=8.385e-10 is very close to 0, which substantiates an extremely significant difference between the two groups.

TABLE 12

| Name of sample | Category | Peak | P30__100 | P180__220 | P250__300 | Sum of deviation | Peak-valley spacing |
|---|---|---|---|---|---|---|---|
| S210 | Cancer | 165 | 2.315645 | 8.054228 | 1.320913 | 10.04302 | 0.010169098 |
| S211 | Cancer | 166 | 0.456029 | 16.19036 | 2.707564 | 3.096699 | 0.005471189 |
| S212 | Cancer | 167 | 0.503086 | 30.41598 | 2.500817 | 1.844312 | 0.002993314 |
| S213 | Cancer | 167 | 0.844651 | 25.29735 | 2.655435 | 2.201456 | 0.004261916 |
| S214 | Cancer | 166 | 1.018736 | 21.73228 | 2.143146 | 2.90769 | 0.003729685 |
| S215 | Cancer | 166 | 1.080406 | 21.63758 | 2.099728 | 2.182167 | 0.004890386 |
| S216 | Cancer | 166 | 1.069949 | 24.62631 | 5.072727 | 4.104673 | 0.001453103 |
| S217 | Cancer | 167 | 0.348934 | 27.24379 | 2.901098 | 1.746068 | 0.001822744 |
| S218 | Cancer | 166 | 0.314705 | 17.86381 | 3.237715 | 3.737518 | 0.000783877 |
| S221 | Cancer | 165 | 2.859735 | 8.345068 | 1.245577 | 5.332014 | 0.010553492 |
| S222 | Cancer | 166 | 1.152311 | 25.33599 | 2.318476 | 6.315077 | 0.006230628 |
| S228 | Cancer | 166 | 1.690331 | 19.57347 | 1.271507 | 2.52441 | 0.007977815 |
| S229 | Cancer | 167 | 1.819507 | 24.60147 | 1.293839 | 2.302259 | 0.005540557 |
| S230 | Cancer | 166 | 2.087216 | 15.34641 | 1.634575 | 4.509792 | 0.00920506 |
| S231 | Cancer | 166 | 1.111094 | 22.25734 | 2.624453 | 2.640314 | 0.003230234 |
| S232 | Cancer | 166 | 3.088389 | 22.14669 | 1.510212 | 2.65005 | 0.002499495 |
| S233 | Cancer | 166 | 1.355747 | 20.8994 | 2.021902 | 2.322237 | 0.006909842 |
| S234 | Cancer | 167 | 0.948446 | 32.85803 | 2.349009 | 6.324849 | 0.001589768 |
| S235 | Cancer | 166 | 1.003579 | 32.32253 | 1.662046 | 3.81569 | 0.002485458 |
| S237 | Cancer | 144 | 4.297873 | 5.603833 | 2.901886 | 29.42372 | 0.018844461 |
| S238 | Cancer | 166 | 1.385965 | 18.71572 | 2.169172 | 2.659369 | 0.004772947 |
| S239 | Cancer | 166 | 3.878012 | 21.2239 | 2.884815 | 2.674544 | 0.004773638 |
| S241 | Cancer | 166 | 2.427847 | 21.70032 | 2.116907 | 2.901248 | 0.010933864 |
| S242 | Cancer | 166 | 1.201897 | 17.78429 | 1.750792 | 3.061563 | 0.003190285 |
| S243 | Cancer | 165 | 5.941186 | 7.908763 | 5.624477 | 7.57841 | 0.006758634 |
| S247 | Cancer | 167 | 1.066165 | 25.02422 | 1.846463 | 2.246755 | 0.005506077 |
| S248 | Cancer | 167 | 1.136892 | 25.1564 | 2.279553 | 2.407249 | 0.00445302 |
| S249 | Cancer | 166 | 2.170735 | 17.87361 | 2.802181 | 3.242749 | 0.006827185 |
| S315 | Normal | 168 | 0.630463 | 27.37159 | 3.027791 | 2.069612 | 0.004466266 |

TABLE 12-continued

| Name of sample | Category | Peak | P30__100 | P180__220 | P250__300 | Sum of deviation | Peak-valley spacing |
|---|---|---|---|---|---|---|---|
| S317 | Normal | 167 | 0.357245 | 30.09416 | 2.88503 | 1.79331 | 0.002143698 |
| S319 | Normal | 167 | 0.51044 | 24.19926 | 2.051964 | 1.965036 | 0.003368073 |
| S320 | Normal | 167 | 0.362755 | 25.90924 | 2.708014 | 2.04104 | 0.002048851 |
| S321 | Normal | 166 | 0.570164 | 22.99946 | 1.961744 | 1.991931 | 0.003484679 |

Figure 12:
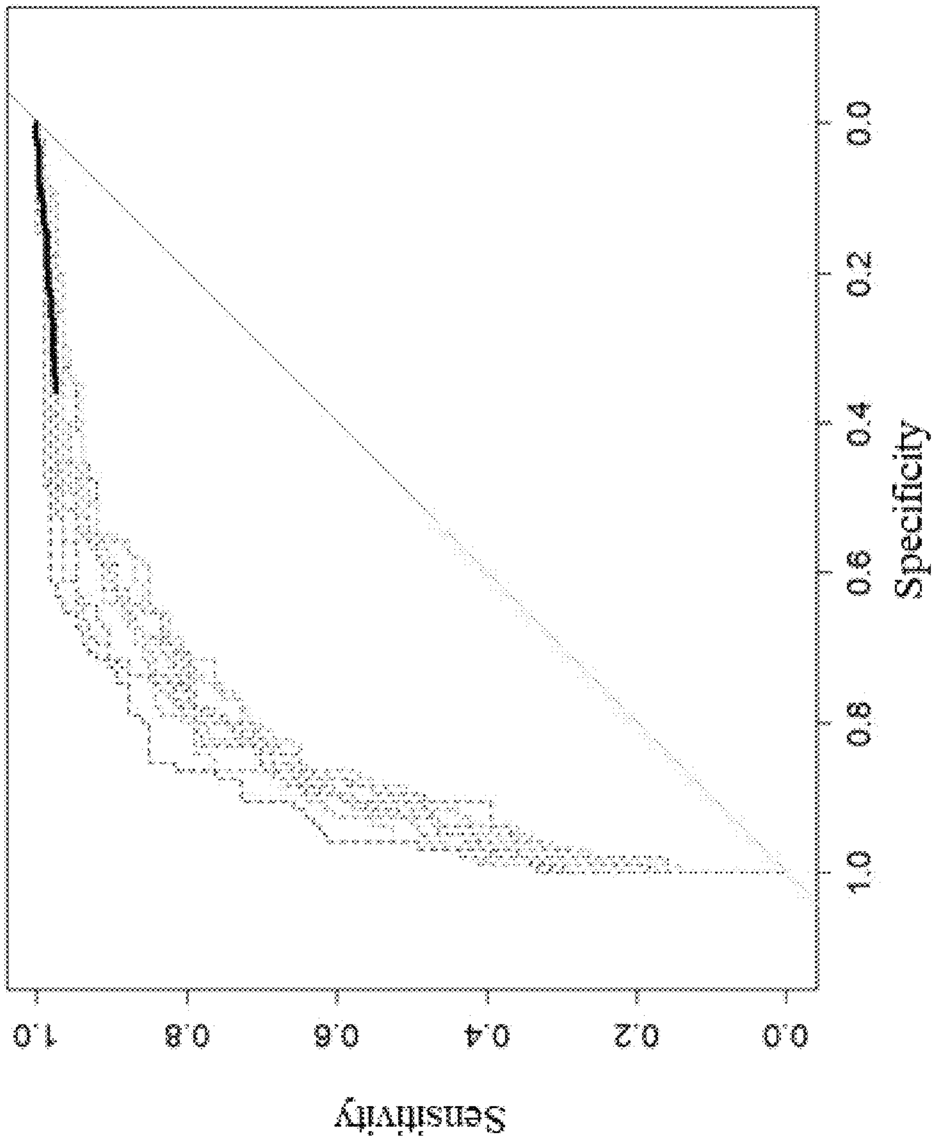
FIG. 12 shows a ROC curve graph of a 10-fold cross validation model used in Example 6 of the present disclosure.

The statistical values, such as the sum of the differences, the ratio of the FS in a range of 30-100 bp, the ratio of the FS in a range of 180-220 bp and the ratio of FS in a range of 250-300 bp, the length of the FS corresponding to the highest peak of the FS, and the sum of the difference between FS smaller than 150 bp at a peak and inserts smaller than 150 bp at a valley, were standardized and input as characteristic vectors. By using machine learning methods (such as SVM, Lasso, GBM), and based on 475 cancer samples and healthy samples, the effect of tumor prediction was test with the 10-fold cross-validation. The samples were divided into 10 parts on average, 9 parts of which were used as the training set to establish a tumor prediction model, and the remaining 1 part was used as a training set to measure the prediction performance of the model. The AUC value for each test set (defined as the area enclosed by the ROC curve and the coordinate axis), as illustrated in FIG. 12. The average AUC value of the model of the LASSO method was 0.845.

Figure 13:
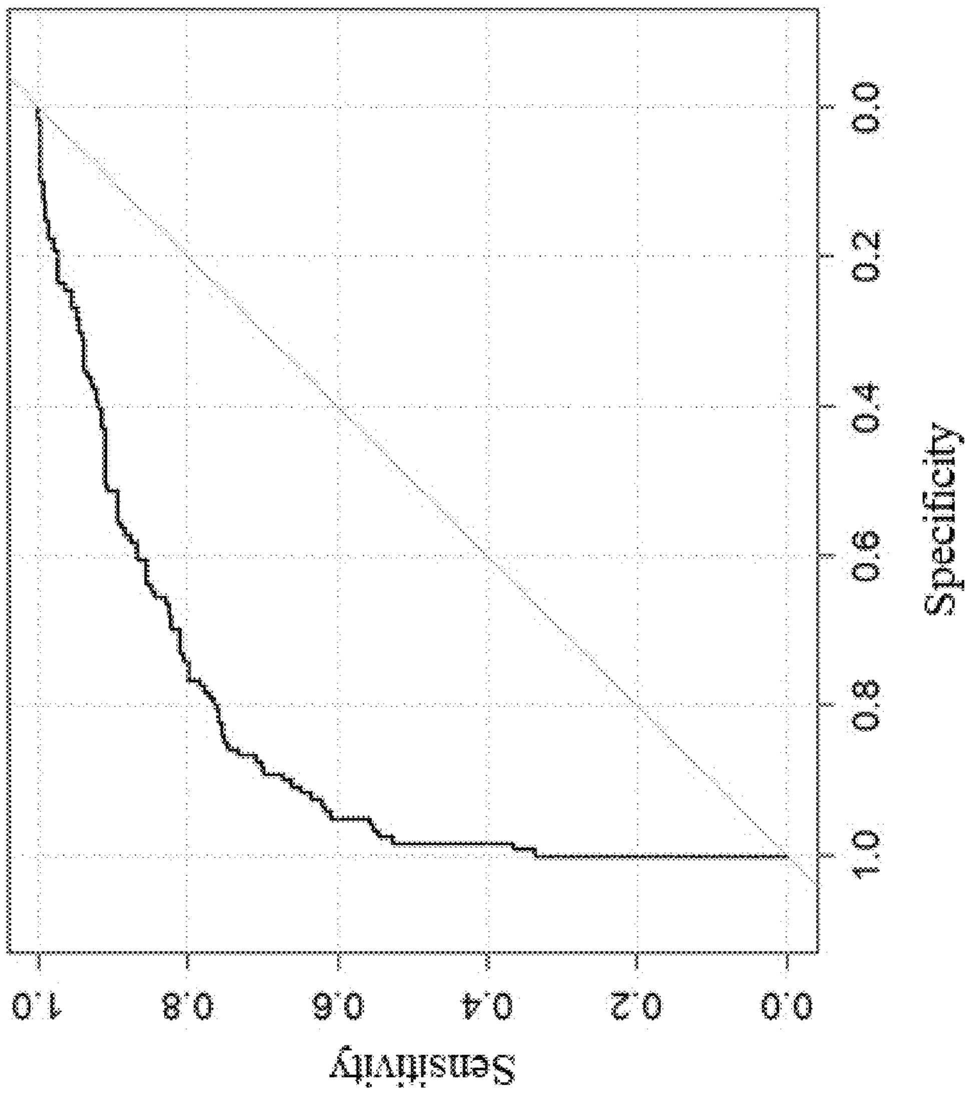
FIG. 13 shows a ROC curve graph of the third-party data set validation model in Example 6 of the present disclosure.

Based on the model selected above, a prediction model was constructed, and a third-party independent verification sample was used for tumor prediction, in order to determine the probability that the samples were derived from cancer patients. See FIG. 13 for details. The AUC value was 0.859, which proves that the model can still maintain high stability corresponding to different data sets, and the model is not easy to overfit. Finally, based on the ROC curve, the p-value corresponding 95% specificity was taken as a cut-off value: 0.40.

Example 7

The cfDNA concentration, log R ratio during a CIN mutation detection process, the expression levels of protein tumor markers, the ratio of P100, etc., as well as the finally calculated probability that the sample to be tested is derived from the tumor sample, are all related to the content of tumor cfDNA. The higher the tumor content, the stronger these signals.

Figure 14A:
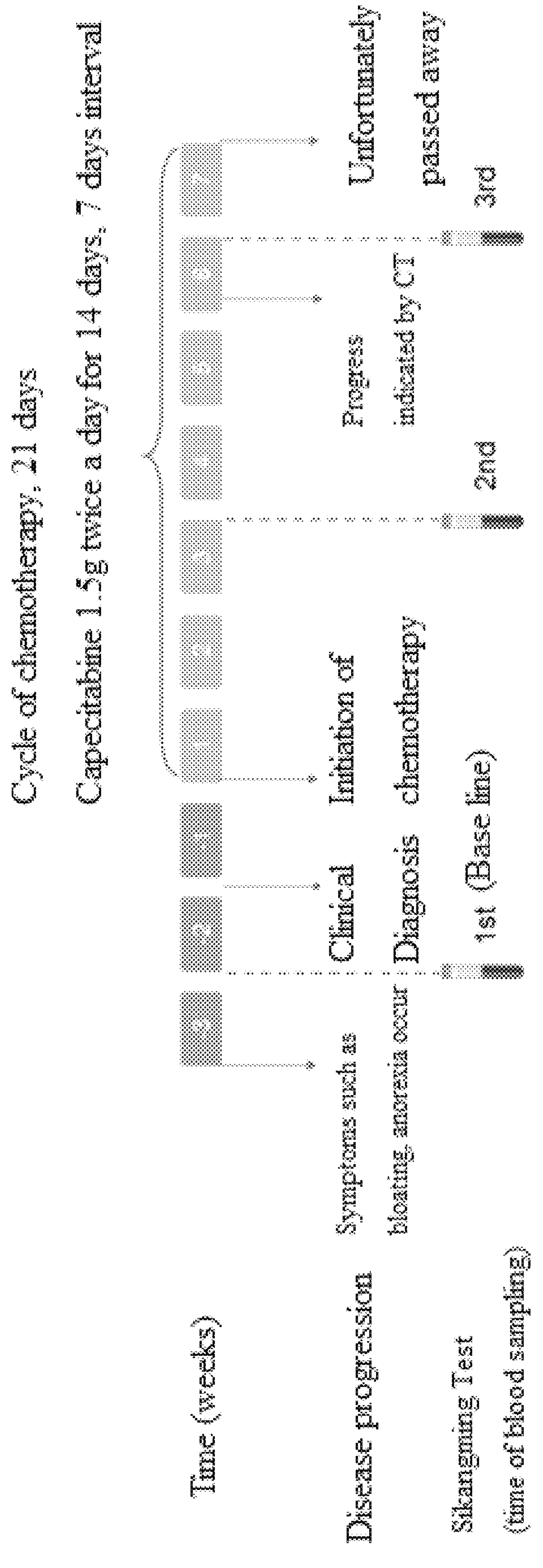
FIG. 14A shows sampling time, treatment and disease progression of Example 8.
Figure 14B:
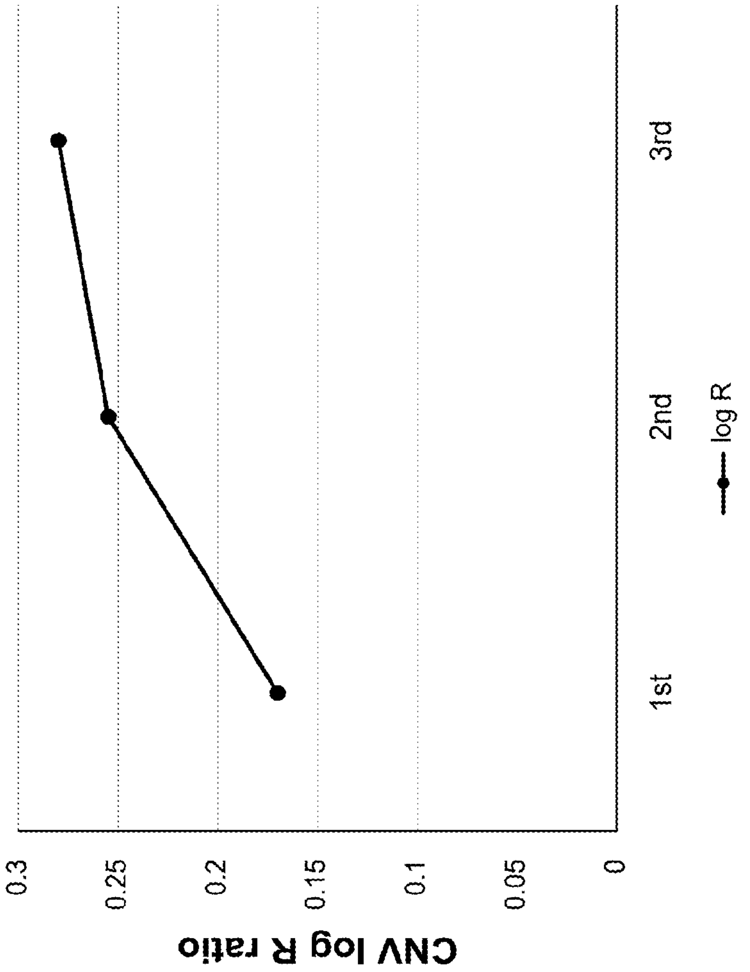
FIG. 14B shows a continuous change of an absolute median difference of CNV log R ratio.
Figure 14C:
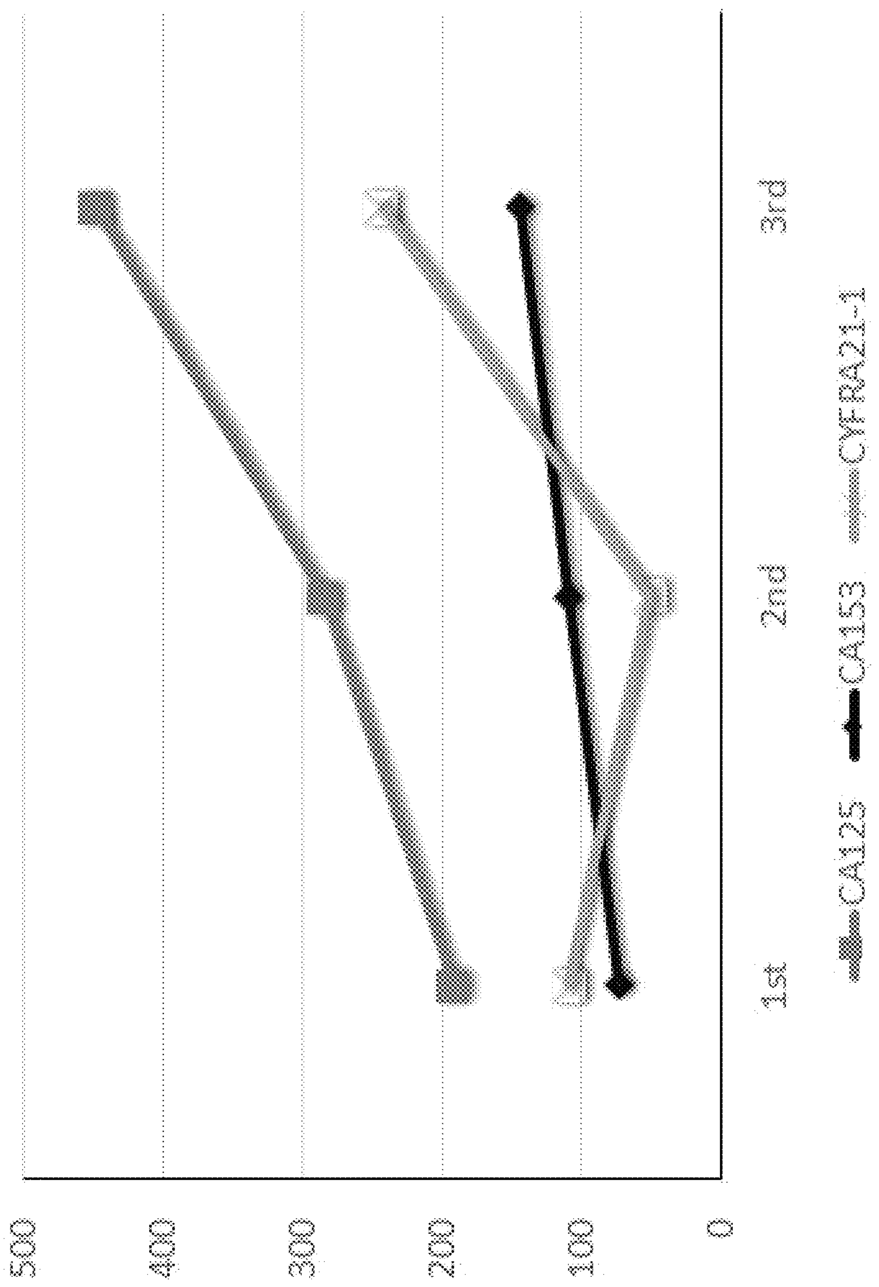
FIG. 14C shows changes in protein expression of three samplings.

An enrolled patient was sampled three times, and the disease progression was found in the 6th week after the patient accepted the clinical treatment, as shown in FIG. 14A. However, with the method of the present disclosure, for example, the absolute median difference of CNV log R ratio (FIG. 14B) and the expression level of protein (FIG. 14C) were both increased, after normalizing the probability values, the obtained probability value that the sample to be tested is derived from the tumor was higher, indicating disease progression. And the results of the second sampling analysis showed the disease progression earlier than the clinical results.

Example 8

A method to detect single nucleotide variant (SNV) in cfDNA by single reads was designed, which is suitable for predicting cancer risk and calculating blood tumor mutation burden (bTMB). Typically, the widely-used SNV detection method sequences high-depth data and compares them on the same base between tumor and normal samples to determine the probabilities of somatic SNV and sequencing error. By comparing the ratio of these two probabilities with predefined cutoff, it could be determined whether there is somatic SNV on this base. This method requires high sequencing depth (>800×) in order to have a reliable discovery rate on a single base, so it is only affordable for small target regions which usually cover less than 1/1000 of the whole genome.

Figure 15:
FIG. 15 shows different types of sequencing reads. The SNV mutation site in a reference sequence and its corresponding bases within detected reads are labeled with a box.

The method described herein uses low-depth sequencing without amplicon or capture to improve efficiency of sequencing data. Although detecting SNV on a specific base is not guaranteed due to low depth, overall variant totals across whole genome could be captured. Sequencing depth used in this method is about 3X. The ctDNA content is 1%-10% of whole plasma cfDNA, so there is a possibility of about 3%-30% to capture tumor signals. For the tumor variant detection under low depth, the biggest challenge is to distinguish true tumor variants from sequencing errors. To solve this problem, more than 100 healthy samples were used as a control database and sequenced through the full-length reads (FIG. 15), i.e. sequencing the same molecule from two opposite directions and the reads overlapping each other.

Step 1: There was a known SNV mutation at one site in a reference sequence. The wild-type base is a "A" and when mutated, the base is a "C". If the sequencing results of reads1 and reads2 from one fragment are consistent, the detected SNV base is either: (1) identical to the reference sequence (named "Ref_base_PE"); (2) a mutational base (named "Alt_base_PE"); or (3) identical to other expected bases (named "Other_PE"). If the sequencing results of reads1 and reads2 are inconsistent, i.e., different bases at the same site with a similar base quality (base Phred quality score>30 and mapping quality score>30), the group is named "Diff_PE". The control database was used to statistically calculate the reads number of the four groups across whole genome of each control sample, the corresponding base quality, and the mapping quality. The groups of "Other_PE" and "Diff_PE" were considered as background noise. "Other_PE" might be caused by 8-oxoG, cytosine deamination for ctDNA isolation, or PCR error; and "Diff_PE" might be caused by sequencing error. The method of maximum likelihood was used to calculate the probability of true mutation and artifact error.

Step 2: Filtering germline SNP and Error.

(1) Using another NGS alignment software (e.g., Bowite, SOAP2, or GATK IndelRealignment) to re-align the potential SNV supporting reads. If the reads mapping position is different from BWA (the mapping software used in Step 1), the SNV can be filtered out.

(2) Using published database to filter genome SNP (e.g., dbSNP, 1000G_phase3, gnomad, ExAC_nonTCGA).

(3) Using in-house healthy samples as controls to filter recurrent SNV (Af>0.3%).

(4) Filtering SNV located in simple repeat regions or black regions, which download from ENCODE project.

Step 3: Calculating bTMB.

Because the DNA fragment size from ctDNA is usually less than that of cfDNA, SNV with a fragment size of supporting reads more than 140 bp can be filtered.

bTMB=(# of SNV-# of Diff_PE/2)/Overlapping Base*1000000

Figure 16:
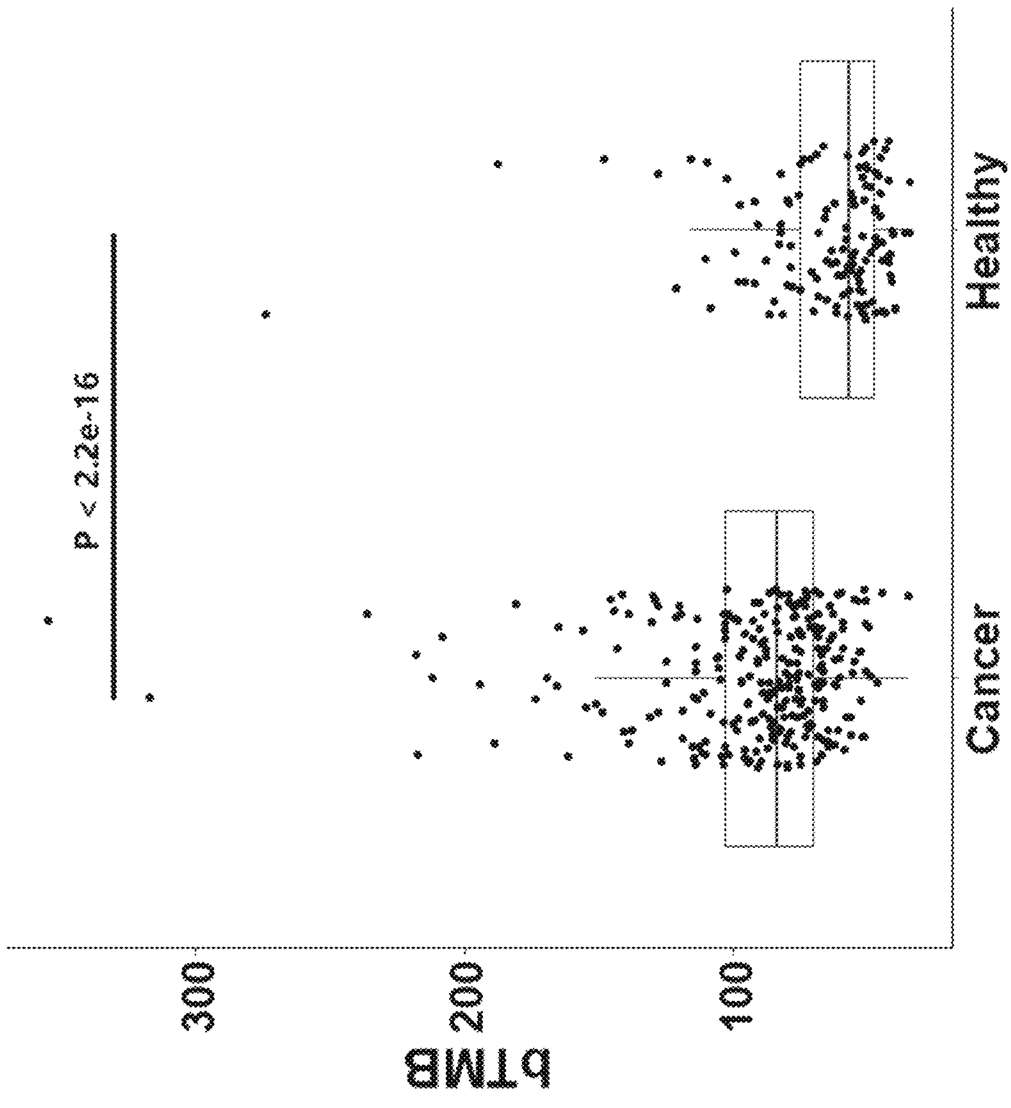
FIG. 16 shows sample mutation burden (bTMB) values in cancer patients ("Cancer") and healthy individuals ("Healthy").

A total of 389 plasma samples were used to validated this method. As shown in FIG. 16 and the table below, the bTMB in cancer patients was significant higher than that in healthy individuals.

TABLE 13

| Sample type | Number of samples |
|---|---|
| Liver Cancer | 46 |
| Colorectum Cancer | 44 |
| Stomach Cancer | 42 |
| Breast Cancer | 43 |
| Lung Cancer | 25 |
| Other Cancer | 62 |
| Healthy | 127 |

Figure 17A:
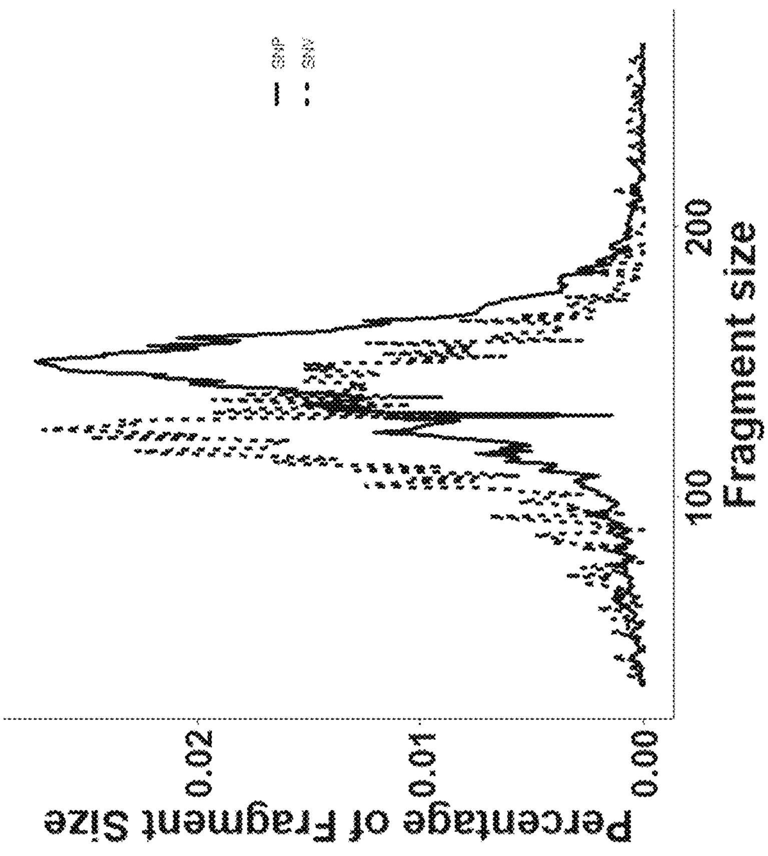
FIG. 17A shows distribution of the fragment size of SNV (dashed line) and SNP (solid line).
Figure 17B:
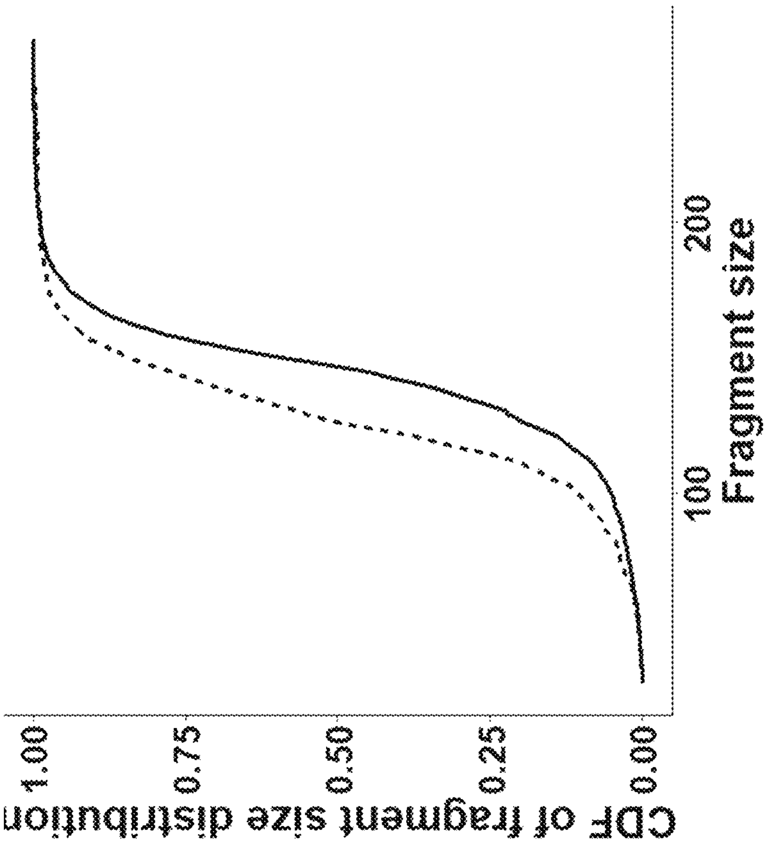
FIG. 17B shows the CDF (cumulative distribution function) of fragment size distributions of SNV (dashed line) and SNP (solid line).
Figure 18:
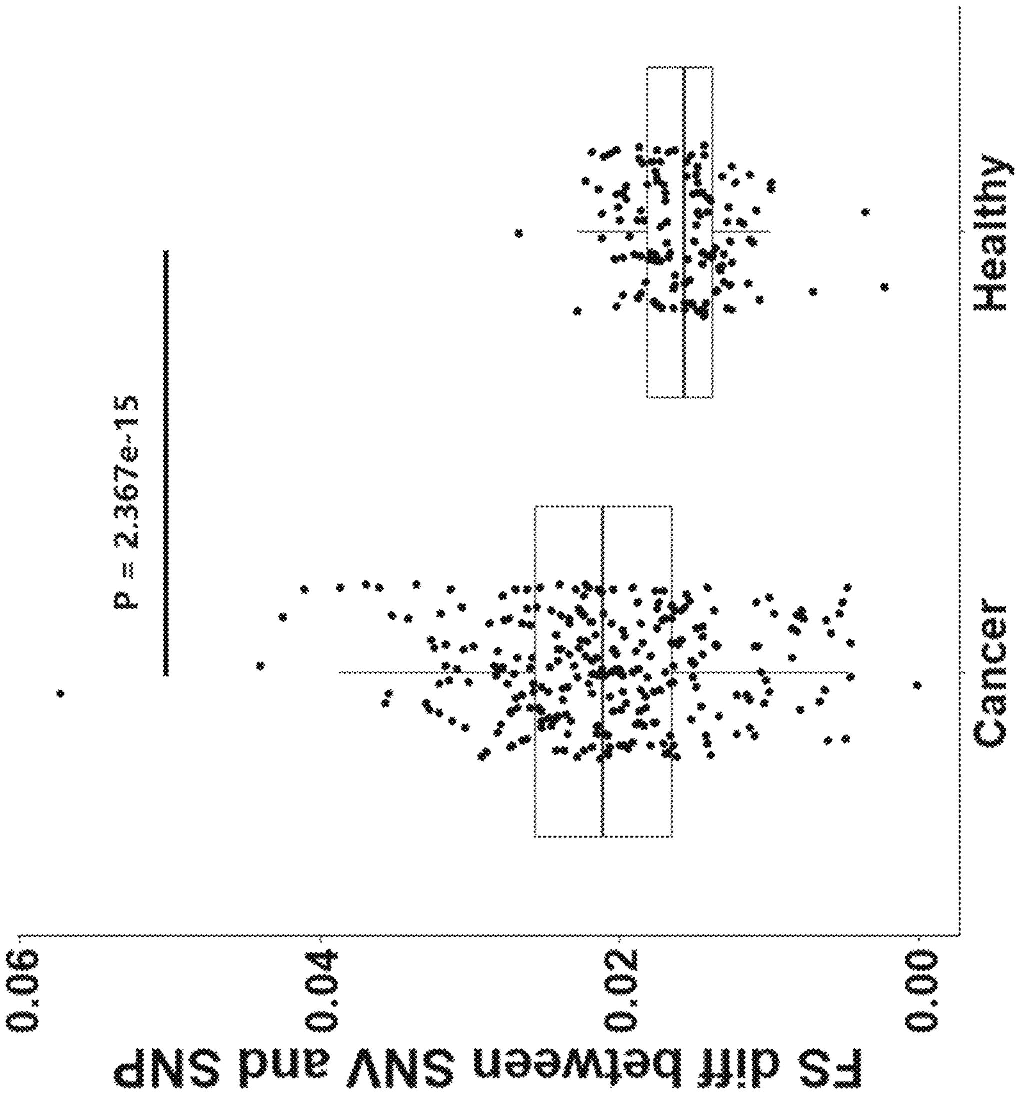
FIG. 18 shows the maximum different ratio between the cumulative distribution of SNV and SNP (named FS_Diff) in cancer patients ("Cancer") and healthy individuals ("Healthy").
Figure 19:
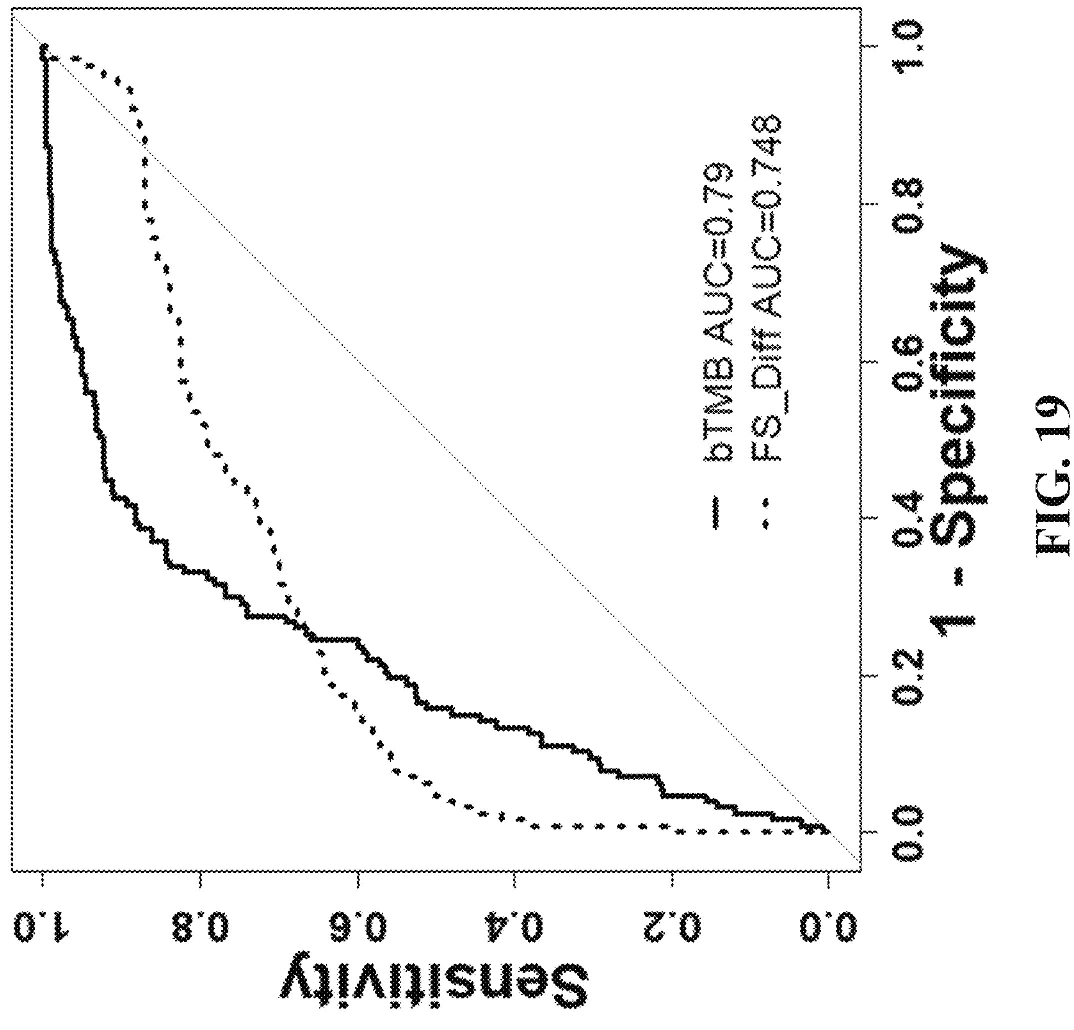
FIG. 19 shows a ROC curve graph indicating capabilities for cancer patient prediction based on bTMB and FS_diff in Example 9 of the present disclosure.

Step 4: Calculating FS_Diff between SNV and SNP. Here, the germline SNP is originated from normal (e.g., healthy) cells, and the SNV is originated from tumor cells. As shown in FIGS. 17A-17B, the fragment size of SNV was significantly less than that of SNP. For example, the SNV mutations were classified based on the corresponding tumor tissue sequencing data, and the SNP mutations were classified based on published database. The fragment size distribution of SNV showed a horizontal displacement (almost 20 bp) relative to that of SNP. This feature could be used to predict whether the plasma sample is originated from a tumor patient. The maximum different ratio between the cumulative distribution of SNV and SNP (named FS_Diff) among the 389 plasma samples is shown in FIG. 18. In addition, the capabilities for cancer patient prediction based on bTMB and FS_diff are shown in FIG. 19, with AUC values determined as 0.79 and 0.748, respectively.

Example 9

According to the examples described herein, the following various dimensions were calculated: cfDNA concentration, CNV value, the probability that the test sample is derived from tumor patients predicted based on tumor marker and fragment size, the proportion of mitochondrial, bTMB from SNV, and the FS_Diff between SNP and SNV (below table showed several examples).

The machine learning methods, for example, LASSO, RF or GBM, served as input, and the modeling was performed with 127 healthy subjects and 262 tumor patients, obtaining the weights of various dimensions (See the table below).

TABLE 14

| Age | Gender | Type | cfDNA concentration | TSM.Lasso | chrM_Ratio | CNV.value | FS.GEM | SNV_FS_Diff | SNV_bTMB |
|---|---|---|---|---|---|---|---|---|---|
| 64 | M | Cancer | 121.28 | 0.42 | 11.31 | 3.57 | 0.94 | 0.022 | 77.32 |
| 53 | M | Cancer | 14.85 | 1.00 | 2.71 | 3.54 | 0.87 | 0.027 | 60.71 |
| 62 | M | Cancer | 14.83 | 0.18 | 5.22 | 0.36 | 0.74 | 0.021 | 79.44 |
| 49 | F | Cancer | 10.97 | 0.86 | 7.09 | 0.58 | 0.90 | 0.020 | 96.10 |
| 45 | F | Cancer | 11.52 | 0.51 | 7.25 | 0.94 | 0.53 | 0.022 | 80.73 |
| 46 | F | Cancer | 9.52 | 0.99 | 19.44 | 2.99 | 0.94 | 0.021 | 145.79 |
| 70 | M | Cancer | 13.20 | 1.00 | 17.39 | 3.80 | 0.96 | 0.032 | 114.20 |
| 52 | F | Healthy | 25.48 | 0.39 | 2.71 | 1.31 | 0.13 | 0.011 | 43.96 |
| 45 | M | Healthy | 10.50 | 0.84 | 15.07 | 2.30 | 0.43 | 0.020 | 62.19 |
| 46 | F | Healthy | 10.85 | 0.49 | 5.97 | 1.09 | 0.37 | 0.017 | 50.72 |
| 48 | F | Healthy | 9.52 | 0.28 | 6.60 | 1.60 | 0.22 | 0.023 | 50.79 |
| 73 | M | Healthy | 7.63 | 0.45 | 4.94 | 0.73 | 0.22 | 0.018 | 55.00 |
| 40 | M | Healthy | 6.92 | 0.50 | 4.22 | 1.21 | 0.28 | 0.018 | 59.69 |
| 75 | F | Healthy | 12.81 | 0.55 | 3.25 | 0.73 | 0.51 | 0.019 | 71.36 |
| 66 | F | Healthy | 11.48 | 0.68 | 4.28 | 1.16 | 0.38 | 0.022 | 56.33 |
| 40 | M | Healthy | 4.48 | 0.54 | 149.73 | 1.02 | 0.21 | 0.020 | 92.20 |
| 65 | M | Healthy | 39.50 | 0.69 | 40.43 | 1.02 | 0.58 | 0.013 | 79.67 |
| 28 | M | Healthy | 6.24 | 0.41 | 5.57 | 0.73 | 0.18 | 0.017 | 57.92 |
| 61 | F | Healthy | 12.11 | 0.25 | 2.46 | 1.87 | 0.12 | 0.014 | 58.26 |

For the sample to be tested, the probability that the sample to be tested is derived from the tumor patient was predicted based on the above weights. The specificity of 98% was selected as the cut-off value, and the sample greater than the threshold was predicted to be a tumor sample. The weights of each feature in one LASSO model was shown:

TABLE 15

| | |
|---|---|
| (Intercept) | −1.68125 |
| cfDNA_concentration | −0.24078 |
| Protein.Lasso | −0.72722 |
| chrM_Ratio | 0.584555 |
| CNV.value | −0.37378 |
| FS.GBM | −1.30632 |
| SNV_FS_Diff | −0.42911 |
| SNV_bTMB | −0.6352 |

Figure 20:
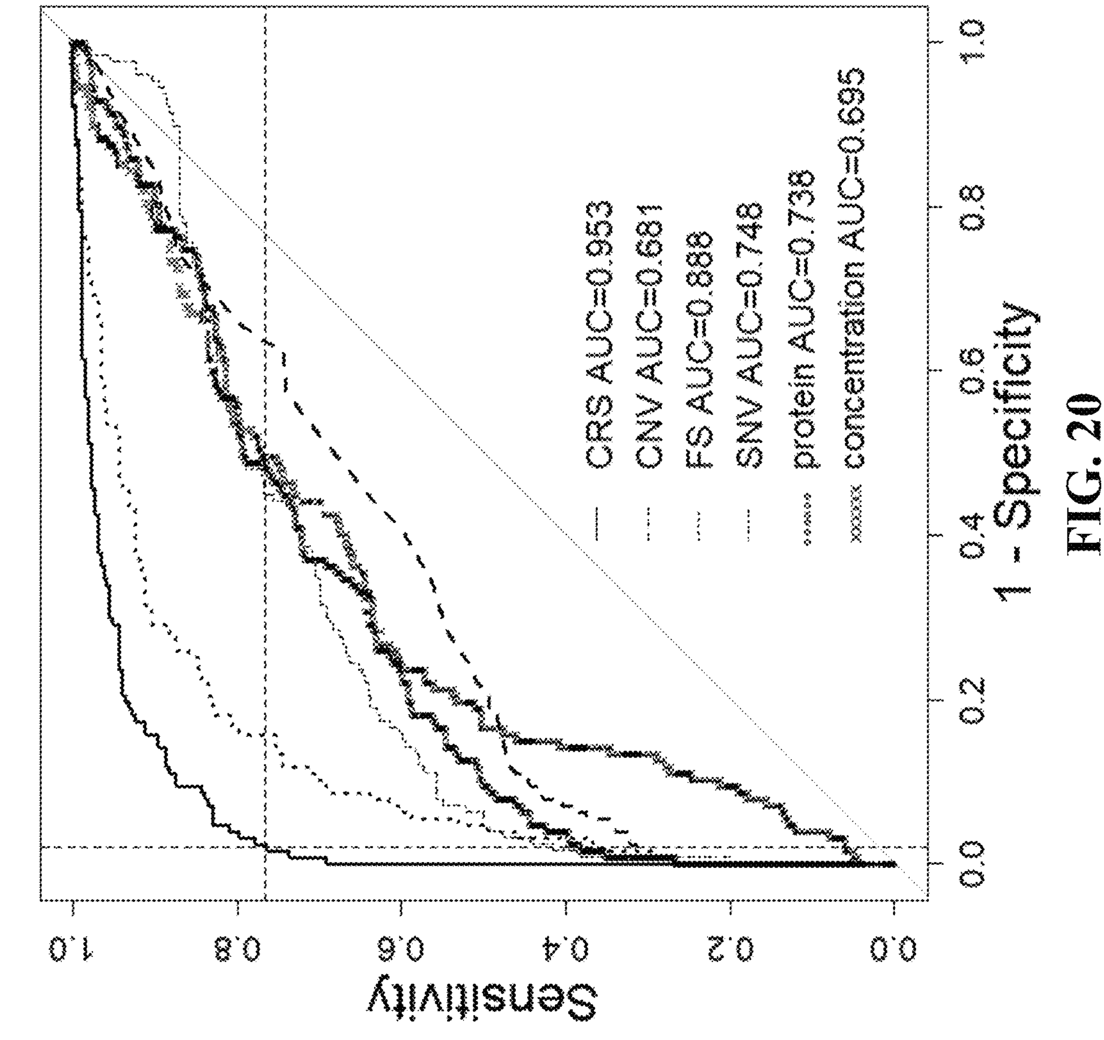
FIG. 20 shows a ROC curve graph indicating capabilities for cancer patient prediction based multiple features in Example 10 of the present disclosure.

The RF method was used to build the predict model, and the process was repeated for 100 times. The average predicted value of being a cancer based on the 100 RF models was the final cancer risk score (named CRS). In addition, the capabilities for cancer patient prediction based on the features are shown in FIG. 20.

In the description of this specification, the description referring to the term “an embodiment”, “some embodiments”, “an example”, “specific examples”, or “some examples” means that the specific features, structures, materials or characteristics described in conjunction with the embodiment or example shall be included in at least an embodiment or example of the present disclosure. In this specification, the schematic expression of the above terms does not necessarily refer to the same embodiment or example. Moreover, the described specific features, structures, materials, or characteristics may be combined in any one or more embodiments or examples in any suitable manner. In addition, without contradicting each other, those skilled in the art may incorporate and combine different embodiments or examples and features of the different embodiments or examples described in the specification.

Although the embodiments of the present disclosure have been shown and described above, it should be understood that the above-mentioned embodiments are illustrative and shall not be construed as limitations of the present disclosure, and within the scope of the present disclosure, those skilled in the art can make changes, modifications, replacements and variations to the above embodiments.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for cancer detection, recurrence monitoring and treatment response assessment, the method comprising:
- obtaining a biological sample from a subject;
- obtaining a chromosome instability index in the biological sample, wherein the chromosome instability index measures the degree of genomic structural variation based on copy-number aberrations (CNAs) across genomic regions of sequencing data of the biological sample;
- determining a probability that the biological sample is derived from a cancer patient based on a fragment size, wherein the determining comprises:
  - a) obtaining a cell-free DNA (cfDNA) sample from the biological sample;
  - b) constructing a sequencing library from the cfDNA sample, and sequencing the library to generate sequencing reads;
  - c) extracting a plurality of fragment size metrics from the sequencing reads;
  - d) computing a plurality of the statistical features of the fragment size metrics; and
  - processing a machine learning model input comprising the statistical features using a first machine learning model to predict a probability value indicating the likelihood of the biological sample being derived from a cancer patient, wherein the model comprises one or more of a support vector machine (SVM), a least absolute shrinkage and selection operator (LASSO), or a Gradient Boosting Machine (GBM);
- determining a probability that the biological sample is derived from a cancer patient based on a protein tumor marker content;
- determining the proportion of mitochondrial DNA fragments below 150 bp in the biological sample;
- obtaining a concentration of cfDNA in the biological sample;
- determining a cancer predicting score that measures a probability that the biological sample is derived from a cancer patient based on the chromosome instability index, the probability that the biological sample is derived from the cancer patient based on the fragment size, the probability that the biological sample is derived from the cancer patient based on the protein tumor marker content, the proportion of mitochondrial DNA fragments below 150 bp, and the concentration of cfDNA; and
- treating the subject with a cancer therapy, in response to the cancer predicting score exceeding a reference threshold value; wherein:
- determining the probability that the biological sample is derived from a cancer patient based on a fragment size further comprises:
  - obtaining a genome of the biological sample, constructing a sequencing library and sequencing to obtain, based on sequencing reads in a sequencing result, a ratio of the numbers of the sequencing reads of inserts in different predetermined length ranges in different chromosomal regions, and calculating a sum of deviations, wherein the machine learning model input further comprises the sum of deviations, and wherein
- the ratio of the numbers of the sequencing reads of inserts in different predetermined length ranges in different chromosomal regions is obtained by the following steps:
  - a) dividing a human reference genome into a plurality of window bins having a same length;
  - b) determining the numbers of sequencing reads of inserts in different predetermined length ranges in each of the plurality of window bins; and
  - c) determining a ratio of the numbers of sequencing reads of inserts in different predetermined length ranges in each of the plurality of window bins.

2. The method of claim 1, wherein an algorithm for determining the probability that the biological sample is derived from a cancer patient is expressed in the following calculation formula:

$$P = \frac{1}{1 + e^{-(\alpha+\beta_1 * x_1 + \beta_2 * x_2 + \beta_3 * x_3 + \beta_4 * x_4 + \beta_5 * x_5 + \beta_6 * x_6 + \beta_7 * x_7)}},$$

wherein $x_1$ represents the chromosome instability index;
- $x_2$ represents the probability that the biological sample is derived from a cancer patient determined based on the fragment size;
- $x_3$ represents the probability that the biological sample is derived from a cancer patient determined based on the protein tumor marker content;
- $x_4$ represents the proportion of mitochondrial DNA fragments below 150 bp among all reads;
- $x_5$ represents the plasma cfDNA concentration; and
- $\alpha$ is a constant, β1, β2, β3, β4, and β5 are regression coefficients predicted by machine learning logistic regression.

3. The method of claim 1, wherein the statistical features of the fragment size metrics comprise P100, P180, P250, a peak-to-valley spacing, and a fragment length corresponding to a peak value in an insert length distribution based on the plurality of sequencing reads;
- wherein P100 refers to a ratio of the number of inserts of 30-100 bp in the biological sample to the total number of inserts;
- P180 refers to a ratio of the number of inserts of 180-220 bp in the biological sample to the total number of inserts;
- P250 refers to a ratio of the number of inserts of 250-300 bp in the biological sample to the total number of inserts;
- the peak-to-valley spacing refers to a difference between a ratio of a peak and a ratio of a valley adjacent to the peak, wherein the peak and the valley are observed in a size distribution of cfDNA samples from shallow whole genome sequencing data in a range of insert length smaller than 150 bp; a position of the peak corresponds to an insert length of x, the ratio of the peak is calculated by dividing the number of reads in [x−2, x+2] by the total number of reads; a position of the valley corresponds an insert length of y, the ratio of the valley is calculated by dividing the number of reads in [y−2, y+2] by the total number of reads; and
- the fragment length corresponding to the peak value in the insert length distribution is a fragment length corresponding to the largest number of sequencing reads based on the number of sequencing reads corresponding to different insert lengths of a statistical sample.

4. The method of claim 1, wherein the sum of deviations is calculated by summing up absolute values of a ratio of the sums of the numbers of reads of inserts minus a median value of all ratios of the sums of the numbers of reads of inserts, according to the following formula:

$$\Sigma abs(S_i/L_i\text{-}median(S_1/L_1,S_2/L_2, \ldots ,S_n/L_n)$$

wherein S represents an insert of 100-150 bp, L represents an insert of 151-220 bp, abs( ) denotes calculating an absolute value of values in the parentheses, median( ) denotes calculating the median value of values in the parentheses, i represents a genomic region in the human genome, and n is the total number of bins.

5. The method of claim 4, wherein the ratio of the sums of the numbers of reads of inserts is obtained by the following steps:

(1) calculating a sum of the numbers of reads of inserts of predetermined length ranges in one predetermined bin, which comprises: in the one predetermined bin, calculating a sum of the numbers of reads of inserts in a length range of 100 to 150 bp, and calculating a sum of the numbers of reads of inserts in a length range of 151 to 220 bp; and (2) dividing the sum of the numbers of reads of inserts in a length range of 100 to 150 bp by the sum of the numbers of reads of inserts in a length range of 151 to 220 bp, to obtain the ratio of the sums of the numbers of reads of inserts.

6. The method of claim 1, wherein the proportion of mitochondrial DNA fragments below 150 bp in the biological sample is determined by the following steps:

determining the number of sequencing reads aligned to a reference mitochondrial gene sequence; and selecting inserts smaller than 150 bp from the sequencing reads aligned to the reference mitochondrial gene sequence, calculating the number of sequencing reads of the inserts smaller than 150 bp, and dividing the number of sequencing reads of the inserts smaller than 150 bp by the total number of sequencing reads.

7. The method of claim 1, wherein the biological sample is blood, body fluid, urine, saliva or skin.

8. The method of claim 1, further comprising:

selecting samples from a patient suspected of having cancer at different times; and predicting the source of the sample using the method for cancer detection, recurrence monitoring and treatment response assessment of a sample.

9. An electronic device for evaluating a source of a sample, the electronic device comprising a memory and a processor, wherein the processor is configured to read an executable program code stored in the memory and to execute a program corresponding to the executable program code, to perform the method for cancer detection, recurrence monitoring and treatment response assessment according to claim 1.

10. A non-transitory computer-readable storage medium, configured to store a computer program, wherein the computer program is configured to, when executed by a processor, perform the method for cancer detection, recurrence monitoring and treatment response assessment according to claim 1.

11. The method of claim 1, further comprising obtaining a prediction model by the following steps:

a step M1 of determining a chromosome instability index, a fragment size, a protein tumor marker content, a proportion of mitochondrial DNA fragments below 150 bp and a plasma cfDNA concentration of a known type of sample to obtain the chromosome instability index, the fragment size, the tumor protein content, the proportion of mitochondrial DNA fragments below 150 bp and the plasma cfDNA concentration of the known type of sample, wherein the known type of sample is composed of a known number of healthy samples and a known number of tumor samples;

a step M2 of standardization processing the data of the known type of sample to obtain a standard deviation and a variance of the data of the known type of sample, the data comprising the chromosome instability index, the fragment size, the protein tumor marker content, the proportion of mitochondrial DNA fragments below 150 bp, and the plasma cfDNA concentration that are obtained in the step M1;

a step M3 of determining a prediction effect, variance and bias of the machine learning model by using a machine learning model and a 10-fold cross-validation method; and a step M4 of determining the prediction model based on the prediction effect, variance and bias of the machine learning model.

12. A method for cancer detection, recurrence monitoring and treatment response assessment, the method comprising:

obtaining a biological sample from a subject;

obtaining a chromosome instability index in the biological sample, wherein the chromosome instability index measures the degree of genomic structural variation based on copy-number aberrations (CNAs) across genomic regions of sequencing data of the biological sample;

determining a probability that the biological sample is derived from a cancer patient based on a fragment size, wherein the determining comprises:

a) obtaining a cell-free DNA (cfDNA) sample from the biological sample;

b) constructing a sequencing library from the cfDNA sample, and sequencing the library to generate sequencing reads;

c) extracting a plurality of fragment size metrics from the sequencing reads;

d) computing a plurality of the statistical features of the fragment size metrics; and processing a machine learning model input comprising the statistical features using a first machine learning model to predict a probability value indicating the likelihood of the biological sample being derived from a cancer patient, wherein the model comprises one or more of a support vector machine (SVM), a least absolute shrinkage and selection operator (LASSO), or a Gradient Boosting Machine (GBM);

determining a probability that the biological sample is derived from a cancer patient based on a protein tumor marker content;

determining a cancer predicting score that measures a probability that the biological sample is derived from a cancer patient based on the chromosome instability index, the probability that the biological sample is derived from the cancer patient based on the fragment size, the probability that the biological sample is derived from the cancer patient based on the protein tumor marker content; and treating the subject with a cancer therapy, in response to the cancer predicting score exceeding a reference threshold value; wherein:

determining the probability that the biological sample is derived from a cancer patient based on a fragment size further comprises:

obtaining a genome of the biological sample, constructing a sequencing library and sequencing to obtain, based on sequencing reads in a sequencing result, a ratio of the numbers of the sequencing reads of inserts in different predetermined length ranges in different chromosomal regions, and calculating a sum of deviations, wherein the machine learning model input further comprises the sum of deviations, and wherein the ratio of the numbers of the sequencing reads of inserts in different predetermined length ranges in different chromosomal regions is obtained by the following steps:

a) dividing a human reference genome into a plurality of window bins having a same length;

b) determining the numbers of sequencing reads of inserts in different predetermined length ranges in each of the plurality of window bins; and c) determining a ratio of the numbers of sequencing reads of inserts in different predetermined length ranges in each of the plurality of window bins.

* * * * *

SEQUENCE LISTING

```
<160> NUMBER OF SEQ ID NOS: 11

<210> SEQ ID NO 1
<211> LENGTH: 50
<212> TYPE: DNA
<213> ORGANISM: Artificial
<220> FEATURE:
<223> OTHER INFORMATION: synthetic oligonucleotide

<400> SEQUENCE: 1

ggtggatcac aaggtcagga gatcaagacc atcctggcta acacggtgaa                50


<210> SEQ ID NO 2
<211> LENGTH: 27
<212> TYPE: DNA
<213> ORGANISM: Artificial
<220> FEATURE:
<223> OTHER INFORMATION: synthetic oligonucleotide

<400> SEQUENCE: 2

tcacaaggtc aggagatcaa gaccatc                                         27


<210> SEQ ID NO 3
<211> LENGTH: 31
<212> TYPE: DNA
<213> ORGANISM: Artificial
<220> FEATURE:
<223> OTHER INFORMATION: synthetic oligonucleotide

<400> SEQUENCE: 3

aaggtcagga gatcaagacc atcctggcta a                                    31


<210> SEQ ID NO 4
<211> LENGTH: 27
<212> TYPE: DNA
<213> ORGANISM: Artificial
<220> FEATURE:
<223> OTHER INFORMATION: synthetic oligonucleotide

<400> SEQUENCE: 4

tcacaaggtc aggcgatcaa gaccatc                                         27


<210> SEQ ID NO 5
<211> LENGTH: 31
<212> TYPE: DNA
<213> ORGANISM: Artificial
<220> FEATURE:
<223> OTHER INFORMATION: synthetic oligonucleotide

<400> SEQUENCE: 5

aaggtcaggc gatcaagacc atcctggcta a                                    31
```

<210> SEQ ID NO 6
<211> LENGTH: 27
<212> TYPE: DNA
<213> ORGANISM: Artificial
<220> FEATURE:
<223> OTHER INFORMATION: synthetic oligonucleotide

<400> SEQUENCE: 6
tcacaaggtc aggtgatcaa gaccatc 27

<210> SEQ ID NO 7
<211> LENGTH: 31
<212> TYPE: DNA
<213> ORGANISM: Artificial
<220> FEATURE:
<223> OTHER INFORMATION: synthetic oligonucleotide

<400> SEQUENCE: 7
aaggtcaggt gatcaagacc atcctggcta a 31

<210> SEQ ID NO 8
<211> LENGTH: 27
<212> TYPE: DNA
<213> ORGANISM: Artificial
<220> FEATURE:
<223> OTHER INFORMATION: synthetic oligonucleotide

<400> SEQUENCE: 8
tcacaaggtc aggtgatcaa gaccatc 27

<210> SEQ ID NO 9
<211> LENGTH: 31
<212> TYPE: DNA
<213> ORGANISM: Artificial
<220> FEATURE:
<223> OTHER INFORMATION: synthetic oligonucleotide

<400> SEQUENCE: 9
aaggtcaggc gatcaagacc atcctggcta a 31

<210> SEQ ID NO 10
<211> LENGTH: 27
<212> TYPE: DNA
<213> ORGANISM: Artificial
<220> FEATURE:
<223> OTHER INFORMATION: synthetic oligonucleotide

<400> SEQUENCE: 10
tcacaaggtc aggggatcaa gaccatc 27

<210> SEQ ID NO 11
<211> LENGTH: 31
<212> TYPE: DNA
<213> ORGANISM: Artificial
<220> FEATURE:
<223> OTHER INFORMATION: synthetic oligonucleotide

<400> SEQUENCE: 11
aaggtcagga gatcaagtcc atcctggcta a 31